United States Patent
Parnell et al.

(10) Patent No.: US 11,724,989 B2
(45) Date of Patent: *Aug. 15, 2023

(54) MCT4 INHIBITORS FOR TREATING DISEASE

(71) Applicant: Vettore, LLC, San Francisco, CA (US)

(72) Inventors: Kenneth Mark Parnell, Kaysville, UT (US); John McCall, Boca Grande, FL (US)

(73) Assignee: Vettore, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/481,660

(22) Filed: Sep. 22, 2021

(65) Prior Publication Data

US 2022/0251045 A1  Aug. 11, 2022

Related U.S. Application Data

(60) Continuation of application No. 17/030,243, filed on Sep. 23, 2020, now Pat. No. 11,155,522, which is a continuation of application No. 16/222,964, filed on Dec. 17, 2018, now abandoned, which is a division of application No. 15/180,623, filed on Jun. 13, 2016, now Pat. No. 10,202,350.

(60) Provisional application No. 62/174,685, filed on Jun. 12, 2015.

(51) Int. Cl.

| | |
|---|---|
| C07D 231/12 | (2006.01) |
| A61P 35/00 | (2006.01) |
| A61K 31/415 | (2006.01) |
| A61K 31/4155 | (2006.01) |
| A61K 31/427 | (2006.01) |
| A61K 31/4439 | (2006.01) |
| A61K 31/5377 | (2006.01) |
| A61K 45/06 | (2006.01) |
| C07D 401/06 | (2006.01) |
| C07D 405/12 | (2006.01) |
| C07D 409/04 | (2006.01) |
| C07D 417/04 | (2006.01) |

(52) U.S. Cl.
CPC .......... *C07D 231/12* (2013.01); *A61K 31/415* (2013.01); *A61K 31/4155* (2013.01); *A61K 31/427* (2013.01); *A61K 31/4439* (2013.01); *A61K 31/5377* (2013.01); *A61K 45/06* (2013.01); *A61P 35/00* (2018.01); *C07D 401/06* (2013.01); *C07D 405/12* (2013.01); *C07D 409/04* (2013.01); *C07D 417/04* (2013.01)

(58) Field of Classification Search
CPC ...... C07D 231/12; C07D 401/06; A61P 35/00
See application file for complete search history.

(56) References Cited

U.S. PATENT DOCUMENTS

| | | |
|---|---|---|
| 3,895,026 A | 7/1975 | Palazzo |
| 5,078,780 A | 1/1992 | Moser |
| 5,925,768 A | 7/1999 | Barth |
| 8,901,314 B2 | 12/2014 | Wall |
| 9,296,728 B2 | 3/2016 | Mereddy |
| 10,202,350 B2 | 2/2019 | Parnell |
| 10,214,492 B2 | 2/2019 | Parnell |
| 11,155,522 B2 | 10/2021 | Parnell |
| 11,292,767 B2 | 4/2022 | Parnell |
| 2009/0042864 A2 | 2/2009 | Shia |
| 2011/0003874 A1 | 1/2011 | Guglielmotti |
| 2011/0160248 A1 | 6/2011 | Zhou |
| 2013/0190324 A1 | 7/2013 | Kompella |
| 2014/0378477 A1 | 12/2014 | Lisanti |
| 2016/0115146 A1 | 4/2016 | Draoui |
| 2018/0162822 A1 | 6/2018 | Parnell |
| 2019/0112274 A1 | 4/2019 | Parnell |
| 2019/0112275 A1 | 4/2019 | Parnell |
| 2022/0251047 A1 | 8/2022 | Parnell |

FOREIGN PATENT DOCUMENTS

| | | |
|---|---|---|
| CN | 102093341 | 6/2011 |
| WO | 1999004770 | 2/1999 |
| WO | 2005054852 | 6/2005 |
| WO | 2008060771 | 5/2008 |
| WO | 2009109613 | 9/2009 |

(Continued)

OTHER PUBLICATIONS

Dyson, et al., "Mir", Chemistry of Synthetic Drugs, Moscow: Publishing House, pp. 12-19, (1964).

(Continued)

*Primary Examiner* — Kamal A Saeed
(74) *Attorney, Agent, or Firm* — Cynthia Hathaway; Lauren L. Stevens; Erik M. Larsen

(57) ABSTRACT

Provided herein is a method for treating a monocarboxylate transporter MCT4-mediated disorder in a subject in need thereof. The method comprises the step of administering to the subject a compound of structural Formula I

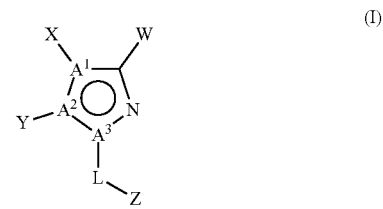

(I)

and/or a salt thereof. The treatment of the monocarboxylate transporter MCT4-mediated disorder may inhibit activity of MCT4, or a mutant thereof, sometimes with at least a 100-fold selectivity for MCT4 over MCT1.

23 Claims, No Drawings

(56) References Cited

FOREIGN PATENT DOCUMENTS

| WO | 2013109972 | 7/2013 |
|---|---|---|
| WO | 2013171317 | 11/2013 |
| WO | 2014028803 | 2/2014 |
| WO | 2014195507 | 12/2014 |
| WO | 2015188934 | 12/2015 |
| WO | 2016192982 | 12/2016 |
| WO | 2016201416 | 12/2016 |
| WO | 2016201426 | 12/2016 |
| WO | 2018111904 | 6/2018 |

OTHER PUBLICATIONS

International Application No. PCT/US2016/037213; International Preliminary Report on Patentability, dated Dec. 21, 2017; 7 pages.

International Application No. PCT/US2016/037213; International Search Report and Written Opinion of the International Searching Authority, dated Sep. 2, 2016; 11 pages.

International Application No. PCT/US2017/065864; International Preliminary Report on Patentability, dated Jun. 27, 2019; 6 pages.

International Application No. PCT/US2017/065864; International Search Report and Written Opinion of the International Searching Authority, dated Apr. 12, 2018; 10 pages.

Jendrossek, V., "Targeting Apoptosis Pathways by Celecoxib in Cancer", Cancer Lett., 332(2):313-24, (2013).

Katoch-Rouse, R. et al., "Synthesis, Structure-Activity Relationship, and Evaluation of SR141716 Analogues: Development of Central Cannabinoid Receptor Ligands with Lower Lipophilicity", J. Med. Chem., 46:642-5, (2003).

Patani, G. et al., "Bioisosterism: A Rational Approach in Drug Design", Chem Rev., 96(8):3147-76, (1996).

Persson, T. et al., "Pyrazole Carboxamides and Carboxylic Acids as Protein Kinase Inhibitors in Aberrant Eukaryotic Signal Transduction: Induction of Growth Arrest in MCF-7 Cancer Cells", Org Biomol Chem., 5(24):3963-70, (2007).

Pokrovskii, V. (1997), Popular Medical Encyclopedia, Ulianovsk: Knogochei Publishing House, 1997, p. 317.

PubChem CID 82220344, date created Oct. 20, 2014, date accessed Mar. 28, 2018, 3 pages.

Ragavan, R. et al., "Synthesis and Antimicrobial Activities of Novel 1,5-Diaryl Pyrazoles", Eur J Med Chem., 45(3):1173-80, (2010).

Szabó, G. et al., "New Celecoxib Derivatives as Anti-Inflammatory Agents", J Med Chem., 51(1):142-7, (2008).

Tabrizi, M. et al., "Pyrazole Phenylcyclohexylcarbamates as Inhibitors of Human Fatty Acid Amide Hydrolases (FAAH)", Eur J Med Chem., 97:289-305, (2015).

Tu, G. et al., "Design, Synthesis and Biological Evaluation of CB1 Cannabinoid Receptor Ligands Derived from the 1,5-Diarylpyrazole Scaffold", J Enzyme Inhib and Med Chem., 26(2):222-30, (2011).

U.S. Appl. No. 15/180,623; Corrected Notice of Allowability, dated Oct. 16, 2018; 5 pages.

U.S. Appl. No. 15/180,623; Examiner-Initiated Interview Summary, dated Oct. 1, 2018; 1 page.

U.S. Appl. No. 15/180,623; Examiner-Initiated Interview Summary, dated Oct. 16, 2018; 1 page.

U.S. Appl. No. 15/180,623; Non-Final Office Action, dated Mar. 19, 2018; 18 pages.

U.S. Appl. No. 15/180,623; Notice of Allowance, dated Oct. 1, 2018; 21 pages.

U.S. Appl. No. 15/839,539; Examiner-Initiated Interview Summary, dated Oct. 3, 2018; 1 page.

U.S. Appl. No. 15/839,539; Notice of Allowance, dated Oct. 3, 2018; 20 pages.

U.S. Appl. No. 16/222,949; Final Office Action, dated Jul. 20, 2021; 18 pages.

U.S. Appl. No. 16/222,949; Non-Final Office Action, dated Mar. 20, 2020; 19 pages.

U.S. Appl. No. 16/222,949; Non-Final Office Action, dated Sep. 24, 2019; 32 pages.

U.S. Appl. No. 16/222,949; Notice of Allowance, dated Nov. 23, 2021; 9 pages.

U.S. Appl. No. 16/222,964; Applicant-Initiated Interview Summary, dated Nov. 12, 2019; 3 pages.

U.S. Appl. No. 16/222,964; Non-Final Office Action, dated Nov. 1, 2019; 39 pages.

U.S. Appl. No. 16/222,964; Notice of Allowance, dated Jun. 24, 2020; 12 pages.

U.S. Appl. No. 16/222,964; Notice of Allowance, dated Mar. 2, 2020; 12 pages.

U.S. Appl. No. 16/222,964; Notice of Allowance, dated Nov. 25, 2019; 12 pages.

U.S. Appl. No. 17/030,243; Notice of Allowance, dated Jun. 28, 2021; 16 pages.

U.S. Appl. No. 16/222,949; Examiner-Initiated Interview Summary, dated Nov. 9, 2021; 1 page.

MCT4 INHIBITORS FOR TREATING DISEASE

This application is a continuation of U.S. patent application Ser. No. 17/030,243, filed Sep. 23, 2020, which is a continuation of U.S. patent application Ser. No. 16/222,964, filed Dec. 17, 2018, which is a divisional application of U.S. patent application Ser. No. 15/180,623, filed Jun. 13, 2016, and entitled "MCT4 Inhibitors for Treating Disease," which claims the benefit of priority of U.S. provisional application No. 62/174,685, filed Jun. 12, 2015, the contents of which are incorporated by reference as if written herein in their entireties.

This invention was made with government support under grant no. R43 CA189391 awarded by the National Institutes of Health. The government has certain rights in the invention.

The present disclosure relates to new heterocyclic compounds and compositions, and their application as pharmaceuticals for the treatment of disease. Methods of inhibition of MCT4 activity in a human or animal subject are also provided for the treatment of diseases such as proliferative and inflammatory diseases.

Lactic acid export from glycolytic cells is typically mediated by the monocarboxylate transporter MCT4. MCT4 exhibits weak affinity for lactate ($K_m$=28 mM) coupled with a high turnover rate, allowing rapid export of large amounts of lactic acid. MCT4 expression is normally limited to highly glycolytic tissues such as white muscle fibers, lymphocytes, astrocytes, and Sertoli cells. Though MCT4 is absent from most normal tissues, MCT4 expression is highly upregulated, and correlates with poor survival, in many cancer indications, including colorectal cancer, glioma, head and neck cancer, triple-negative breast cancer, prostate cancer, KRAS mutant lung cancer, liver cancer, and kidney cancer.

The correlation of MCT4 expression and poor cancer outcome appears to be of significant functional consequence in multiple cancer models. Stable expression of MCT4 is highly tumorigenic in a respiration-impaired, Ras-transformed fibroblast xenograft model. Conversely, MCT4 silencing slows or ablates tumor growth in xenograft models of breast cancer, colorectal cancer, and glioma. MCT4 expression is required for inflammatory cytokine IL-8-mediated angiogenesis in breast and colon cancer xenograft models. MCT4 has also been shown to play important roles in cancer cell migration, invasion, and various aspects of the Warburg effect (e.g., proliferation on glucose, extracellular acidification, and lactate secretion).

Glycolytic reprogramming, including MCT4 upregulation, is also required for pro-inflammatory functions of innate immune cells such as macrophages and dendritic cells. The silencing of MCT4 leads to decreased inflammatory responses in macrophages. These findings suggest that MCT4 may play an important role in innate immune cell mediated inflammatory diseases.

MCT4 has also been demonstrated to be important in the glycolytic metabolism of rheumatoid arthritis (RA) synovial fibroblasts, which are highly proliferative and are one of the key players in the joint destructive process of RA. Silencing of MCT4 in RA synovial fibroblasts significantly reduces the severity of arthritis in a mouse collagen-induced arthritis model.

Inhibition of MCT4-mediated lactic acid export may be an effective strategy to impair the Warburg effect in diseases including cancer and inflammatory disease. Unfortunately, no potent and selective MCT4 inhibitors have been described. Moderate to weak MCT4 inhibitors are known (e.g., phloretin and α-CN-4-OH-cinnamate); however, these compounds promiscuously inhibit a number of other transporters, including MCT1.

Thus, there is a need for potent and selective MCT4 inhibitors for use in the treatment or prevention of proliferative and inflammatory diseases.

Accordingly, disclosed herein are new compositions and methods for inhibiting MCT4 activity.

Provided is a compound of structural Formula I

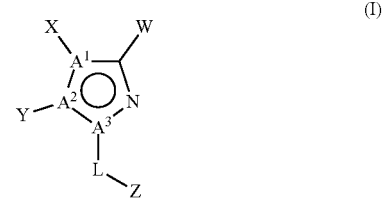

or a salt thereof, wherein:

$A^1$, $A^2$, and $A^3$ are independently chosen from N and C, wherein at least one of $A^1$, $A^2$, and $A^3$ is N;

L is chosen from a bond and methylene;

W is chosen from

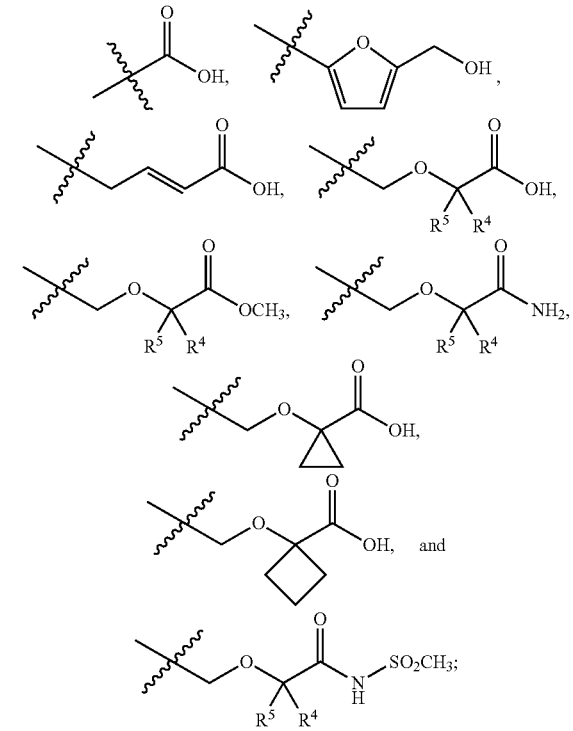

X is chosen from alkenyl, alkenylamino, alkyl, aminoalkenyl, aminoalkyl, and H, any of which may be optionally substituted with one to three $R^1$ groups, each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl;

Y is chosen from alkenyl, alkenylamino, alkyl, aminoalkenyl, aminoalkyl, aryl, cycloalkyl, and heteroaryl, any of which may be optionally substituted with one to three $R^2$ groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl, wherein
  when X is not H, X and Y together with the atoms to which they are attached may form an aryl, cycloalkyl, heteroaryl, or heterocycloalkyl ring, any of which may be optionally substituted with one to three $R^7$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl; and
  $R^4$ and $R^5$ are independently chosen from H and $C_1$-$C_6$alkyl, with $R^4$ and $R^5$ together comprising no more than 6 carbons; and
  Z is chosen from aryl and heteroaryl, either of which may be optionally substituted with one to three $R^3$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

Provided is a composition comprising a compound of Formula I and a pharmaceutically acceptable carrier, adjuvant, or vehicle.

Provided is a method for inhibiting activity of the monocarboxylate transporter MCT4, or a mutant thereof, in a biological sample comprising the step of contacting said biological sample with a compound as recited in claim 1.

Provided is a method for inhibiting activity of the monocarboxylate transporter MCT4, or a mutant thereof, activity in a patient comprising the step of administering to the patient a compound as recited in claim 1.

Provided is a method for treating a monocarboxylate transporter MCT4-mediated disorder in a subject in need thereof, comprising the step of administering to said patient a compound as recited in claim 1.

Provided is a method of treating a MCT4-mediated disorder in a subject in need thereof, comprising the sequential or co-administration of a compound of Formula I or a pharmaceutically acceptable salt thereof, and another therapeutic agent.

Provided is a compound of any of Formula I for use in human therapy.

Provided is a compound of any of Formula I for use in treating a MCT4-mediated disease.

Provided is a use of a compound of Formula I for the manufacture of a medicament to treat a MCT4-mediated disease.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "a compound as disclosed herein," when used in pharmaceutical method of treatment, medical use, method of inhibition, and similar embodiments, refers to any compound disclosed in a genus or subgenus or specifically exemplified herein.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a range close to the value. When no particular range, such as a standard deviation to a mean value given in a chart or table of data, is recited, the term "about" should be understood to mean that range which would encompass the recited value and the range which would be included by rounding up or down to that figure as well, taking into account significant figures.

As used herein, two embodiments are "mutually exclusive" when one is defined to be something which is different than the other. For example, an embodiment wherein Y is specified to be thienyl is mutually exclusive with an embodiment in which Y is specified to be phenyl. However, an embodiment wherein Y is specified to be thienyl is not mutually exclusive with an embodiment in which Z is ortho-substituted with an $R^3$ group chosen from alkoxy, alkyl, alkylamino, halo, and haloalkyl.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain saturated hydrocarbon containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower haloalkyl, lower haloalkenyl, lower haloalkynyl, lower alkoxy, lower haloalkoxy, oxo, lower cyano, hydrogen, halogen, hydroxy, amino, lower alkylamino, amido, nitro, thiol, C(O)CH$_3$, CO$_2$CH$_3$, and CO$_2$H. Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, alkylene, alkynylene, cycloalkyl, heteroalkyl, aryl, heteroaryl and heterocycloalkyl, any of which may be optionally substituted as defined herein. Unless otherwise specified, when either R or R' contains a heteroatom, they should be understood to attach to the parent group via a carbon atom. Whether an R group has a number designation or not, every R group, including R, R' and Rn where n=(1, 2, 3 . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

MCT4 inhibitor is used herein to refer to a compound that exhibits an IC50 with respect to MCT4 activity of no more than about 100 µM and more typically not more than about 50 µM, as measured in the MCT4 enzyme assay described generally herein below. IC50 is that concentration of inhibitor that reduces the activity of an enzyme (e.g., MCT4) to half-maximal level. Certain compounds disclosed herein have been discovered to exhibit inhibition against MCT4. In certain embodiments, compounds will exhibit an IC50 with respect to MCT4 of no more than about 10 µM; in further embodiments, compounds will exhibit an IC50 with respect to MCT4 of no more than about 5 µM; in yet further embodiments, compounds will exhibit an IC50 with respect to MCT4 of not more than about 1 µM; in yet further embodiments, compounds will exhibit an IC50 with respect to MCT4 of not more than about 200 nM, as measured in the MCT4 binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock (farm animals) such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Compounds

The present disclosure provides a compound of structural Formula I

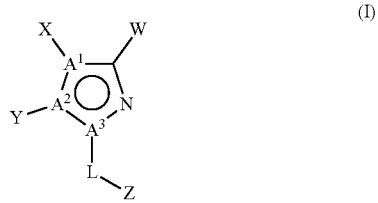

or a salt thereof, wherein:

$A^1$, $A^2$, and $A^3$ are independently chosen from N and C, wherein at least one of $A^1$, $A^2$, and $A^3$ is N;

L is chosen from a bond and methylene;

W is chosen from

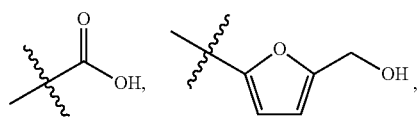

-continued

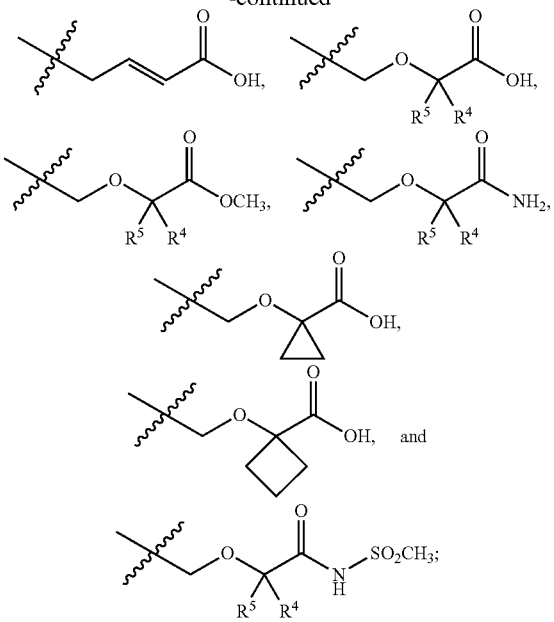

X is chosen from alkenyl, alkenylamino, alkyl, aminoalkenyl, aminoalkyl, and H, any of which may be optionally substituted with one to three $R^1$ groups, each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl;

Y is chosen from alkenyl, alkenylamino, alkyl, aminoalkenyl, aminoalkyl, aryl, cycloalkyl, and heteroaryl, any of which may be optionally substituted with one to three $R^2$ groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl, wherein when X is not H, X and Y together with the atoms to which they are attached may form an aryl, cycloalkyl, heteroaryl, or heterocycloalkyl ring, any of which may be optionally substituted with one to three $R^7$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl; and $R^4$ and $R^5$ are independently chosen from H and alkyl, with $R^4$ and $R^5$ together having no more than 6 carbons; and Z is chosen from aryl and heteroaryl, either of which may be optionally substituted with one to three $R^3$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

In certain embodiments, $A^1$ and $A^2$ are C; and $A^3$ is N.

In certain embodiments, X is hydrogen.

In certain embodiments, W is chosen from:

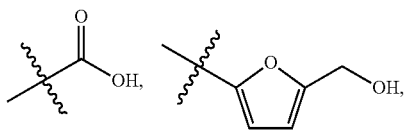

-continued

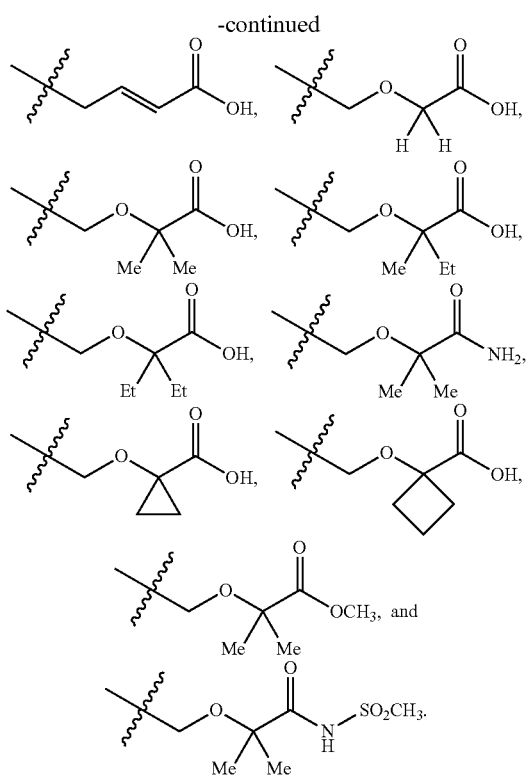

In certain embodiments, W is chosen from

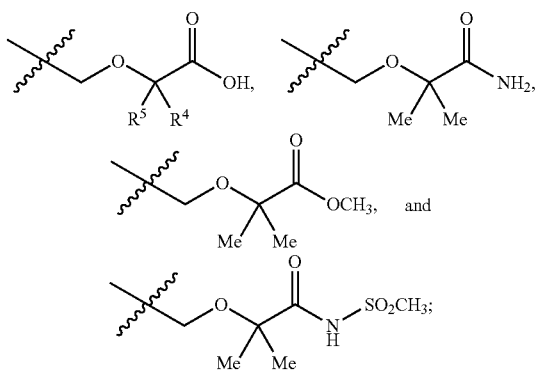

$R^4$ and $R^5$ are independently chosen from H and alkyl, with $R^4$ and $R^5$ together having no more than 6 carbons.

In certain embodiments,

X is chosen from alkenyl, alkenylamino, alkyl, aminoalkenyl, aminoalkyl, and H, any of which may be optionally substituted with one to three $R^1$ groups, each independently chosen from alkenyl, alkoxy, alkyl, aryl, halo, heteroaryl, and haloalkyl;

Y is chosen from alkenyl, alkenylamino, alkyl, aminoalkenyl, aminoalkyl, aryl, cycloalkyl, and heteroaryl, any of which may be optionally substituted with one to three $R^2$ groups each independently chosen from alkenyl, alkoxy, cycloalkoxy, cycloalkylmethoxy, haloalkoxy, alkyl, aryl, halo, heteroaryl, and haloalkyl, wherein when X is not H, X and Y together with the atoms to which they are attached may form an aryl, cycloalkyl, heteroaryl, or heterocycloalkyl ring, any of which may be optionally substituted with one to three $R^4$ groups each independently chosen from alkenyl, alkoxy, alkyl, aryl, halo, heteroaryl, and haloalkyl; and Z is chosen from aryl and heteroaryl, either of which may be optionally substituted with one to three $R^3$ groups each independently chosen from alkenyl, alkoxy, alkyl, alkylamino, aryl, halo, heteroaryl, and haloalkyl.

In certain embodiments, Z is chosen from phenyl and pyridinyl, either of which may be optionally substituted with one to three $R^3$ groups each independently chosen from alkenyl, alkoxy, alkyl, alkylamino, aryl, halo, heteroaryl, and haloalkyl.

In certain embodiments, Y is chosen from aryl and heteroaryl, any of which may be optionally substituted with one to three $R^2$ groups each independently chosen from alkenyl, alkoxy, cycloalkoxy, cycloalkylmethoxy, haloalkoxy, alkyl, aryl, halo, heteroaryl, and haloalkyl.

In certain embodiments, Y is chosen from phenyl, thienyl, and thiazolyl, any of which may be optionally substituted with one to three $R^2$ groups each independently chosen from alkoxy, cycloalkoxy, cycloalkylmethoxy, haloalkoxy, alkyl, halo, and haloalkyl.

In certain embodiments, $R^4$ and $R^5$ are chosen from the following combinations:
$R^4$ and $R^5$ are each methyl;
$R^4$ and $R^5$ are each ethyl; and
$R^4$ is methyl and $R^5$ is ethyl.

In certain embodiments, the compound has structural Formula II:

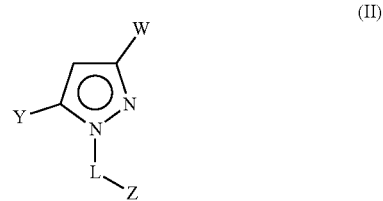

(II)

or a salt thereof, wherein:
L is chosen from a bond and methylene;
W is chosen from

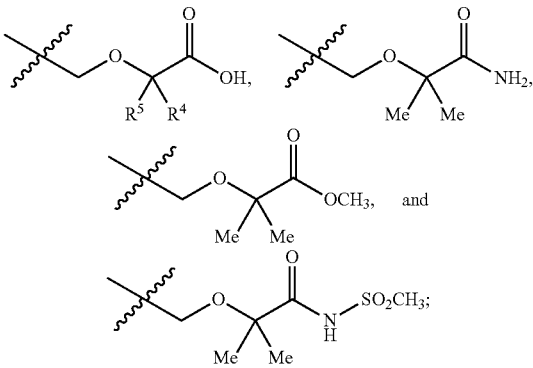

Y is chosen from aryl, cycloalkyl, and heteroaryl, any of which may be optionally substituted with one to three $R^2$ groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl;

$R^4$ and $R^5$ are independently chosen from H and alkyl, with $R^4$ and $R^5$ together having no more than 6 carbons; and Z is chosen from phenyl and pyridinyl, either of which may be optionally substituted with one to three $R^3$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

In certain embodiments,

Y is chosen from aryl, cycloalkyl, and heteroaryl, any of which may be optionally substituted with one to three $R^2$ groups each independently chosen from alkenyl, alkoxy, cycloalkoxy, cycloalkylmethoxy, haloalkoxy, alkyl, aryl, halo, heteroaryl, and haloalkyl; and Z is chosen from phenyl and pyridinyl, either of which may be optionally substituted with one to three $R^3$ groups each independently chosen from alkenyl, alkoxy, alkyl, alkylamino, aryl, halo, heteroaryl, and haloalkyl.

In certain embodiments, Z is chosen from phenyl and pyridinyl, either of which may be optionally substituted with one to three $R^3$ groups each independently chosen from alkenyl, alkoxy, alkyl, alkylamino, aryl, halo, heteroaryl, and haloalkyl.

In certain embodiments, Y is chosen from phenyl, thienyl, and thiazolyl, any of which may be optionally substituted with one to three $R^2$ groups each independently chosen from alkoxy, cycloalkoxy, cycloalkylmethoxy, haloalkoxy, alkyl, halo, and haloalkyl.

In certain embodiments, $R^4$ and $R^5$ are chosen from the following combinations:
$R^4$ and $R^5$ are each methyl;
$R^4$ and $R^5$ are each ethyl; and
$R^4$ is methyl and $R^5$ is ethyl.

In certain embodiments, the compound has structural Formula III:

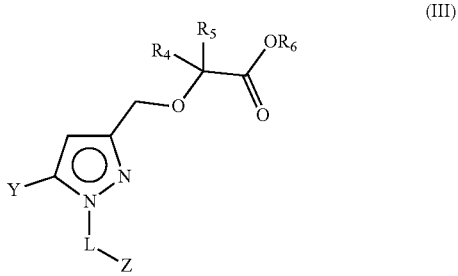

(III)

or a salt thereof, wherein:
L is chosen from a bond and methylene;
$R^4$ and $R^5$ are independently chosen from H and alkyl, with $R^4$ and $R^5$ together having no more than 6 carbons;
$R^6$ is chosen from H and methyl;
Y is chosen from aryl and heteroaryl, either of which may be optionally substituted with one to three $R^2$ groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl; and
Z is chosen from phenyl and pyridinyl, either of which may be optionally substituted with one to three $R^3$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

Also provided are stereoisomers (e.g., enantiomers and diastereomers) of compounds disclosed herein. For example, in certain embodiments, also provided are compound of structural Formula IIIa or IIIb:

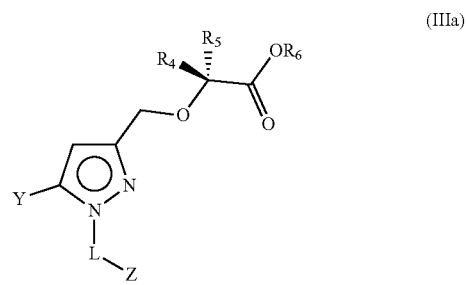

(IIIa)

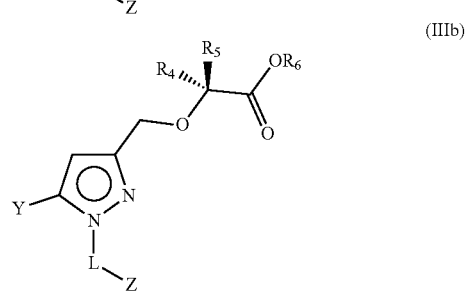

(IIIb)

or a salt thereof, wherein:
L is chosen from a bond and methylene;
$R^4$ and $R^5$ are independently chosen from H and alkyl, with $R^4$ and $R^5$ together having no more than 6 carbons;
$R^6$ is chosen from H and methyl;
Y is chosen from aryl and heteroaryl, either of which may be optionally substituted with one to three $R^2$ groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl; and
Z is chosen from phenyl and pyridinyl, either of which may be optionally substituted with one to three $R^3$ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

In certain embodiments,

Y is chosen from aryl and heteroaryl, either of which may be optionally substituted with one to three $R^2$ groups each independently chosen from alkenyl, alkoxy, cycloalkoxy, cycloalkylmethoxy, haloalkoxy, alkyl, aryl, halo, heteroaryl, and haloalkyl; and Z is chosen from phenyl and pyridinyl, either of which may be optionally substituted with one to three $R^3$ groups each independently chosen from alkenyl, alkoxy, alkyl, alkylamino, aryl, halo, heteroaryl, and haloalkyl.

In certain embodiments,

Y is chosen from aryl and heteroaryl, either of which may be optionally substituted with one to three $R^2$ groups each independently chosen from alkoxy, cycloalkoxy, cycloalkylmethoxy, haloalkoxy, alkyl, halo, and haloalkyl; and Z is chosen from phenyl and pyridinyl, either of which may be optionally substituted with one to three $R^3$ groups each independently chosen from alkoxy, alkyl, alkylamino, halo, and haloalkyl.

In certain embodiments, Y is chosen from phenyl, thienyl, and thiazolyl, any of which may be optionally substituted with one to three $R^2$ groups each independently chosen from alkoxy, cycloalkoxy, cycloalkylmethoxy, haloalkoxy, alkyl, halo, and haloalkyl.

In certain embodiments, $R^4$ and $R^5$ are chosen from the following combinations:

$R^4$ and $R^5$ are each methyl;

$R^4$ and $R^5$ are each ethyl; and $R^4$ is methyl and $R^5$ is ethyl.

In certain embodiments,

Y is phenyl, substituted with an $R^2$ group chosen from alkoxy, cycloalkoxy, cycloalkylmethoxy, haloalkoxy, alkyl, halo, and haloalkyl; and Z is phenyl, substituted with one or two $R^3$ groups chosen from alkoxy, alkyl, alkylamino, halo, and haloalkyl.

In certain embodiments, Y is meta-substituted with an $R^2$ group chosen from alkoxy, cycloalkoxy, cycloalkylmethoxy, and haloalkoxy.

In certain embodiments, Y is meta-substituted with an $R^2$ group chosen from methoxy, trifluoromethoxy, ethoxy, 2,2,2-trifluoroethoxy, isopropoxy, isobutoxy, cyclopropoxy, cyclobutoxy, cyclopentoxy, cyclopropylmethoxy, cyclobutylmethoxy, and cyclopentylmethoxy.

In certain embodiments, Z is ortho-substituted with an $R^3$ group chosen from alkoxy, alkyl, alkylamino, halo, and haloalkyl.

In certain embodiments, Z is ortho-substituted with halo.

In certain embodiments, Z is ortho-substituted with chloro.

In certain embodiments, $R^6$ is H.

In certain embodiments,

Y is thienyl, substituted with an $R^2$ group chosen from alkoxy, cycloalkoxy, cycloalkylmethoxy, haloalkoxy, alkyl, halo, and haloalkyl; and Z is phenyl, substituted with one or two $R^3$ groups chosen from alkoxy, alkyl, alkylamino, halo, and haloalkyl.

In certain embodiments, Y is substituted with an $R^2$ group chosen from alkoxy, cycloalkoxy, cycloalkylmethoxy, and haloalkoxy.

In certain embodiments, Y is substituted with an $R^2$ group chosen from methoxy, isopropoxy, isobutoxy, and cyclopropoxy.

In certain embodiments, Z is ortho-substituted with an $R^3$ group chosen from alkoxy, alkyl, alkylamino, halo, and haloalkyl.

In certain embodiments, Z is ortho-substituted with halo.

In certain embodiments, Z is ortho-substituted with chloro.

In certain embodiments, $R^6$ is H.

In certain embodiments,

Y is thiazolyl, substituted with one $R^2$ group chosen from alkoxy, cycloalkoxy, cycloalkylmethoxy, haloalkoxy, alkyl, halo, and haloalkyl; and Z is phenyl, substituted with one or two $R^3$ groups chosen from alkoxy, alkyl, alkylamino, halo, and haloalkyl.

In certain embodiments, Y is substituted with one $R^2$ group chosen from alkoxy, cycloalkoxy, cycloalkylmethoxy, and haloalkoxy.

In certain embodiments, Y is substituted with one $R^2$ group chosen from methoxy, isopropoxy, isobutoxy, and cyclopropoxy.

In certain embodiments, Z is ortho-substituted with one $R^3$ group chosen from alkoxy, alkyl, alkylamino, halo, and haloalkyl.

In certain embodiments, Z is ortho-substituted with one halo.

In certain embodiments, Z is ortho-substituted with one chloro.

In certain embodiments, $R^6$ is H.

In certain embodiments, the compound is chosen from Examples 1-82 or a salt thereof, as disclosed herein.

Also provided are embodiments wherein any of embodiment above may be combined with any one or more of these embodiments, provided the combination is not mutually exclusive.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Compounds described herein can be administered as follows:

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present invention may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Accordingly, also provided herein is a pharmaceutical composition comprising a compound as disclosed herein, or a pharmaceutically acceptable salt thereof, and a pharmaceutically acceptable carrier, adjuvant, or vehicle.

In certain embodiments, the pharmaceutical composition is formulated for oral administration. In certain embodiments, the pharmaceutical composition is formulated for parenteral administration. In certain embodiments, the pharmaceutical composition is formulated for intravenous administration.

Methods of Receptor Modulation and Treatment

The present disclosure provides compounds and pharmaceutical compositions that inhibit glutaminase activity, particularly MCT4 activity and are thus useful in the treatment or prevention of disorders associated with MCT4. Compounds and pharmaceutical compositions of the present disclosure selectively modulate MCT4 and are thus useful in the treatment or prevention of a range of disorders associated with MCT4 and include, but are not limited to, proliferative and inflammatory diseases.

Accordingly, provided herein is a method for inhibiting activity of the monocarboxylate transporter MCT4, or a mutant thereof, in a biological sample comprising the step of contacting said biological sample with a compound as disclosed herein, or a salt thereof.

Also provided herein is a method for inhibiting activity of the monocarboxylate transporter MCT4, or a mutant thereof, in a patient comprising the step of administering to the patient a compound as disclosed herein, or a salt thereof.

Also provided herein is a method for selectively inhibiting activity of the monocarboxylate transporter MCT4, or a mutant thereof, over the monocarboxylate transporter MCT1, or a mutant thereof, in a patient comprising the step of administering to the patient a compound as disclosed herein, or a salt thereof.

In certain embodiments, the inhibition is at least 100-fold selective for MCT4 over MCT1.

Cancer

In certain embodiments, the compounds and pharmaceutical compositions of the present disclosure may be useful in the treatment or prevention of cancer.

In certain embodiments, the compounds of the present disclosure may be used to prevent or treat cancer, wherein the cancer is one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia or Wilms Tumor.

In certain embodiments, the cancer to be treated is one specific to T-cells such as T-cell lymphoma and lymphoblastic T-cell leukemia.

In certain embodiments, the compounds and pharmaceutical compositions of the present disclosure may be useful in the treatment or prevention of an inflammatory disease.

In certain embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

Inflammatory Disease

In certain embodiments, the compounds and pharmaceutical compositions of the present disclosure may be useful in the treatment or prevention of inflammatory disease.

In certain embodiments, the compounds of the present disclosure may be used to prevent or treat inflammatory disease, wherein the inflammatory disease is one or a variant of acid-induced lung injury, acne (PAPA), acute respiratory distress syndrome, Addison's disease, adrenal hyperplasia, adrenocortical insufficiency, ageing, AIDS, alcoholic hepatitis, alcoholic liver disease, allergen induced asthma, allergic bronchopulmonary aspergillosis, allergic conjunctivitis, alopecia, Alzheimer's disease, amyloidosis, amyotrophic lateral sclerosis, angina pectoris, angioedema, anhidrotic ectodermal dysplasia (e.g. with immune deficiency), ankylosing spondylitis, anterior segment inflammation, antiphospholipid syndrome, aphthous stomatitis, appendicitis, asthma, atherosclerosis, atopic dermatitis, autoimmune diseases, autoimmune hepatitis, bee sting-induced inflammation, Behcet's disease, Bell's Palsy, berylliosis, Blau syndrome, bone pain, bronchiolitis, burns, bursitis, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic obstructive pulmonary disease, colitis, complex regional pain syndrome, connective tissue disease, corneal ulcer, Crohn's disease, cryopyrin-associated periodic syndromes, cryptococcosis, cystic fibrosis, deficiency of the interleukin-1-receptor antagonist, dermatitis, dermatitis endotoxemia, dermatomyositis, endometriosis, endotoxemia, epicondylitis, erythroblastopenia, familial amyloidotic polyneuropathy, familial cold urticaria, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Huntington's disease, hyaline membrane disease, hyperammonemia, hypercalcemia, hypercholesterolemia, hyperimmunoglobulinemia D with recurrent fever, hypoplastic and other anemias, idiopathic pulmonary fibrosis, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, ischemia/reperfusion, juvenile rheumatoid arthritis, keratitis, kidney disease, kidney injury caused by parasitic infections, kidney transplant rejection prophylaxis, leptospirosis, Loeffler's syndrome, lung injury, lupus, lupus nephritis, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, pertussis, perineal or peritoneal endometriosis, pharyngitis and adenitis (PFAPA syndrome), plant irritant-induced inflammation, pneumocystis infection, pneumonia, pneumonitis, poison ivy/urushiol oil-induced inflammation, polyarteritis nodosa, polychondritis, polycystic kidney disease, polymyositis, psoriasis, psychosocial stress disease, pulmonary disease, pulmonary fibrosis, pulmonary hypertension, pyoderma gangrenosum, pyogenic sterile arthritis, renal disease, retinal disease, rheumatic disease, rheumatoid arthritis, rheumatic carditis, sarcoidosis, sebborrhea, sepsis, severe pain, sickle cell, sickle cell anemia, silica-induced diseases, Sjogren's syndrome, skin diseases, sleep apnea, spinal cord injury, Stevens-Johnson syndrome, stroke, subarachnoid hemorrhage, sunburn, systemic sclerosis (scleroderma), temporal arteritis, tenosynovitis, thrombocytopenia, thyroiditis, tissue transplant, TNF receptor associated periodic syndrome (TRAPS), Toxoplasmosis, transplant, traumatic brain injury, tuberculosis, type 1 diabetes, type 2 diabetes, ulcerative colitis, urticaria, uveitis, Wegener's granulomatosis, and weight loss.

A method for treating a monocarboxylate transporter MCT4-mediated disorder in a subject in need thereof, comprising the step of administering to said patient a compound as disclosed herein, or a pharmaceutically acceptable salt thereof.

In certain embodiments, the subject is a human.

In certain embodiments, the moncarboxylate transporter MCT4-mediated disorder is chosen from an inflammatory disorder and a proliferative disorder.

In certain embodiments, the moncarboxylate transporter MCT4-mediated disorder is a proliferative disorder.

In certain embodiments, the proliferative disorder is cancer.

In certain embodiments, the cancer is chosen from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, and Wilms' tumor.

In certain embodiments, the moncarboxylate transporter MCT4-mediated disorder is an inflammatory disorder.

In certain embodiments, the inflammatory disorder is chosen from Crohn's disease, ulcerative colitis, idiopathic pulmonary fibrosis, muscular dystrophy, rheumatoid arthritis, and systemic sclerosis (scleroderma).

Also provided herein is a method of treating a monocarboxylate transporter MCT4-mediated disorder in a subject in need thereof, comprising the sequential or co-administration of a compound as disclosed herein or a pharmaceutically acceptable salt thereof, and another therapeutic agent.

In certain embodiments, the therapeutic agent is a protein kinase inhibitor.

In certain embodiments, the protein kinase inhibitor is chosen from Aurora B, EGFR, PLK-1, CDKs inhibitors.

In certain embodiments, the therapeutic agent is chosen from an antimetabolite, bcr-abl inhibitor, DNA damaging agent, EGFR inhibitor, microtubule stabilizing inhibitor, mitotic arrest inhibitor, S-phase inhibitor, and a taxane.

In certain embodiments, the therapeutic agent is a DNA damaging agent chosen from an alkylating agent, anthracycline, antimetabolite agent, crosslinking agent, DNA replication inhibitor, intercalator, microtubule disruptor, PARP inhibitor, radiomimetic agent, radiosensitizer, strand break agent, and topoisomerase II inhibitor.

In certain embodiments, the therapeutic agent is chosen from aminoglutethimide, amsacrine, anastrozole, asparaginase, barasertib, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, olaparib, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

In certain embodiments, the method further comprises administering non-chemical methods of cancer treatment.

In certain embodiments, the method further comprises administering radiation therapy.

In certain embodiments, the method further comprises administering surgery, thermoablation, focused ultrasound therapy, cryotherapy, or any combination thereof.

Also provided herein is a compound as disclosed herein, or a pharmaceutically acceptable salt thereof, for use in human therapy.

Also provided herein is a compound as disclosed herein, or a pharmaceutically acceptable salt thereof, for use in treating a monocarboxylate transporter MCT4-mediated disorder, for example as disclosed in any of the embodiments and paragraphs above pertaining to methods of treatment.

Also provided herein is the use of a compound as disclosed herein, or a pharmaceutically acceptable salt thereof, for the manufacture of a medicament to treat a monocarboxylate transporter MCT4-mediated disorder, for example as disclosed in any of the embodiments and paragraphs above pertaining to methods of treatment.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-cancer drugs, anti-proliferative drugs, and anti-inflammatory drugs.

MCT4 inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a MCT4 inhibitor compound, as described herein, in combination with another therapeutic agent. By way of example only, the therapeutic effectiveness of a MCT4 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a MCT4 inhibitor as described herein) may be administered in any order, or simultaneously. If simultaneously, the multiple therapeutic agents are optionally provided in a single, unified form, or in multiple forms (by way of example only, either as a single pill or as two separate pills).

In certain embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, In certain embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a MCT4 inhibitor is optionally used in combination with procedures that provide additional benefit to the patient. A MCT4 inhibitor and any additional therapies are optionally administered before, during or after the occurrence of a disease or condition, and the timing of administering the composition containing a MCT4 inhibitor varies in some embodiments. Thus, for example, a MCT4 inhibitor is used as a prophylactic and is administered continuously to subjects with a propensity to develop conditions or diseases in order to prevent the occurrence of the disease or condition. A MCT4 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A MCT4 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a MCT4 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) anti-metabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

Where a subject is suffering from or at risk of suffering from an inflammatory condition, a MCT4 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) non-steroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

Accordingly, also provided herein is a method of treating a monocarboxylate transporter MCT4-mediated disorder in a subject in need thereof, comprising the sequential or co-administration of a compound as disclosed herein or a pharmaceutically acceptable salt thereof, and another therapeutic agent.

In certain embodiments, the therapeutic agent is a protein kinase inhibitor.

In certain embodiments, the protein kinase inhibitor is chosen from Aurora B, EGFR, PLK-1, CDKs inhibitors.

In certain embodiments, the therapeutic agent is chosen from an antimetabolite, bcr-abl inhibitor, DNA damaging agent, EGFR inhibitor, microtubule stabilizing inhibitor, mitotic arrest inhibitor, S-phase inhibitor, and a taxane.

In certain embodiments, the therapeutic agent is a DNA damaging agent chosen from an alkylating agent, anthracycline, antimetabolite agent, crosslinking agent, DNA replication inhibitor, intercalator, microtubule disruptor, PARP inhibitor, radiomimetic agent, radiosensitizer, strand break agent, and topoisomerase II inhibitor.

In certain embodiments, the therapeutic agent is chosen from aminoglutethimide, amsacrine, anastrozole, asparaginase, barasertib, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, olaparib, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

In certain embodiments, the method further comprises administering non-chemical methods of cancer treatment.

In certain embodiments, the method further comprises administering radiation therapy.

In certain embodiments, the method further comprises administering surgery, thermoablation, focused ultrasound therapy, cryotherapy, or any combination thereof.

Compound Synthesis

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art.

List of Abbreviations $CD_3OD$=deuterated methanol; $CDCl_3$=deuterated chloroform; DCM=dichloromethane; DMF=N,N-dimethylformamide; h=hour; LAH=lithium aluminum hydride; MeOH=methanol; RT=room temperature; sat.=saturated; and THF=tetrahydrofuran.

Compounds and General Methods for Preparing Them

The following schemes can be used to practice the present invention. Additional structural groups, including but not limited to those defined elsewhere in the specification and not shown in the compounds described in the schemes can be incorporated to give various compounds disclosed herein, or intermediate compounds which can, after further manipulations using techniques known to those skilled in the art, be converted to compounds of the present invention. Examples shown below further illustrate the invention.

General Synthetic Scheme for Pyrazoles

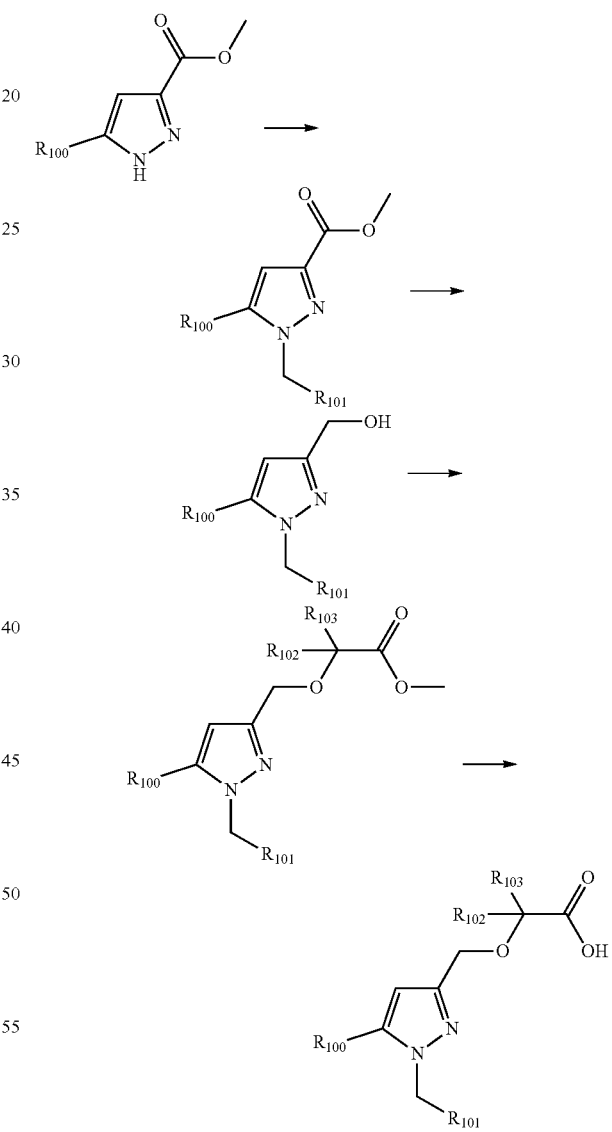

The general scheme above may be use to prepare compounds disclosed herein. In the scheme as depicted, $R_{100}$-$R_{103}$ will be understood by one of skill in the art to be any appropriate group. For example, in certain embodiments, $R_{100}$ and $R_{101}$ may be independently chosen from aryl, cycloalkyl, heterocycloalkyl, and heteroaryl, any of which may be optionally substituted. Likewise, in certain embodiments, $R_{102}$ and $R_{103}$ may be independently chosen from hydrogen, alkyl, and halogen. $R_{100}$-$R_{103}$ may also correspond to the groups defined in Formula I, II, or any other formula disclosed herein.

Synthetic Scheme for 2-[[1-[(3-chlorophenyl) methyl]-5-phenyl-pyrazol-3-yl]methoxy]-2-methyl-propanoic acid

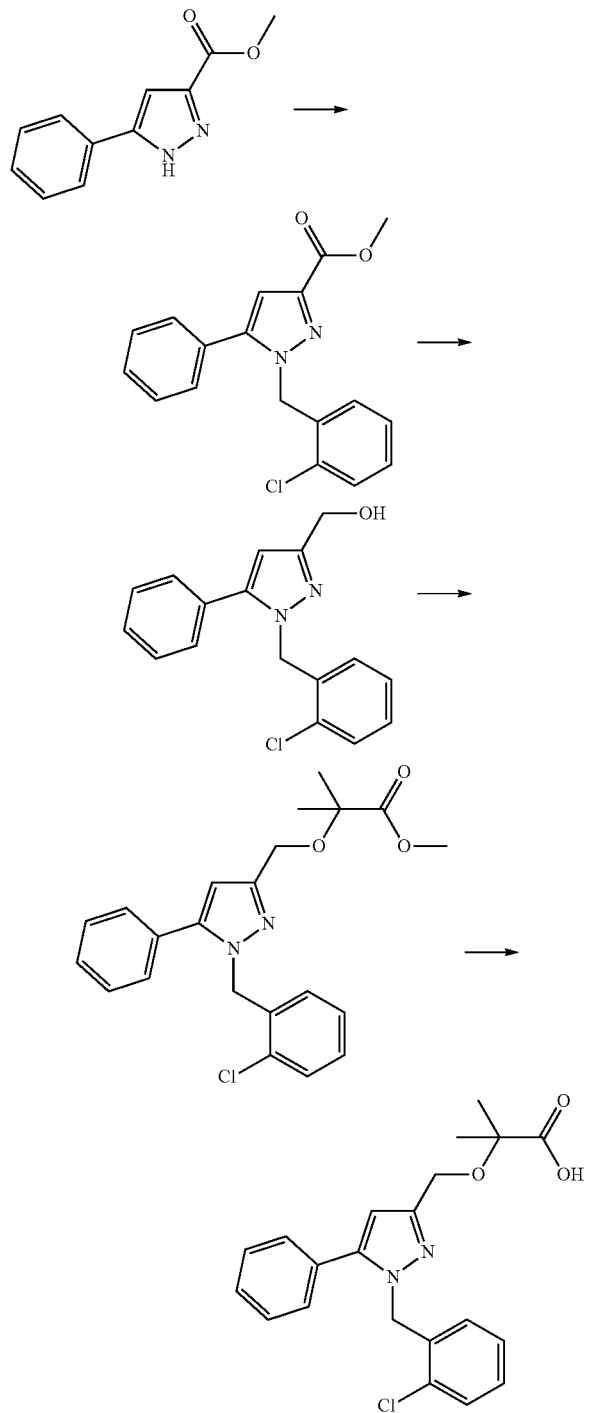

Example 1: 2-[[1-[(3-Chlorophenyl)methyl]-5-phenyl-pyrazol-3-yl]methoxy]-2-methyl-propanoic acid

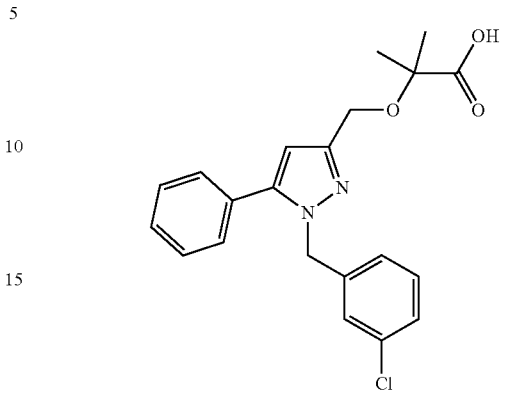

(i) Methyl 1-[(3-chlorophenyl)methyl]-5-phenyl-pyrazole-3-carboxylate. To a suspension of methyl 5-phenyl-1H-pyrazole-3-carboxylate (1) (1.0 g, 4.94 mmol) in toluene was added NaH (60%) (0.394 g, 9.88 mmol) portionwise under $N_2$ at room temperature, and stirring was continued for 30 min. To the above mixture a solution of 3-chlorobenzyl bromide (0.96 ml, 7.42 mmol) in toluene (3 mL) was added dropwise at 60° C. The reaction mixture was stirred at 110° C. for 16 h. The mixture was cooled to room temperature and quenched with aq. $NH_4Cl$ solution. The mixture was partitioned with EtOAc (100 mL) and the organic layer was separated. The EtOAc layer was washed with brine (2×25 mL) and dried over $Na_2SO_4$, and the solvent was evaporated. The residue was chromatographed over $SiO_2$ (ISCO CombiFlash® Rf200) using 0-50% gradient of EtOAc in hexane to afford title compound (1.2 g, 75%). $^1$H NMR ($CDCl_3$, 400 MHz) δ 3.95 (s, 3H), 5.36 (s, 2H), 6.85-6.92 (m, 2H), 6.95-6.99 (m, 1H), 7.17-7.29 (m, 4H). 7.35-7.48 (m, 3H).

(ii) [1-[(3-Chlorophenyl)methyl]-5-phenyl-pyrazol-3-yl]methanol. A solution of methyl 1-[(3-chlorophenyl)methyl]-5-phenyl-pyrazole-3-carboxylate (0.80 g, 2.45 mmol) in anhydrous THF was cooled to 0° C. To the above mixture LAH (0.14 g, 3.67 mmol) was added portionwise, and stirring was continued at 0° C. for 1.30 h. The mixture was quenched with water (0.15 mL) and 30% aq. NaOH solution (0.3 mL) at 0° C., and stirring was continued for 30 min. The reaction mixture was filtered, the filter cake was washed with THF (2×10 mL), and the filtrates were combined and evaporated to dryness. The residue was chromatographed over $SiO_2$ (ISCO CombiFlash® Rf 200) using 0-40% gradient of EtOAc in DCM to afford the title product (0.58 g 79%). $^1$H NMR ($CDCl_3$, 400 MHz) δ 4.64-4.81 (d, 2H), 5.31 (s, 2H), 6.35 (s, 1H), 6.86-6.94 (m, 1H), 6.98-7.05 (m, 1H), 7.19-7.23 (m, 2H), 7.26-7.35 (m, 2H), 7.39-7.46 (m 3H).

(iii) Methyl 2-[[1-[(3-chlorophenyl)methyl]-5-phenyl-pyrazol-3-yl]methoxy]-2-methyl-propanoate. To a solution of [1-[(3-chlorophenyl)methyl]-5-phenyl-pyrazol-3-yl] methanol (0.288 g, 0.964 mmol) DMF was added NaH (60%) (0.077 g, 1.93 mmol) portionwise under $N_2$ at room temperature, and stirring was continued for 30 min. The mixture was cooled to 0° C. and methyl 2-bromo-2-methyl-propanoate (0.16 mL, 1.25 mmol) was added dropwise followed by NaI (0.143 g, 0.964 mmol). The reaction mixture was warmed to room temperature gradually and stirred overnight. At the end of this period aq. $NH_4Cl$ solution was added, and the mixture was partitioned with EtOAc (40 mL). The aqueous layer was extracted with EtOAc (2×20 mL). The combined EtOAc layers were washed with brine and dried over Na$_2$SO$_4$, and the solvent was evaporated. The residue was chromatographed over SiO$_2$ (ISCO CombiFlash® Rf 200) using 0-50% gradient of EtOAc in hexanes to afford the title product as an oil (0.068 g, 38%). $^1$H NMR (CDCl$_3$, 400 MHz): δ 1.56 (s, 6H). 3.68 (s, 3H), 4.58 (s, 2H), 5.25 (s, 2H), 6.45 (s, 1H), 6.87-6.93 (m, 1H), 7.00 (s, 1H), 7.16-7.22 (m, 2H), 7.26-7.34 (m, 2H), 7.34-7.42 (m, 3H).

(iv) 2-[[1-[(3-Chlorophenyl)methyl]-5-phenyl-pyrazol-3-yl]methoxy]-2-methyl-propanoic acid. To a solution of 2-[[1-[(3-chlorophenyl)methyl]-5-phenyl-pyrazol-3-yl]-methoxy]-2-methyl-propanoate (0.068 g, 0.170 mmol) in a mixture of THF, MeOH, H$_2$O (2:1:1) (8 mL) was added lithium hydroxide monohydrate (0.035 g, 0.85 mmol) at RT and stirring was continued for further 3 h. At the end of this period the solvent was evaporated and to the residue water (2 mL) was added and acidified with 1M citric acid. The mixture was partitioned with EtOAc (25 mL) and washed with water (10 mL) followed by brine (10 mL). The EtOAc layer was dried over Na$_2$SO$_4$, and solvent was removed by evaporation. The crude product was chromatographed over SiO$_2$ (ISCO CombiFlash® Rf 200) using 0-30% gradient of MeOH in DCM to afford the title product as white solid (0.032 g). $^1$HNMR (CDCl$_3$): δ 1.56 (s, 6H), 4.61 (s, 2H), 5.34 (s, 2H), 6.38 (s, 1H), 6.87-6.97 (m, 1H), 7.04 (s, 1H), 7.18-7.24 (m, 2H), 7.26-7.35 (m, 2H), 7.35-7.45 (m, 3H).

Examples 2-50 were prepared analogously as described in Example 1.

TABLE 1

| Example # | Structure | IUPAC Name and Analytical data |
|---|---|---|
| 2 | 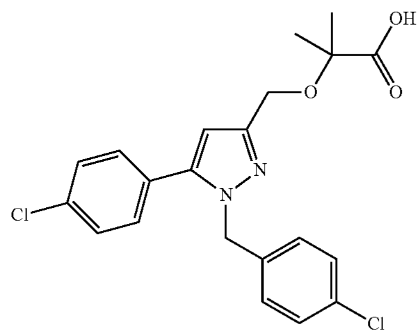 [SMILES: CC(C)(OCc1cc(-c2ccc(Cl)cc2)n(Cc2ccc(Cl)cc2)n1)C(=O)O] | 2-[[5-(4-Chlorophenyl)-1-[(4-chlorophenyl)methyl]pyrazol-3-yl]methoxy]-2-methyl-propanoic acid<br>$^1$H NMR (CD$_3$OD, 400 MHz) δ 1.52 (s, 6H), 4.54 (s, 2H0, 5.329 s, 2H), 6.48 (s, 1H), 6.91-7.00 (m, 1H), 7.21-7.30- (m, 2H), 7.31-7.38 (m, 2H), 7.40-7.48 (m 3H). |
| 3 | 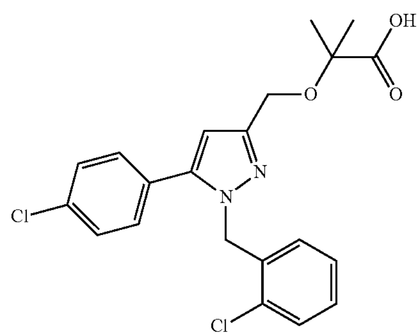 [SMILES: CC(C)(OCc1cc(-c2ccc(Cl)cc2)n(Cc2ccccc2Cl)n1)C(=O)O] | 2-[[5-(4-Chlorophenyl)-1-[(2-chlorophenyl)methyl]pyrazol-3-yl]methoxy]-2-methyl-propanoic acid<br>$^1$H NMR (CD$_3$OD, 400 MHz) δ 1.50 (s, 6H), 4.58 (s, 2H), 5.41 (s, 2H), 6.56 (s, 1H), 6.72-6.80 (m, 1H), 7.20-7.34 (m, 2H), 7.34-50 (m, 5H). |
| 4 | 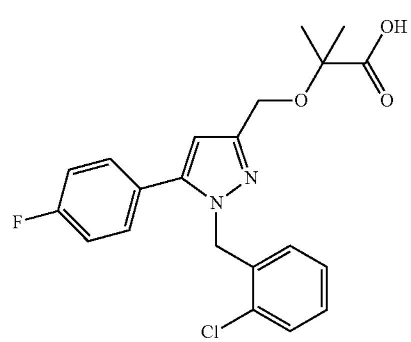 [SMILES: CC(C)(OCc1cc(-c2ccc(F)cc2)n(Cc2ccccc2Cl)n1)C(=O)O] | 2-[[1-[(2-Chlorophenyl)methyl]-5-(4-fluorophenyl)pyrazol-3-yl]methoxy]-2-methyl-propanoic acid<br>$^1$H NMR (CD$_3$OD, 400 MHz) δ 1.51 (s, 6H), 4.58 (s, 2H), 5.40 (s, 2H), 6.55 (s, 1H), 6.70-6.78 (m, 1H), 7.14-7.18 (m, 2H), 7.20-7.29 (m, 2H), 7.32-7.40 (m, 3H). |

TABLE 1-continued

| Example # | Structure | IUPAC Name and Analytical data |
|---|---|---|
| 5 | 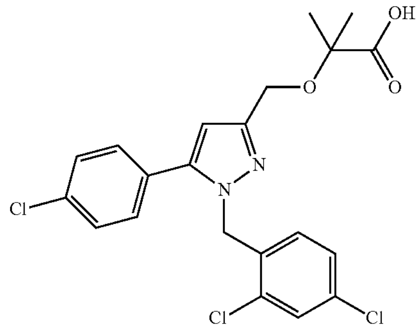 [SMILES: CC(C)(OCc1cc(-c2ccc(Cl)cc2)n(Cc2ccc(Cl)cc2Cl)n1)C(=O)O] | 2-[[5-(4-Chlorophenyl)-1-[(2,4-dichlorophenyl)methyl]pyrazol-3-yl]methoxy]-2-methyl-propanoic acid<br>$^1$H NMR (CD$_3$OD, 400 MHz) δ 1.48 (s, 6H), 4.58 (s, 2H), 5.40 (s, 2H), 6.54 (s, 1H), 6.73 (d, 1H), 7.20-7.38 (m, 3H), 7.40-48 (m, 3H). |
| 6 | 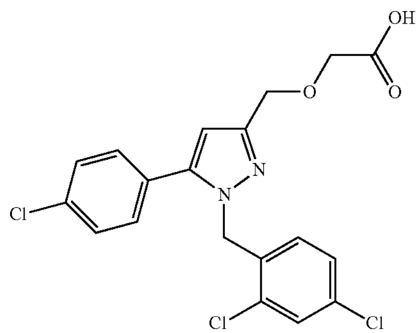 [SMILES: O=C(O)COCc1cc(-c2ccc(Cl)cc2)n(Cc2ccc(Cl)cc2Cl)n1] | 2-[[5-(4-Chlorophenyl)-1-[(2,4-dichlorophenyl)methyl]pyrazol-3-yl]methoxy]acetic acid<br>$^1$H NMR (DMSO-d$_6$, 400 MHz) δ 3.80 (s, 2H), 4.50 9s, 2H), 5.30 (s, 2H), 6.50 (s, 1H), 6.60-80 (m, 1H), 7.20-70 (m, 6H). |
| 7 | 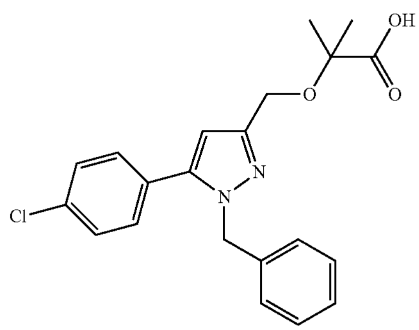 [SMILES: CC(C)(OCc1cc(-c2ccc(Cl)cc2)n(Cc2ccccc2)n1)C(=O)O] | 2-[[1-Benzyl-5-(4-Chlorophenyl)pyrazol-3-yl]methoxy]-2-methyl-propanoic acid<br>$^1$H NMR (CD$_3$OD, 400 MHz) δ 1.53 (s, 6H), 4.58 (s, 2H), 5.38 (s, 2H), 6.51 (s, 1H), 6.90 (d, 2H), 7.18-7.50 (m, 7H). |
| 8 | 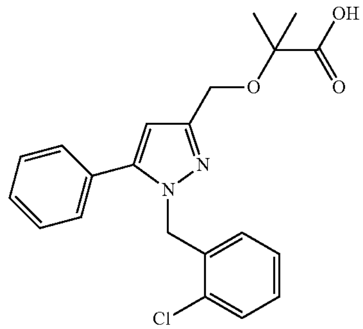 [SMILES: CC(C)(OCc1cc(-c2ccccc2)n(Cc2ccccc2Cl)n1)C(=O)O] | 2-[[1-[(2-Chlorophenyl)methyl]-5-phenyl-pyrazol-3-yl]methoxy]-2-methyl-propanoic acid<br>$^1$H NMR (DMSO-d$_6$, 400 MHz) δ 1.56 (s, 6H), 4.58 (s, 2H), 5.41 (s, 2H), 6.56 (s, 1H), 6.75-6.78 (m, 1H), 7.20-7.30 (m, 4H), 7.32-7.43 (m, 4H).<br>1H NMR (CD3OD, 400 MHz) δ 1.54 (s, 6H), 4.589s, 2H), 5.40 (s, 2H), 6.55 (s, 1H), 6.68-6.74 (m, 1H), 7.20-7.42 (m, 8H). |

TABLE 1-continued

| Example # | Structure | IUPAC Name and Analytical data |
|---|---|---|
| 9 | 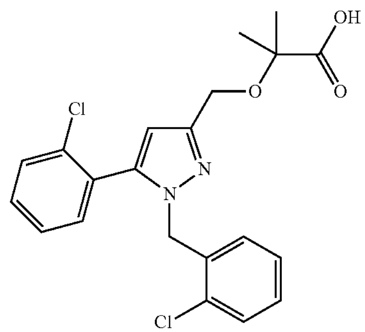 [SMILES: CC(C)(OCc1cc(-c2ccccc2Cl)n(Cc2ccccc2Cl)n1)C(=O)O] | 2-[[5-(2-Chlorophenyl)-1-[(2-chlorophenyl)methyl]pyrazol-3-yl]methoxy]-2-methyl-propanoic acid<br>$^1$H NMR (CD$_3$OD, 400 MHz) δ 1.53 (s, 6H), 4.58 (s, 2H), 5.28 (s, 2H), 6.43 (s, 1H), 6.78-7.81 (m, 1H), 7.16-34 (m, 5H), 7.38-7.42 (m, 1H), 7.50-7.56 (m, 1H). |
| 10 | 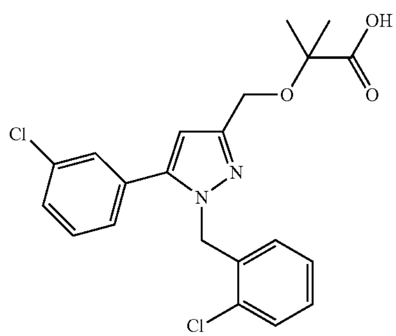 [SMILES: CC(C)(OCc1cc(-c2cccc(Cl)c2)n(Cc2ccccc2Cl)n1)C(=O)O] | 2-[[5-(3-Chlorophenyl)-1-[(2-chlorophenyl)methyl]pyrazol-3-yl]methoxy]-2-methyl-propanoic acid<br>$^1$H NMR (CD$_3$OD, 400 MHz) δ 1.32 (S, 6h) 4.58 (s, 2H), 5.42 (s, 2H), 6.57 (s, 1H), 6.67-6.80 (m, 1H), 7.22-7.30 (m, 3H), 7.32-42 (m, 4H). |
| 11 | 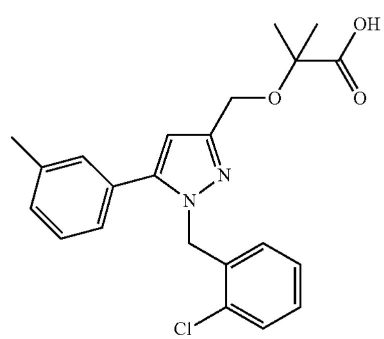 [SMILES: Cc1cccc(-c2cc(COC(C)(C)C(=O)O)nn2Cc2ccccc2Cl)c1] | 2-[[1-[(2-Chlorophenyl)methyl]-5-(m-tolyl)pyrazol-3-yl]methoxy]-2-methyl-propanoic acid<br>$^1$H NMR (CDCl$_3$, 400 MHz) δ 1.58 (s, 6H), 2.35 (s, 3H), 4.61 (s, 2H), 5.42 (s, 2H), 6.39 (s, 1H), 6.75-6.84 (m, 1H), 7.00-7.12 (m, 2H), 7.18-7.29 (4H), 7.29-7.38 (m, 1H). |
| 12 | 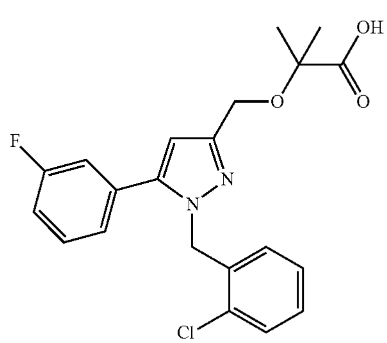 [SMILES: CC(C)(OCc1cc(-c2cccc(F)c2)n(Cc2ccccc2Cl)n1)C(=O)O] | 2-[[1-[(2-Chlorophenyl)methyl]-5-(3-fluorophenyl)pyrazol-3-yl]methoxy]-2-methyl-propanoic acid<br>$^1$H NMR (CDCl$_3$, 400 MHz) δ 1.58 (s, 6H), 4.64 (s, 2H), 5.48 (s, 2H), 6.42 (s, 1H), 6.72-6.85 (m, 1H), 6.88-7.14 (m, 3H), 7.14-7.40 (m, 4H). |

TABLE 1-continued

| Example # | Structure | IUPAC Name and Analytical data |
|---|---|---|
| 13 | 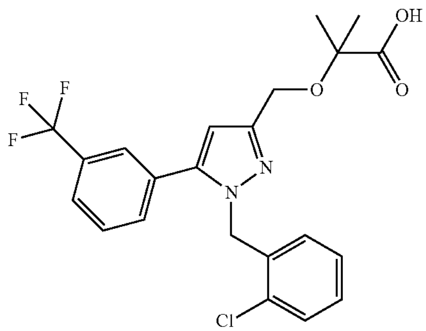 [SMILES: CC(C)(OCc1cc(-c2cccc(C(F)(F)F)c2)n(Cc2ccccc2Cl)n1)C(=O)O] | 2-[[1-[(2-Chlorophenyl)methyl]-5-[3-(trifluoromethyl)phenyl]pyrazol-3-yl]methoxy]-2-methyl-propanoic acid<br>¹H NMR (CDCl₃, 400 MHz) δ 1.58 (s, 6H), 4.62 (s, 2H), 5.41 (s, 2H), 6.46 (s, 1H), 6.80-6.88 (m, 1H), 7.17-7.24 (m, 2H), 7.29-7.38 (m, 1H), 7.39-7.47 (m, 1H), 7.49-7.54 (m, 2H), 7.59-7.68 (m, 1H). |
| 14 | 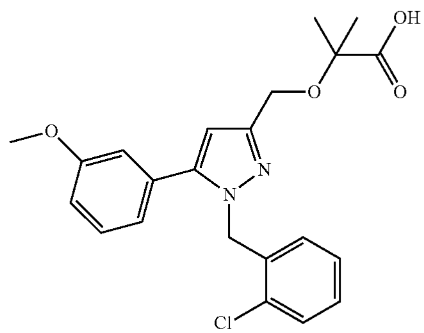 [SMILES: COc1cccc(-c2cc(COC(C)(C)C(=O)O)nn2Cc2ccccc2Cl)c1] | 2-[[1-[(2-Chlorophenyl)methyl]-5-(3-methoxyphenyl)pyrazol-3-yl]methoxy]-2-methyl-propanoic acid<br>¹H NMR (CDCl₃, 400 MHz) δ 1.58 (s, 6H), 3.68 (s, 3H), 4.62 (s, 2H), 5.46 (s, 2H), 6.42 (s, 1H), 6.74-6.81 (m, 2H), 6.82-6.88 (m, 1H), 6.89-6.94 (m, 1H), 7.15-7023 (m, 2H), 7.26-7.37 (m, 2H). |
| 15 | 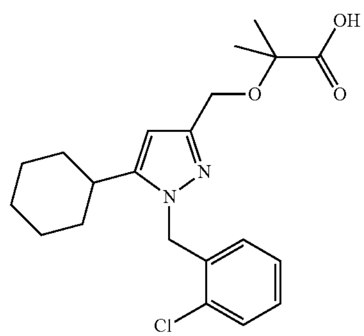 [SMILES: CC(C)(OCc1cc(C2CCCCC2)n(Cc2ccccc2Cl)n1)C(=O)O] | 2-[[1-[(2-Chlorophenyl)methyl]-5-cyclohexyl-pyrazol-3-yl]methoxy]-2-methyl-propanoic acid<br>¹H NMR (CDCl₃, 400 MHz) δ 1.16-1.42 (m, 4H), 1.54 (s, 6H), 1.57-1.81 (m, 5H), 2.36-2051 (m, 1H), 2.76-2.91 (m, 1H), 4.56 (s, 2H), 5.39 (s, 2H), 6.15 (s, 1H), 6.54-6.68 (m, 1H), 7.08-7.25 (m, 2H), 7.31-7.44 (m, 1H). |
| 16 | 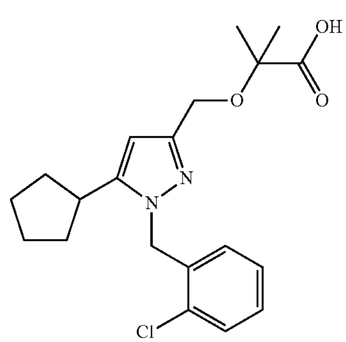 [SMILES: CC(C)(OCc1cc(C2CCCC2)n(Cc2ccccc2Cl)n1)C(=O)O] | 2-[[1-[(2-Chlorophenyl)methyl]-5-cyclopentyl-pyrazol-3-yl]methoxy]-2-methyl-propanoic acid<br>¹H NMR (CDCl₃, 400 MHz) δ 1.22-1.64 (m, 10H), 1.64-1.80 (m, 2H), 1.82-2.00 (m, 2H), 2.80-2.92 (m, 1H), 4.74 (s, 2H), 5.40 (s, 2H), 6.10 (s, 1H), 6.58-6.62 (m, 1H), 7.10-7.22 (m, 2H), 7.38 (d, 1H). |

TABLE 1-continued

| Example # | Structure | IUPAC Name and Analytical data |
|---|---|---|
| 17 | 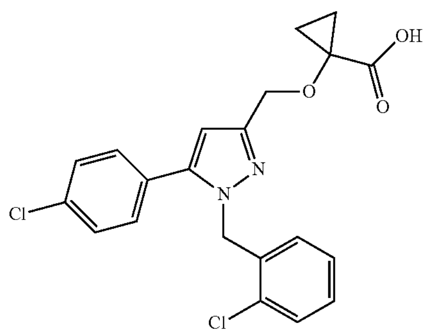 [SMILES: O=C(O)C1(OCc2cc(-c3ccc(Cl)cc3)n(Cc3ccccc3Cl)n2)CC1] | 1-[[5-(4-Chlorophenyl)-1-[(2-chlorophenyl)methyl]pyrazol-3-yl]methoxy]cyclopropanecarboxylic acid<br>$^1$H NMR (CD$_3$OD, 400 MHz) δ 1.18-1.32 (m, 3H), 1.64-1.80 (m, 1H), 4.61 (s, 2H), 5.42 (s, 2H), 6.52 (s, 1H), 6.60-6.80 (m, 1H), 7.20-52 (m, 7H). |
| 18 | 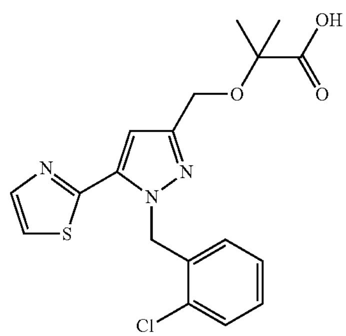 [SMILES: CC(C)(OCc1cc(-c2nccs2)n(Cc2ccccc2Cl)n1)C(=O)O] | 2-[[1-[(2-Chlorophenyl)methyl]-5-thiazol-2-yl-pyrazol-3-yl]methoxy]-2-methyl-propanoic acid<br>$^1$H NMR (CDCl$_3$, 400 MHz) δ 1.38 (m, 6H), 4.48 (s, 2H), 5.61 (s, 2H), 6.55-6.65 (m, 1H), 7.03 (s, 1H), 7.09-7.16 (m, 1H), 7.17-7.23 (m, 1H), 7.27-7.33 (d, 1H), 7.34-7.42 (m, 1H), 7.88-7.96 (d, 1H). |
| 19 | 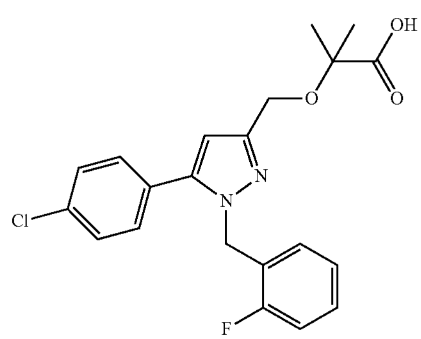 [SMILES: CC(C)(OCc1cc(-c2ccc(Cl)cc2)n(Cc2ccccc2F)n1)C(=O)O] | 2-[[5-(4-Chlorophenyl)-1-[(2-fluorophenyl)methyl]pyrazol-3-yl]methoxy]-2-methyl-propanoic acid<br>$^1$H NMR (CD$_3$OD, 400 MHz) δ 1.48 (s, 6H), 4.53 (s, 2H) 5.38 (s, 2H), 6.50 (s, 1H), 6.81-6.92 (m 1H), 7.00-7.13 (m, 2H), 7.21-7.31 (m 1H), 7.34-7.48 (m 4H) |
| 20 | 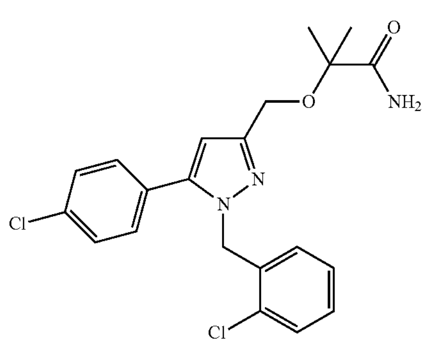 [SMILES: CC(C)(OCc1cc(-c2ccc(Cl)cc2)n(Cc2ccccc2Cl)n1)C(N)=O] | 2-[[5-(4-Chlorophenyl)-1-[(2-chlorophenyl)methyl]pyrazol-3-yl]methoxy]-2-methyl-propanamide<br>$^1$H NMR (CD$_3$OD 400 MHz) δ 1.46 (s, 6H), 4.58 (s, 2H), 5.40 (s, 2H), 6.52 (s, 1H), 6.71-6.76 (m, 1H), 7.20-7.58 (m, 6H) |

TABLE 1-continued

| Example # | Structure | IUPAC Name and Analytical data |
|---|---|---|
| 21 | 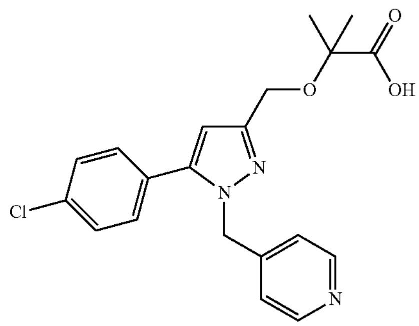 [SMILES: CC(C)(OCc1cc(-c2ccc(Cl)cc2)n(Cc2ccncc2)n1)C(=O)O] | 2-[[5-(4-chlorophenyl)-1-(4-pyridylmethyl)pyrazol-3-yl]methoxy]-2-methyl-propanoic acid<br>$^1$H NMR (CD$_3$OD 400 MHz) δ 1.52 (s, 6H), 4.58 (s, 2H), 5.56 (s, 2H), 6.59 (s, 1H), 7.21-7.52 (m, 6H), 8.50 (bs, 2H) |
| 22 | 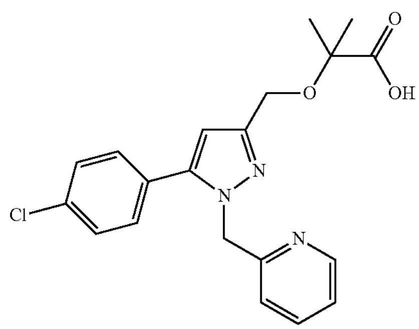 [SMILES: CC(C)(OCc1cc(-c2ccc(Cl)cc2)n(Cc2ccccn2)n1)C(=O)O] | 2-[[5-(4-Chlorophenyl)-1-(2-pyridylmethyl)pyrazol-3-yl]methoxy]-2-methyl-propanoic acid<br>$^1$H NMR (DMSO-d$_6$, 400 MHz) δ 1.38 (s, 6H), 4.40 (s, 2H), 5.38 (s, 2H), 6.41 (s, 1H), 6.90-7.10 (m, 1H), 7.20-7.85 (m, 6H), 8.51 (bs, 1H) |
| 23 | 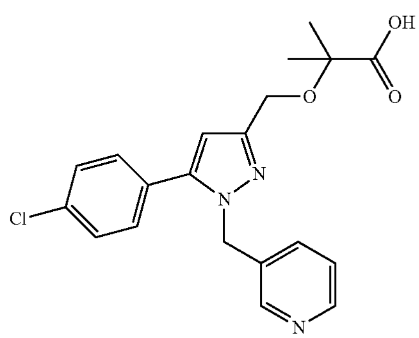 [SMILES: CC(C)(OCc1cc(-c2ccc(Cl)cc2)n(Cc2cccnc2)n1)C(=O)O] | 2-[[5-(4-Chlorophenyl)-1-(3-pyridylmethyl)pyrazol-3-yl]methoxy]-2-methyl-propanoic acid<br>$^1$H NMR (CD$_3$OD 400 MHz) δ 1.52 (s, 6H), 4.58 (s, 2H), 5.10 (s, 2H), 6.55 (s, 1H), 7.30-7.41 (m, 3H), 7.42-7.51 (m, 3H), 8.19 (s, 1H), 8.41 (d, 1H). |
| 24 | 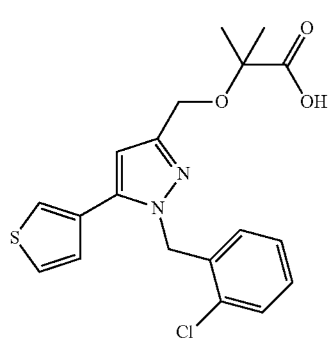 [SMILES: CC(C)(OCc1cc(-c2ccsc2)n(Cc2ccccc2Cl)n1)C(=O)O] | 2-[[1-[(2-Chlorophenyl)methyl]-5-(3-thienyl)pyrazol-3-yl]methoxy]-2-methyl-propanoic acid.<br>$^1$HNMR (CDCl$_3$): δ 1.37 (s, 6H), 4.38 (s, 2H), 5.43 (s, 2H), 6.48 (s, 1H), 6.62-6.64 (m, 1H), 7.17-7.31 (m, 3H), 7.44-7.46 (m, 1H), 7.57-7.64 (m, 2H). |

TABLE 1-continued

| Example # | Structure | IUPAC Name and Analytical data |
|---|---|---|
| 25 | 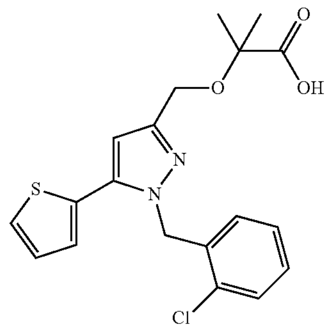 [SMILES: CC(C)(OCc1cc(-c2cccs2)n(Cc2ccccc2Cl)n1)C(=O)O] | 2-[[1-[(2-Chlorophenyl)methyl]-5-(2-thienyl)pyrazol-3-yl]methoxy]-2-methyl-propanoic acid.<br>$^1$HNMR (CDCl$_3$): δ 1.37 (s, 6H), 4.39 (s, 2H), 5.47 (s, 2H), 6.53 (s, 1H), 6.59-6.61 (m, 1H), 7.09-7.14 (m, 2H), 7.24-7.31 (m, 2H), 7.45-7.47 (m, 1H), 7.62-7.64 (m, 1H). |
| 26 | 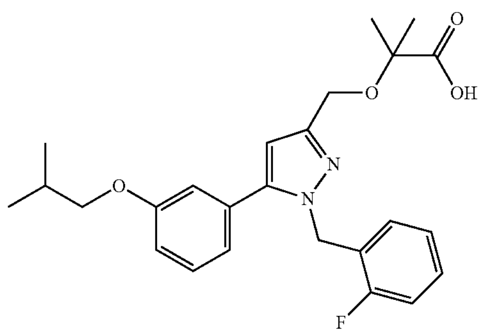 | 2-[[1-[(2-Fluorophenyl)methyl]-5-(3-isobutoxyphenyl)pyrazol-3-yl]methoxy]-2-methyl-propanoic acid<br>$^1$HNMR (CDCl$_3$): δ 0.97 (s, 3H), 0.99 (s, 3H), 1.55 (s, 6H), 2.00-2.06 (m, 1H), 3.70 (d, 2H), 4.62 (s, 2H), 5.39 (s, 2H), 6.37 (s, 1H), 6.79-6.80 (m, 1H), 6.87-7.09 (M, 5H), 7.22-7.30 (m, 2H) |
| 27 | 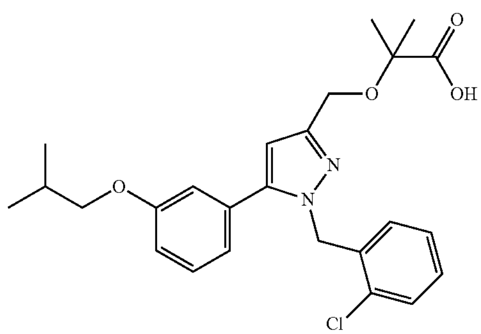 [SMILES: CC(C)COc1cccc(-c2cc(COC(C)(C)C(=O)O)nn2Cc2ccccc2Cl)c1] | 2-[[1-[(2-Chlorophenyl)methyl]-5-(3-isobutoxyphenyl)pyrazol-3-yl]methoxy]-2-methyl-propanoic acid.<br>$^1$HNMR (CDCl$_3$): δ 0.95 (s, 3H) (, 0.96 (s, 3H), 1.56 (s, 6H), 1.97-2.03 (m, 1H), 3.49 (d, 2H), 4.63 (s, 2H), 5.43 (s, 2H), 6.41 (s, 1H), 6.73-6.80 (m, 2H), 6.84-6.92 (m, 2H), 7.19-7.28 (m, 3H), 7.33-7.35 (m, 1H). |
| 28 | 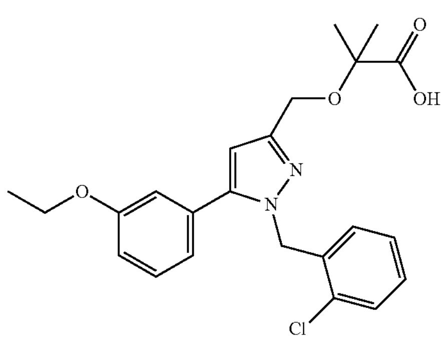 [SMILES: CCOc1cccc(-c2cc(COC(C)(C)C(=O)O)nn2Cc2ccccc2Cl)c1] | 2-[[1-[(2-Chlorophenyl)methyl]-5-(3-ethoxyphenyl)pyrazol-3-yl]methoxy]-2-methyl-propanoic acid.<br>$^1$HNMR (CDCl$_3$): δ 1.34 (t, 3H),, 1.56 (s, 6H), 3.86 (q, 2H), 4.62 (s, 2H), 5.43 (s, 2H), 6.40 (s, 1H), 6.76-6.78 (m, 2H), 6.83-6.85 (m, 1H), 6.89-6.91 (m, 1H), 7.19-7.28 (m, 3H), 7.33-7.35 (m, 1H). |

TABLE 1-continued

| Example # | Structure | IUPAC Name and Analytical data |
|---|---|---|
| 29 | 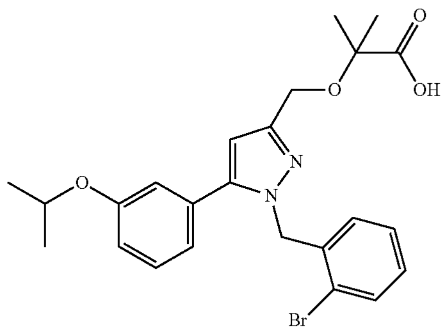 [SMILES: CC(C)Oc1cccc(-c2cc(COC(C)(C)C(=O)O)nn2Cc2ccccc2Br)c1] | 2-[[1-[(2-Bromophenyl)methyl]-5-(3-isopropoxyphenyl)pyrazol-3-yl]methoxy]-2-methyl-propanoic acid.<br>$^1$HNMR (CDCl$_3$): δ 1.21 (s, 3H), 1.23 (s, 3H), 4.28-4.32 (m, 1H), 4.62 (s, 2H), 5.39 (s, 2H). 6.42 (s, 1H), 6.71-6.74 (m, 2H), 6.82-6.89 (m, 2H), 7.11-7.15 (m, 1H), 7.22-7.27 (m, 2H), 7.51-7.54 (m, 1H). |
| 30 | 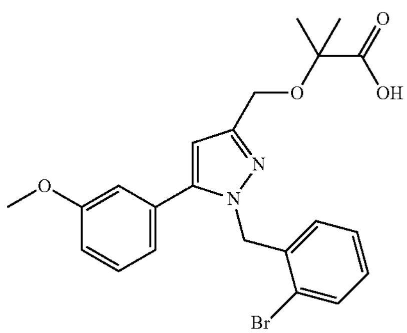 [SMILES: COc1cccc(-c2cc(COC(C)(C)C(=O)O)nn2Cc2ccccc2Br)c1] | 2-[[1-[(2-Bromophenyl)methyl]-5-(3-methoxyphenyl)-1H-pyrazol-3-yl]methoxy]-2-methylpropanoic acid<br>$^1$HNMR (CDCl$_3$): δ 1.56 (s, 6H), 3.65 (s, 3H), 4.62 (s, 2H), 5.39 (s, 2H), 6.41 (s, 1H), 6.73-6.76 (m 2H), 6.84-6.92 (m, 2H), 7.15 (t, 1H), 7.13-7.29 (m, 2H), 7.52-7.54 (m, 1H). |
| 31 | 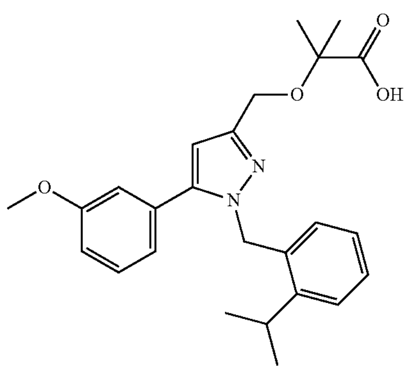 [SMILES: COc1cccc(-c2cc(COC(C)(C)C(=O)O)nn2Cc2ccccc2C(C)C)c1] | 2-[[1-[(2-Isopropylphenyl)methyl]-5-(3-methoxyphenyl)pyrazol-3-yl]methoxy]-2-methyl-propanoic acid.<br>$^1$HNMR (CDCl$_3$): δ 1.13 (s, 3H), 1.15 (s, 3H), 1.55 (s 6H), 2.94-2.97 (m, 1H), 3.62 (s, 3H), 4.63 (s, 2H), 5.42 (s, 2H), 6.39 (s, 1H), 6.65-6.67 (m, 1H), 6.75-6.76 (m, 1H), 6.85-6.91 (m, 2H), 7.07-7.11 (m, 1H), 7.21-7.28 (m, 3H) |
| 32 | 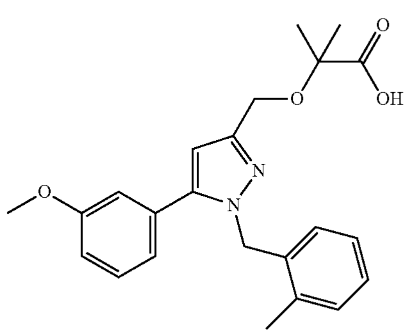 [SMILES: COc1cccc(-c2cc(COC(C)(C)C(=O)O)nn2Cc2ccccc2C)c1] | 2-[[5-(3-Methoxyphenyl)-1-(o-tolylmethyl)pyrazol-3-yl]methoxy]-2-methyl-propanoic acid.<br>$^1$HNMR (CDCl$_3$): δ 1.55 (s, 6H), 2.18 (s, 3H), 3.64 (s, 3H), 4.62 9s, 2H), 5.31 (s, 2H), 6.38 (s, 1H), 6.69-6.31 (m, 1H), 6.77-6.78 (m, 1H), 6.86-6.92 (m, 2H), 7.10-7.15 (m, 3H), 7.25-7.29 (m, 1H). |

TABLE 1-continued

| Example # | Structure | IUPAC Name and Analytical data |
|---|---|---|
| 33 | 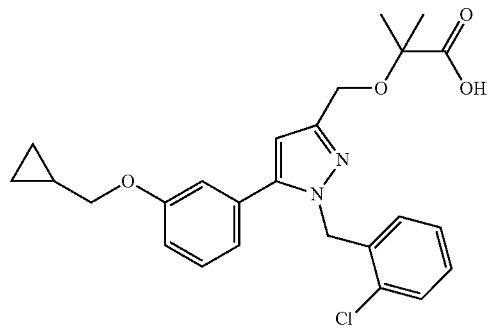 [SMILES: CC(C)(OCc1cc(-c2cccc(OCC3CC3)c2)n(Cc2ccccc2Cl)n1)C(=O)O] | 2-[[1-[(2-Chlorophenyl)methyl]-5-[3-(cyclopropylmethoxy)phenyl]pyrazol-3-yl]methoxy]-2-methyl-propanoic acid. <br> $^1$HNMR (CDCl$_3$): δ 0.25-0.29 (m, 2H), 0.58-0.63 (m, 2H), 14.16-1.20 (m, 1H), 1.55 (s, 6H), 5.58 (d, 2H), 4.63 (s, 2H), 5.42 (s, 2H), 6.40 (s, 1H), 6.374-6.78 (m, 2H), 6.84-6.93 (m, 2H), 7.18-7.28 (m, 3H), 7.33-7.35 (m, 1H). |
| 34 | 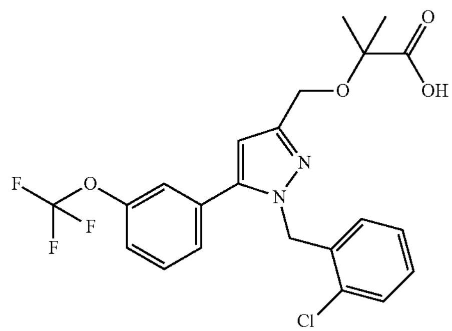 [SMILES: CC(C)(OCc1cc(-c2cccc(OC(F)(F)F)c2)n(Cc2ccccc2Cl)n1)C(=O)O] | 2-[[1-[(2-Chlorophenyl)methyl]-5-[3-(trifluoromethoxy)phenyl]pyrazol-3-yl]methoxy]-2-methyl-propanoic acid. <br> $^1$HNMR (CDCl$_3$): δ 1.56 (6H), 4.63 (s, 2H), 5.41 (s, 2H), 6.46 (s, 1H), 6.77-6.79 (m, 1H), 7.12-7.25 (m, 5H), 7.32-7.35 (m, 1H), 7.38-7.42 (m, 1H). |
| 35 | 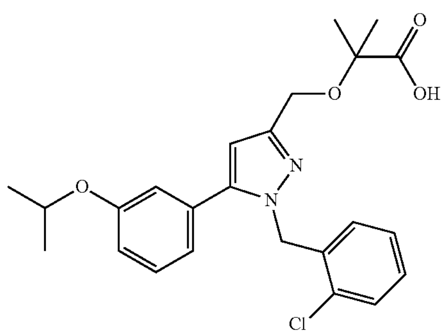 [SMILES: CC(C)Oc1cccc(-c2cc(COC(C)(C)C(=O)O)nn2Cc2ccccc2Cl)c1] | 2-[[1-[(2-Chlorophenyl)methyl]-5-(3-isopropoxyphenyl)pyrazol-3-yl]methoxy]-2-methyl-propanoic acid. <br> $^1$HNMR (CDCl$_3$): δ 1.22 (s, 3H) (, 1.23 (s, 3H), 1.55 (s, 6H), 4.30-4.33 (m, 1H), 4.62 (s, 2H), 5.43 (s, 2H), 6.41 (s, 1H), 6.75-6.90 (4H), 7.19-7.35 (m, 4H). |
| 36 | 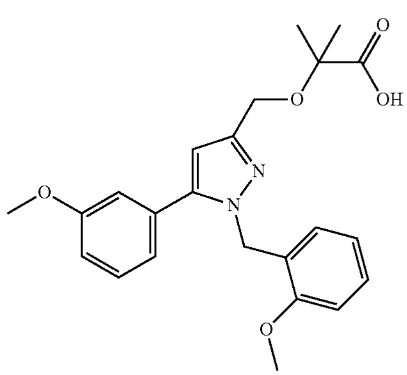 [SMILES: COc1cccc(-c2cc(COC(C)(C)C(=O)O)nn2Cc2ccccc2OC)c1] | 2-[[5-(3-Methoxyphenyl)-1-[(2-methoxyphenyl)methyl]pyrazol-3-yl]methoxy]-2-methyl-propanoic acid. <br> $^1$HNMR (CDCl$_3$): δ 1.55 (s. 6H), 3.70 (s, 3H), 3.73 (s, 3H), 4.62 (s, 2H), 5.34 (s, 2H), 6.35 (s, 1H), 6.77-6.392 (m, 6H), 7.22-7.29 (m, 2H). |

TABLE 1-continued

| Example # | Structure | IUPAC Name and Analytical data |
|---|---|---|
| 37 | 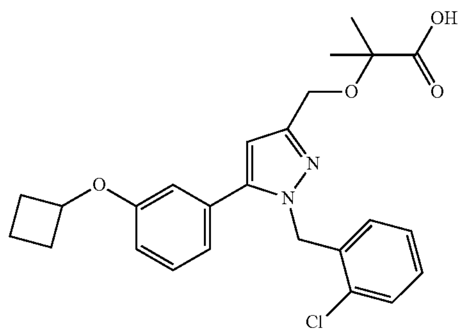 [SMILES: CC(C)(OCc1cc(-c2cccc(OC3CCC3)c2)n(Cc2ccccc2Cl)n1)C(=O)O] | 2-[[1-[(2-Chlorophenyl)methyl]-5-[3-(cyclobutoxy)phenyl]pyrazol-3-yl]methoxy]-2-methyl-propanoic acid. $^1$HNMR (CDCl$_3$): δ 1.49-1.61 (m, 7H), m1.75-1.82 (m 1H), 2.01-2.11 (m 2H), 2.17-2.24 (m 2H), 4.37-4.45 (m 1H), 4.62 (s, 2H), 5.42 (s, 2H), 6.39 (s, 1H), 6.64 (s, 1H), 6.75-6.86 (m, 3H), 7.19-7.35 (m 4H). |
| 38 | 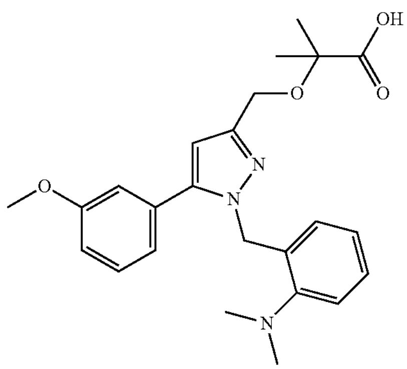 [SMILES: COc1cccc(-c2cc(COC(C)(C)C(=O)O)nn2Cc2ccccc2N(C)C)c1] | 2-[[1-[[2-(Dimethylamino)phenyl]methyl]-5-(3-methoxyphenyl)pyrazol-3-yl]methoxy]-2-methyl-propanoic acid. $^1$HNMR (CDCl$_3$): δ 1.56 (s, 6H), 2.60 (s, 6H), 6.64 (s, 3H), 4.63 (s, 2H), 5.44 (s, 2H). 6.30 (s, 1H), 6.71-7.11 (m 6H), 7.20-7.25 (m, 2H). |
| 39 | 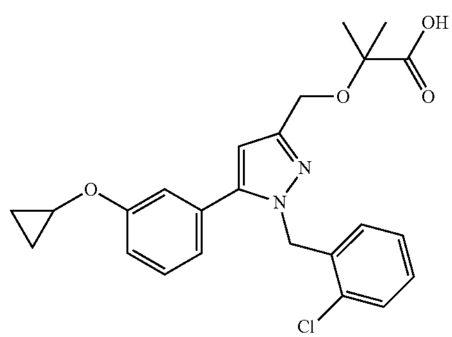 [SMILES: CC(C)(OCc1cc(-c2cccc(OC3CC3)c2)n(Cc2ccccc2Cl)n1)C(=O)O] | 2-[[1-[(2-Chlorophenyl)methyl]-5-[3-(cyclopropoxy)phenyl]pyrazol-3-yl]methoxy]-2-methyl-propanoic acid. $^1$HNMR (CDCl$_3$): δ 0.55-0.68 (m 4H), 1.55 (s, 6H), 3.50-3.54 (m 1H), 4.63 (s, 2H), 5.44 (s, 2H), 6.42 (s, 1H), 6.76-7.02 (m, 4H), 7.17-7.35 (m, 4H). |
| 40 | 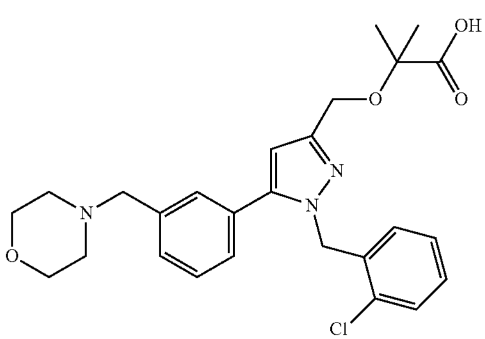 [SMILES: CC(C)(OCc1cc(-c2cccc(CN3CCOCC3)c2)n(Cc2ccccc2Cl)n1)C(=O)O] | 2-[[1-[(2-Chlorophenyl)methyl]-5-[3-(morpholinomethyl)phenyl]pyrazol-3-yl]methoxy]-2-methyl-propanoic acid. $^1$HNMR (CD$_3$OD): δ 1.50 (s, 6H), 3.15-3.23 (bs, 4H), 3.60-3.81 (bs, 2H), 3.85-4.16 (bs, 2H), 4.35 (s, 2H), 4.57 (s, 2H), 5.45 (s, 2H), 6.60 (s, 1H), 6.75 (d, 1H), 7.20-7.55 (m, 7H). |

TABLE 1-continued

| Example # | Structure | IUPAC Name and Analytical data |
|---|---|---|
| 41 | 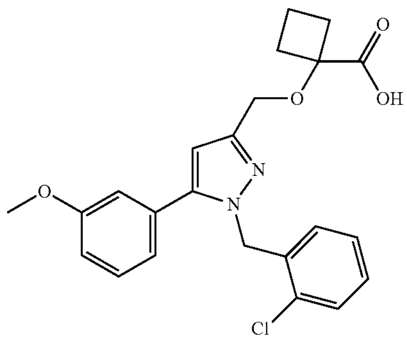 [SMILES: COc1cccc(-c2cc(COC3(C(=O)O)CCC3)nn2Cc2ccccc2Cl)c1] | 1-[[1-[(2-Chlorophenyl)methyl]-5-(3-methoxyphenyl)pyrazol-3-yl]methoxy]cyclobutanecarboxylic acid. <br> $^1$HNMR (CDCl$_3$): δ 1.78-1.85 (m 1H), 1.95-2.04 (m, 2H), 2.18-2.25 (m, 1H), 3.09-3.14 (m, 1H), 3.66 (s, 3H), 4.27-4.32 (m, 1H), 4.55-4.65 (dd, 2H), 5.43 (s, 2H), 6.44 (s, 1H), 6.73-6.91 (m, 4H), 7.17-7.34 (m 4). |
| 42 | 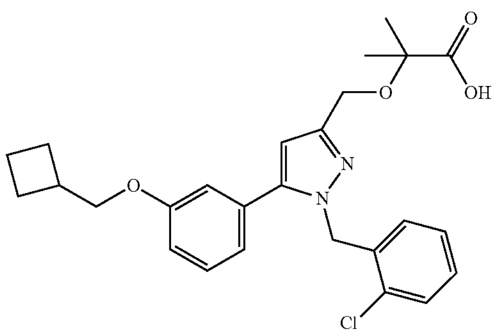 [SMILES: CC(C)(OCc1cc(-c2cccc(OCC3CCC3)c2)n(Cc2ccccc2Cl)n1)C(=O)O] | 2-[[1-[(2-Chlorophenyl)methyl]-5-[3-(cyclobutylmethoxy)phenyl]pyrazol-3-yl]methoxy]-2-methyl-propanoic acid. <br> $^1$HNMR (CDCl$_3$): δ 1.55 (s, 6H), 1.75-1.82 (m, 2H), 1.85-1.98 (m, 2H), 2.06-2.14 (m, 2H), 2.64-2.70 (m, 1H), 3.71 (d, 2H), 4.63 (s, 2H), 5.43 (s, 2H), 6.42 (s, 1H), 6.75-6.92 (m, 4H), 7.20-7.36 (m, 4). |
| 43 | 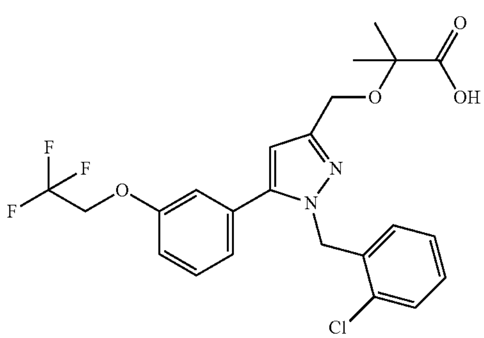 [SMILES: CC(C)(OCc1cc(-c2cccc(OCC(F)(F)F)c2)n(Cc2ccccc2Cl)n1)C(=O)O] | 2-[[1-[(2-Chlorophenyl)methyl]-5-[3-(2,2,2-trifluoroethoxy)phenyl]pyrazol-3-yl]methoxy]-2-methyl-propanoic acid. <br> $^1$HNMR (CDCl$_3$): δ 1.55 (s, 6H), 4.16 (q, 2H), 4.63 (s, 2H), 5.42 (s, 2H), 6.43 (s, 1H), 6.77-6.81 (m, 2H), 6.96-6.98 (m, 2H), 7.19-7.36 (m, 4H). |
| 44 | 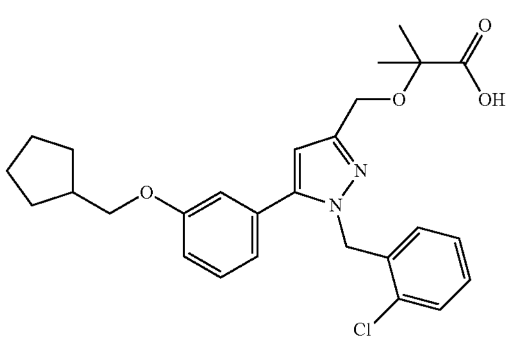 [SMILES: CC(C)(OCc1cc(-c2cccc(OCC3CCCC3)c2)n(Cc2ccccc2Cl)n1)C(=O)O] | 2-[[1-[(2-Chlorophenyl)methyl]-5-[3-(cyclopentylmethoxy)phenyl]pyrazol-3-yl]methoxy]-2-methyl-propanoic acid. <br> $^1$HNMR (CDCl$_3$): δ 1.25-1.29 (m, 2H), 1.55-1.61 (m, 10H), 1.76-1.79 (m, 2H), 2.24-2.31 (m, 1H), 3.59 (d, 2H), 4.62 (s, 2H), 5.43 (s, 2H), 6.41 (s, 1H), 6.73-6.91 (m, 4H), 7.19-7.35 (m, 4H). |

TABLE 1-continued

| Example # | Structure | IUPAC Name and Analytical data |
|---|---|---|
| 45 | 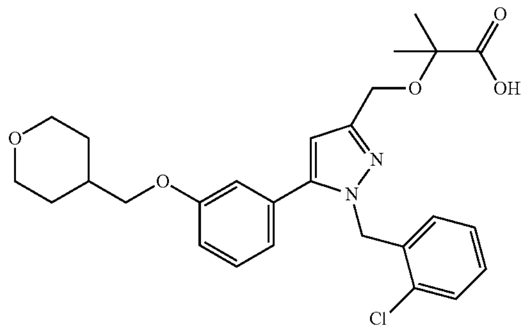 [SMILES: CC(C)(OCc1cc(-c2cccc(OCC3CCOCC3)c2)n(Cc2ccccc2Cl)n1)C(=O)O] | 2-[[1-[(2-Chlorophenyl)methyl]-5-[3-(tetrahydropyran-4-ylmethoxy)phenyl]pyrazol-3-yl]methoxy]-2-methyl-propanoic acid.<br>$^1$HNMR (CDCl$_3$): δ 1.34-1.41 (m, 2H), 1.55 (s, 6H), 1.66-1.69 (m, 2H), 1.97-1.99 (m, 1H), 3.38-3.46m, 2H), 3.56 (d, 2H), 3.98-4.01 (m, 2H), 4.62 (s, 2H), 5.42 (s, 2H), 6.42 (s, 1H), 6.71 (s, 1H), 6.77-6.95 (m, 3H), 7.19-7.35 (m, 4H). |
| 46 | 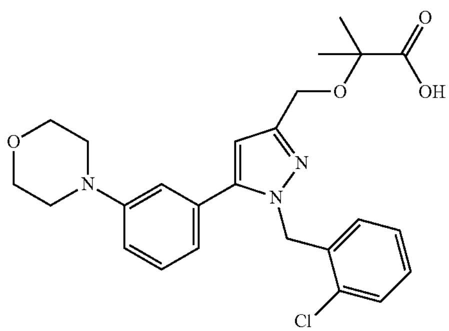 [SMILES: CC(C)(OCc1cc(-c2cccc(N3CCOCC3)c2)n(Cc2ccccc2Cl)n1)C(=O)O] | 2-[[1-[(2-Chlorophenyl)methyl]-5-(3-morpholinophenyl)pyrazol-3-yl]methoxy]-2-methyl-propanoic acid.<br>$^1$HNMR (CDCl$_3$): δ 1.55 (s, 6H), 2.96 (t, 4H), 3.76 (t, 4H), 4.62 (s, 2H), 5.41 (s, 2H), 6.41 (s, 1H), 6.68 (s, 1H), 6.78-6.80 (m, 2H), 6.88-6.91 (m, 1H), 7.19-7.35 (m, 4H). |
| 47 | 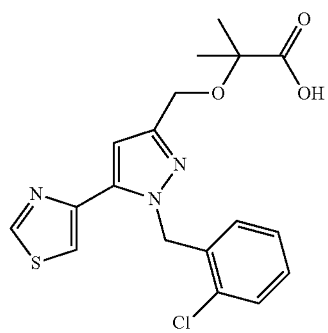 [SMILES: CC(C)(OCc1cc(-c2cscn2)n(Cc2ccccc2Cl)n1)C(=O)O] | 2-([1-[(o-Chlorophenyl)methyl]-5-(1,3-thiazol-4-yl)-1H-pyrazol-3-yl]methoxy)-2-methylpropionic acid<br>$^1$HNMR (CDCl$_3$): δ 1.56 (s, 6H), 4.63 (s, 2H), 5.84 (s, 2H), 6.62-6.67 (m, 2H), 7.10-7.19 (m 2H), 7.33-7.35 (m, 1H), 7.39 (d, 1H), 8.83 (d, 1H). |
| 48 | 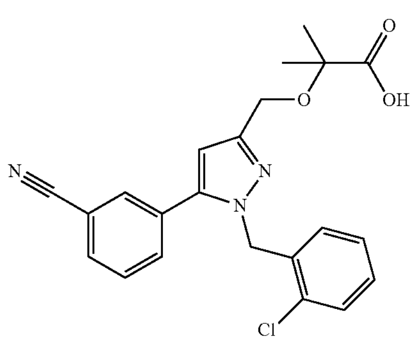 [SMILES: CC(C)(OCc1cc(-c2cccc(C#N)c2)n(Cc2ccccc2Cl)n1)C(=O)O] | 2-([1-[(o-Chlorophenyl)methyl]-5-(m-cyanophenyl)-1H-pyrazol-3-yl]methoxy)-2-methylpropionic acid<br>$^1$HNMR (CDCl$_3$): δ 1.56 (s, 6H), 4.62 (s, 2H), 5.39 (s, 2H), 6.46 (s, 1H), 6.82-6.84 (m, 1H), 7.18-7.24 (m, 2H), 7.33-7.35 (m 1H), 7.46-7.55 (m, 3H), 7.65-7.68 (m, 1H). |

TABLE 1-continued

| Example # | Structure | IUPAC Name and Analytical data |
|---|---|---|
| 49 | 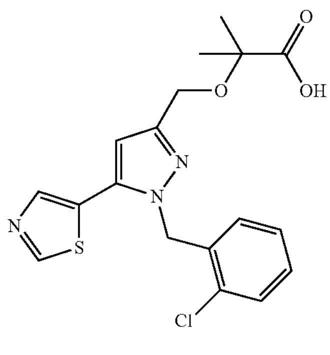 [SMILES: CC(C)(OCc1cc(-c2cncs2)n(Cc2ccccc2Cl)n1)C(=O)O] | 2-([1-[(o-Chlorophenyl)methyl]-5-(1,3-thiazol-5-yl)-1H-pyrazol-3-yl]methoxy)-2-methylpropionic acid<br>$^1$HNMR (CDCl$_3$): δ 1.56 (s, 6H), 4.62 (s, 2H), 5.50 (s, 2H), 6.60-6.6 (m, 2H), 7.14-7.24 (m, 2H), 7.36-7.38 (m, 1H), 7.76 (s, 1H), 8.84 (s, 1H). |
| 50 | 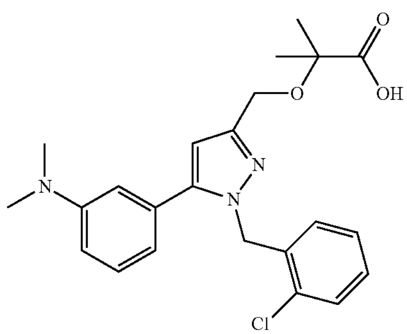 [SMILES: CN(C)c1cccc(-c2cc(COC(C)(C)C(=O)O)nn2Cc2ccccc2Cl)c1] | 2-([1-[(o-Chlorophenyl)methyl]-5-[m-(dimethylamino)phenyl]-1H-pyrazol-3-yl]methoxy)-2-methylpropionic acid<br>MS: Calculated: 427.92; Found: 428.9 [M + H]. |

Example 51: 2-([1-[(2-Chlorophenyl)methyl]-5-[3-(propan-2-yl)phenyl]-1H-pyrazol-3-yl]methoxy)-2-methylpropanoic acid

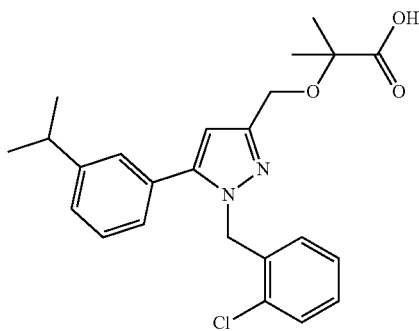 [SMILES: CC(C)c1cccc(-c2cc(COC(C)(C)C(=O)O)nn2Cc2ccccc2Cl)c1]

(i) 1-[3-(Propan-2-yl)phenyl]ethan-1-one: Into a 500-mL round-bottom flask purged and maintained with an inert atmosphere of N$_2$ was placed a solution of 1-bromo-3-(propan-2-yl)benzene (5.0 g, 25.11 mmol, 1.00 equiv) in THF (250 mL). This was followed by the addition of n-BuLi (20 mL, 2.00 equiv) dropwise with stirring at −60° C. The mixture was stirred at −60° C. for 30 min. To this was added N-methoxy-N-methylacetamide (3.9 g, 37.82 mmol, 1.50 equiv) dropwise with stirring at −30° C. The resulting solution was stirred for 3 h at −30° C. in a liquid N$_2$ bath. The reaction was then quenched by the addition of 20 mL of water. The resulting solution was diluted with 200 mL of EtOAc, washed with 2×100 mL of brine, dried over anhydrous Na$_2$SO$_4$ and concentrated under vacuum. The residue was applied onto a silica gel column with EtOAc/petroleum ether (1:10). This resulted in 2.7 g (66%) of the title product as colorless oil.

(ii) 2,4-Dioxo-4-[3-(propan-2-yl)phenyl]butanoate: Into a 100-mL round-bottom flask, MeONa (9.25 mL of 25% solution in MeOH, 3.00 equiv, 5.4%) was added to a solution of 1-[3-(propan-2-yl)phenyl]ethan-1-one (2.7 g, 16.64 mmol, 1.00 equiv) in MeOH (30 mL). This was followed by the addition of dimethyl oxalate (1.97 g, 16.68 mmol, 2.00 equiv), in portions at room temperature. The resulting solution was stirred for 16 h at room temperature. The reaction was then quenched by the addition of 200 mL of water/ice. The pH value of the solution was adjusted to 3-4 with conc HCl. The resulting solution was extracted with 3×100 mL of EtOAc and the organic layers were combined, washed with 2×100 mL of brine, dried, and evaporated. The solid was dried in an oven under reduced pressure. This resulted in 4.0 g (97%) of the title product as yellow oil.

(iii) Methyl 1-[(2-chlorophenyl)methyl]-5-[3-(propan-2-yl)phenyl]-1H-pyrazole-3-carboxylate: Into a 50-mL round-bottom flask was placed a solution of methyl 2,4-dioxo-4-[3-(propan-2-yl)phenyl]butanoate (1.0 g, 4.03 mmol, 1.00 equiv) and [(2-chlorophenyl)methyl]-hydrazine dihydrochloride (1.38 g, 6.01 mmol, 1.50 equiv) in AcOH (20 mL). The resulting solution was stirred for 2 h at 100° C. in an oil bath. The resulting mixture was concentrated under vacuum, diluted with 200 mL of EtOAc, washed with 2×100 mL of sat NaHCO₃, dried over anhydrous Na₂SO₄ and concentrated under vacuum. The residue was applied onto a silica gel column with EtOAc/petroleum ether (1:5). This resulted in 1.05 g (71%) of the title product as a yellow solid.

(iv) 2-([1-[(2-Chlorophenyl)methyl]-5-[3-(propan-2-yl)phenyl]-1H-pyrazol-3-yl]methoxy)-2-methylpropanoic acid was prepared analogously as described in Steps ii-iv of Example 1. This resulted in 70 mg as a white solid. ¹H-NMR (300 MHz, MeOD): δ 1.12 (6H, d), 1.53 (6H, s), 2.83 (1H, p), 4.60 (2H, s), 5.40 (2H, s), 6.54 (1H, s), 6.72-6.81 (1H, m), 7.05-7.45 (7H, m).

Examples 52-59 were prepared analogously as described in Example 51.

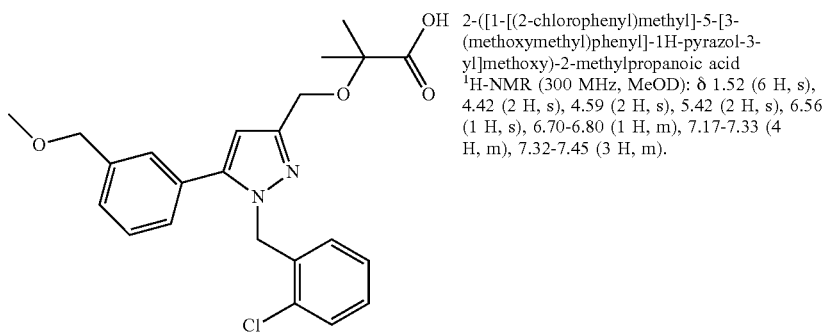

52  2-([1-[(2-chlorophenyl)methyl]-5-[3-(methoxymethyl)phenyl]-1H-pyrazol-3-yl]methoxy)-2-methylpropanoic acid
¹H-NMR (300 MHz, MeOD): δ 1.52 (6 H, s), 4.42 (2 H, s), 4.59 (2 H, s), 5.42 (2 H, s), 6.56 (1 H, s), 6.70-6.80 (1 H, m), 7.17-7.33 (4 H, m), 7.32-7.45 (3 H, m).

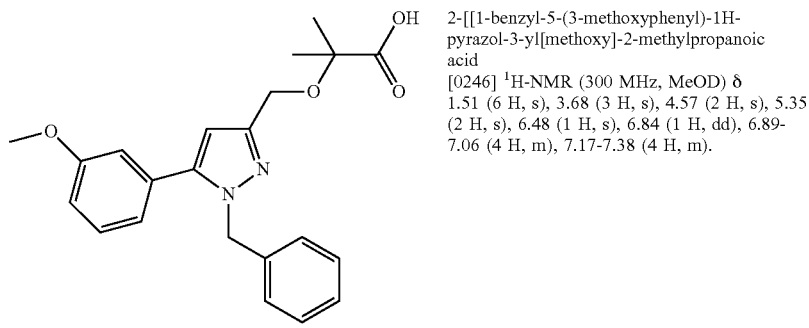

53  2-[[1-benzyl-5-(3-methoxyphenyl)-1H-pyrazol-3-yl[methoxy]-2-methylpropanoic acid
[0246] ¹H-NMR (300 MHz, MeOD) δ 1.51 (6 H, s), 3.68 (3 H, s), 4.57 (2 H, s), 5.35 (2 H, s), 6.48 (1 H, s), 6.84 (1 H, dd), 6.89-7.06 (4 H, m), 7.17-7.38 (4 H, m).

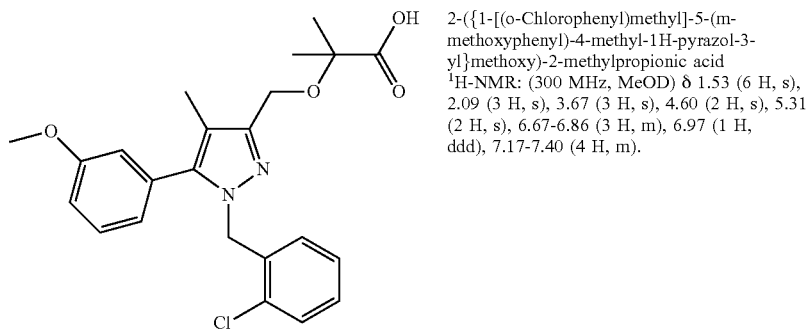

54  2-({1-[(o-Chlorophenyl)methyl]-5-(m-methoxyphenyl)-4-methyl-1H-pyrazol-3-yl}methoxy)-2-methylpropionic acid
¹H-NMR: (300 MHz, MeOD) δ 1.53 (6 H, s), 2.09 (3 H, s), 3.67 (3 H, s), 4.60 (2 H, s), 5.31 (2 H, s), 6.67-6.86 (3 H, m), 6.97 (1 H, ddd), 7.17-7.40 (4 H, m).

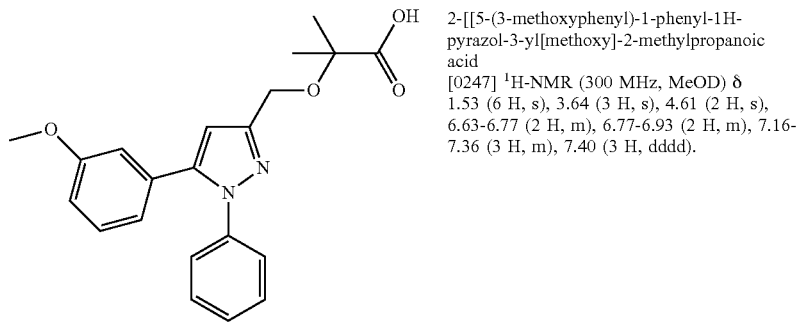

55  2-[[5-(3-methoxyphenyl)-1-phenyl-1H-pyrazol-3-yl[methoxy]-2-methylpropanoic acid
[0247] ¹H-NMR (300 MHz, MeOD) δ 1.53 (6 H, s), 3.64 (3 H, s), 4.61 (2 H, s), 6.63-6.77 (2 H, m), 6.77-6.93 (2 H, m), 7.16-7.36 (3 H, m), 7.40 (3 H, dddd).

| | | |
|---|---|---|
| 56 | 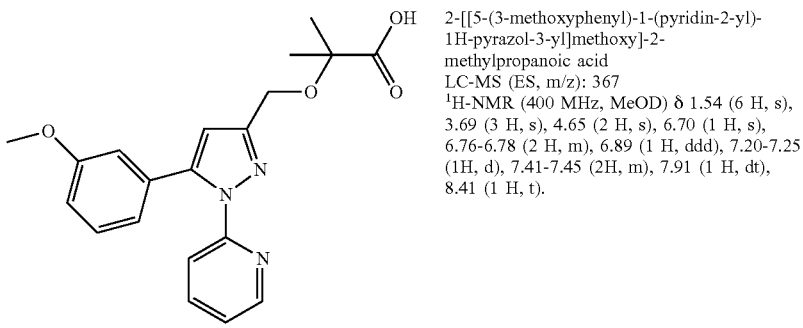 | 2-[[5-(3-methoxyphenyl)-1-(pyridin-2-yl)-1H-pyrazol-3-yl]methoxy]-2-methylpropanoic acid<br>LC-MS (ES, m/z): 367<br>$^1$H-NMR (400 MHz, MeOD) δ 1.54 (6 H, s), 3.69 (3 H, s), 4.65 (2 H, s), 6.70 (1 H, s), 6.76-6.78 (2 H, m), 6.89 (1 H, ddd), 7.20-7.25 (1H, d), 7.41-7.45 (2H, m), 7.91 (1 H, dt), 8.41 (1 H, t). |
| 57 | 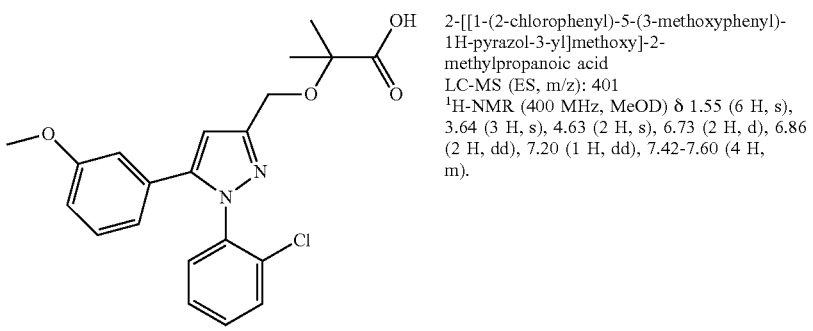 | 2-[[1-(2-chlorophenyl)-5-(3-methoxyphenyl)-1H-pyrazol-3-yl]methoxy]-2-methylpropanoic acid<br>LC-MS (ES, m/z): 401<br>$^1$H-NMR (400 MHz, MeOD) δ 1.55 (6 H, s), 3.64 (3 H, s), 4.63 (2 H, s), 6.73 (2 H, d), 6.86 (2 H, dd), 7.20 (1 H, dd), 7.42-7.60 (4 H, m). |
| 58 | 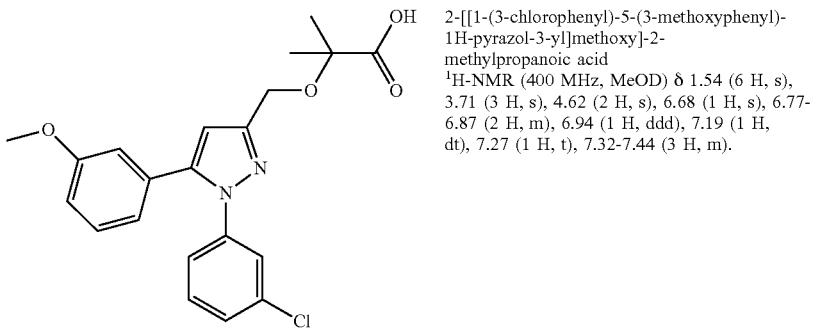 | 2-[[1-(3-chlorophenyl)-5-(3-methoxyphenyl)-1H-pyrazol-3-yl]methoxy]-2-methylpropanoic acid<br>$^1$H-NMR (400 MHz, MeOD) δ 1.54 (6 H, s), 3.71 (3 H, s), 4.62 (2 H, s), 6.68 (1 H, s), 6.77-6.87 (2 H, m), 6.94 (1 H, ddd), 7.19 (1 H, dt), 7.27 (1 H, t), 7.32-7.44 (3 H, m). |
| 59 | 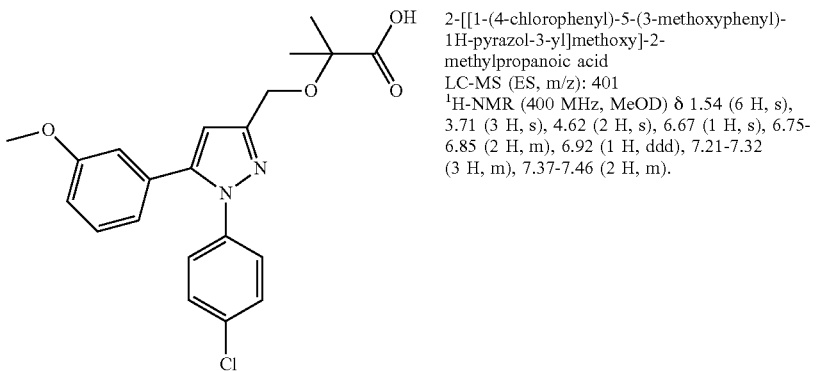 | 2-[[1-(4-chlorophenyl)-5-(3-methoxyphenyl)-1H-pyrazol-3-yl]methoxy]-2-methylpropanoic acid<br>LC-MS (ES, m/z): 401<br>$^1$H-NMR (400 MHz, MeOD) δ 1.54 (6 H, s), 3.71 (3 H, s), 4.62 (2 H, s), 6.67 (1 H, s), 6.75-6.85 (2 H, m), 6.92 (1 H, ddd), 7.21-7.32 (3 H, m), 7.37-7.46 (2 H, m). |

Example 60: 2-([1-Benzyl-5-[3-(2-methylpropoxy)phenyl]-1H-pyrazol-3-yl]methoxy)-2-methylpropanoic acid

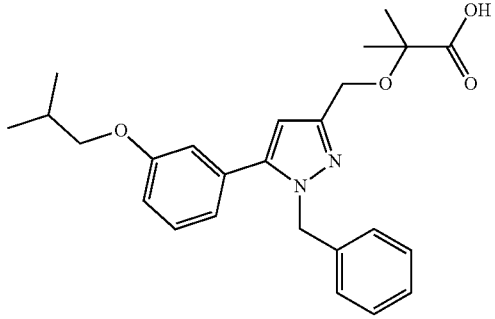 [SMILES: CC(C)COc1cccc(-c2cc(COC(C)(C)C(=O)O)nn2Cc2ccccc2)c1]

(i) 1-[3-(2-Methylpropoxy)phenyl]ethan-1-one: Into a 500-mL round-bottom flask was placed a solution of 1-(3-hydroxyphenyl)ethan-1-one (20 g, 146.90 mmol, 1.00 equiv), $K_3PO_4$ (62 g, 292.08 mmol, 2.00 equiv) and 1-bromo-2-methylpropane (40 g, 291.93 mmol, 2.00 equiv) in DMSO (240 mL). The resulting solution was stirred for 16 h at 60° C. The resulting solution was extracted with 2×500 mL of EtOAc, and the organic layers were combined and dried over anhydrous $Na_2SO_4$. The residue was applied onto a silica gel column with EtOAc/petroleum ether (1:5). This resulted in 21.24 g (75%) of the title product as a yellow liquid.

(ii) 2-([1-Benzyl-5-[3-(2-methylpropoxy)phenyl]-1H-pyrazol-3-yl]methoxy)-2-methylpropanoic acid was obtained analogously to Example 67. This resulted in 103.1 mg as a white solid. $^1$H-NMR (400 MHz, MeOD) δ 0.97 (6H, d), 1.53 (6H, s), 1.97 (1H, dp), 3.48 (2H, d), 3.78 (3H, s), 4.58 (2H, s), 5.31 (2H, s), 6.52 (1H, s), 6.67-6.74 (1H, m), 6.76-6.82 (1H, m), 6.85-7.00 (4H, m), 7.22-7.33 (2H, m).

Examples 61-63 were prepared analogously as described in Example 60.

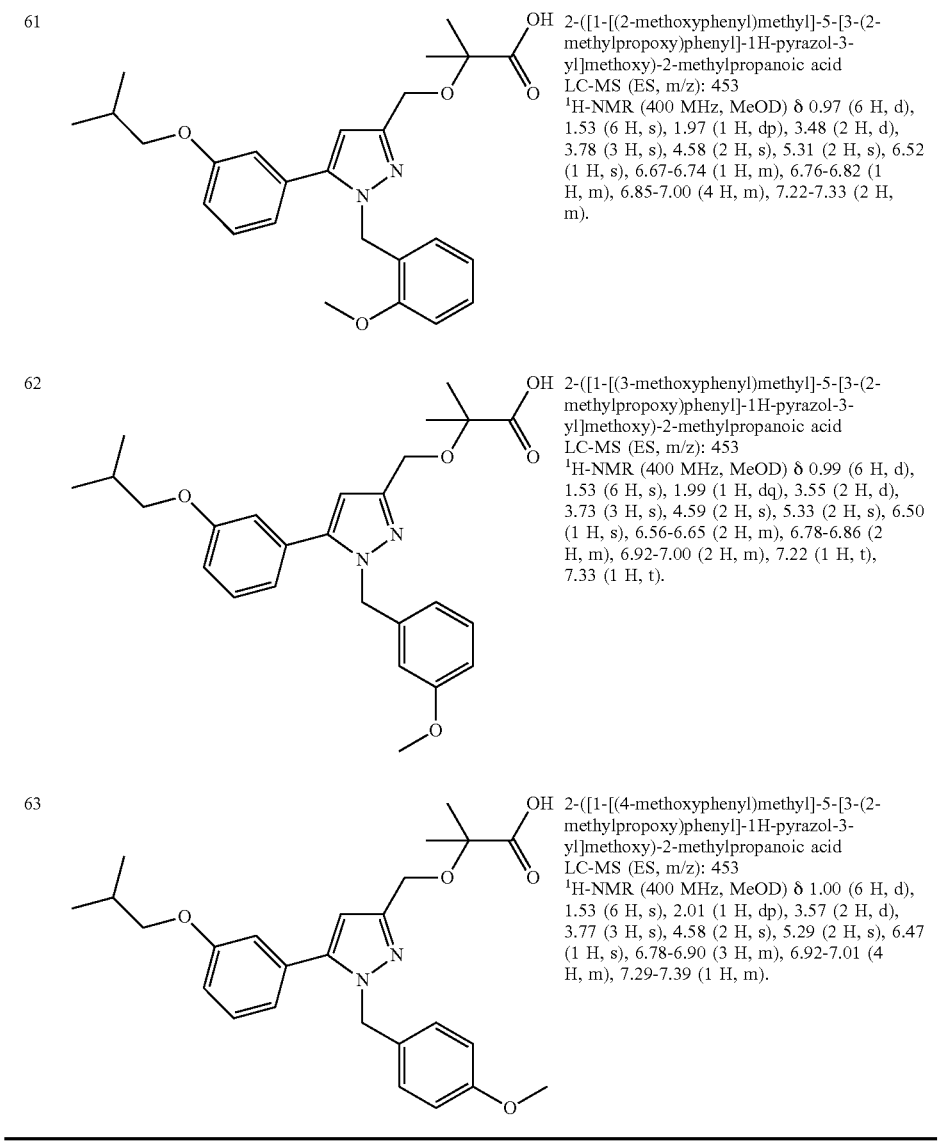

| 61 | 2-([1-[(2-methoxyphenyl)methyl]-5-[3-(2-methylpropoxy)phenyl]-1H-pyrazol-3-yl]methoxy)-2-methylpropanoic acid LC-MS (ES, m/z): 453 $^1$H-NMR (400 MHz, MeOD) δ 0.97 (6 H, d), 1.53 (6 H, s), 1.97 (1 H, dp), 3.48 (2 H, d), 3.78 (3 H, s), 4.58 (2 H, s), 5.31 (2 H, s), 6.52 (1 H, s), 6.67-6.74 (1 H, m), 6.76-6.82 (1 H, m), 6.85-7.00 (4 H, m), 7.22-7.33 (2 H, m). |

| 62 | 2-([1-[(3-methoxyphenyl)methyl]-5-[3-(2-methylpropoxy)phenyl]-1H-pyrazol-3-yl]methoxy)-2-methylpropanoic acid LC-MS (ES, m/z): 453 $^1$H-NMR (400 MHz, MeOD) δ 0.99 (6 H, d), 1.53 (6 H, s), 1.99 (1 H, dq), 3.55 (2 H, d), 3.73 (3 H, s), 4.59 (2 H, s), 5.33 (2 H, s), 6.50 (1 H, s), 6.56-6.65 (2 H, m), 6.78-6.86 (2 H, m), 6.92-7.00 (2 H, m), 7.22 (1 H, t), 7.33 (1 H, t). |

| 63 | 2-([1-[(4-methoxyphenyl)methyl]-5-[3-(2-methylpropoxy)phenyl]-1H-pyrazol-3-yl]methoxy)-2-methylpropanoic acid LC-MS (ES, m/z): 453 $^1$H-NMR (400 MHz, MeOD) δ 1.00 (6 H, d), 1.53 (6 H, s), 2.01 (1 H, dp), 3.57 (2 H, d), 3.77 (3 H, s), 4.58 (2 H, s), 5.29 (2 H, s), 6.47 (1 H, s), 6.78-6.90 (3 H, m), 6.92-7.01 (4 H, m), 7.29-7.39 (1 H, m). |

Example 64: 2-([1-[(2-Chlorophenyl)methyl]-5-(5-methoxythiophen-2-yl)-1H-pyrazol-3-yl]methoxy)-2-methylpropanoic acid

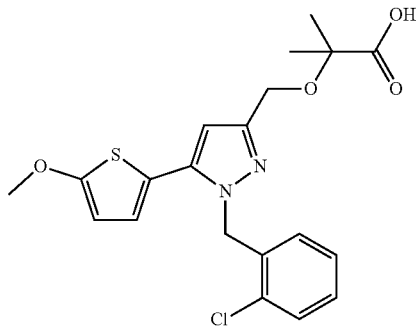 [SMILES: COc1ccc(-c2cc(COC(C)(C)C(=O)O)nn2Cc2ccccc2Cl)s1]

(i) 1-(5-Methoxythiophen-2-yl)ethan-1-one: Into a 25-mL sealed tube was placed 2-methoxythiophene (11 g, 96.35 mmol, 1.00 equiv), MeOH (60 mL), $Cs_2CO_3$ (22 g, 1.20 equiv), and Brettphos Pd G3 (550 mg). The final reaction mixture was irradiated with microwave radiation for 1 h at 100° C. The resulting mixture was concentrated under vacuum. The resulting solution was extracted with 3×100 mL of EtOAc, and the organic layers were combined, dried over anhydrous $MgSO_4$, and concentrated under vacuum. The residue was applied onto a silica gel column with EtOAc/petroleum ether (1/50). This resulted in 5 g (33%) of the title product as a yellow solid.

(ii) 2-([1-[(2-Chlorophenyl)methyl]-5-(5-methoxythiophen-2-yl)-1H-pyrazol-3-yl]methoxy)-2-methylpropanoic acid was prepared analogously as described in Steps ii-iv of Example 51. This resulted in 39.2 mg as a white solid. $^1$H-NMR (300 MHz, MeOD): δ 1.51 (6H, s), 3.86 (3H, s), 4.54 (2H, s), 5.50 (2H, s), 6.19 (1H, d), 6.51 (1H, s), 6.55-6.66 (2H, m), 7.25 (2H, dtd), 7.43 (1H, dd).

Example 65: 2-([1-[(2-Chlorophenyl)methyl]-5-(4-methoxythiophen-2-yl)-1H-pyrazol-3-yl]methoxy)-2-methylpropanoic acid

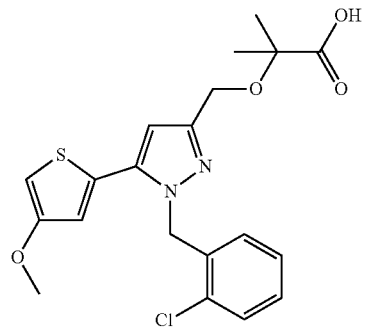 [SMILES: COc1csc(-c2cc(COC(C)(C)C(=O)O)nn2Cc2ccccc2Cl)c1]

(i) 1-(4-Methoxythiophen-2-yl)ethan-1-one: Into a 50-mL round-bottom flask purged and maintained with an inert atmosphere of $N_2$ was placed a solution of 1-(4-bromothiophen-2-yl)ethan-1-one (3.0 g, 14.63 mmol, 1.00 equiv) in MeOH (25 mL). This was followed by the addition of NaOMe (5.4 mL, 2.00 equiv, 5.4M) at room temperature. To this was added CuBr (627 mg, 4.38 mmol, 0.30 equiv) at room temperature. The resulting solution was stirred for 16 h at 100° C. in an oil bath, then diluted with 100 mL of EtOAc, washed with 2×100 mL of brine, dried over anhydrous $Na_2SO_4$ and concentrated under vacuum. The residue was applied onto a silica gel column with EtOAc/petroleum ether (1:20). This resulted in 700 mg (31%) of the title product as a yellow oil.

(ii) 2-([1-[(2-Chlorophenyl)methyl]-5-(4-methoxythiophen-2-yl)-1H-pyrazol-3-yl]methoxy)-2-methylpropanoic acid was prepared analogously as described in Steps ii-iv of Example 51. This resulted in 61 mg as a white solid. $^1$H-NMR (300 MHz, MeOD): δ 1.51 (6H, s), 3.76 (3H, s), 4.56 (2H, s), 5.54 (2H, s), 6.51 (1H, d), 6.56-6.69 (3H, m), 7.26 (2H, dtd), 7.44 (1H, dd).

Example 66: 2-([1-[(2-chlorophenyl)methyl]-5-(5-methoxythiophen-3-yl)-1H-pyrazol-3-yl]methoxy)-2-methylpropanoic acid was prepared analogously as described in Example 65.

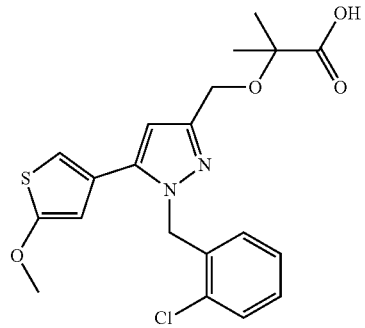 [SMILES: COc1cc(-c2cc(COC(C)(C)C(=O)O)nn2Cc2ccccc2Cl)cs1]

$^1$H-NMR (400 MHz, MeOD) δ 1.53 (6H, s), 3.85 (3H, s), 4.57 (2H, s), 5.52 (2H, s), 6.26 (1H, d), 6.52-6.59 (2H, m), 6.64-6.71 (1H, m), 7.28 (2H, dtd), 7.45 (1H, dd).

Example 67: 2-([1-[(o-Chlorophenyl)methyl]-5-(m-methoxyphenyl)-1H-pyrazol-3-yl)methoxy)-2-ethylbutyric acid was prepared analogously as described in Example 1, except that in place of Step iii, the following procedure was followed:

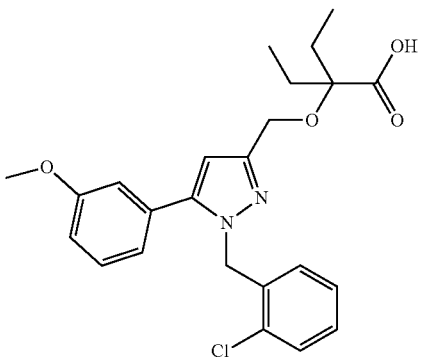 [SMILES: CCC(CC)(OCc1cc(-c2cccc(OC)c2)n(Cc2ccccc2Cl)n1)C(=O)O]

(i) Methyl 2-ethyl-2-hydroxybutanoate: Into a 250-mL round-bottom flask was placed a solution of 2-ethyl-2-hydroxybutanoic acid (2.0 g, 15.13 mmol, 1.00 equiv) in MeOH (100 mL). This was followed by the addition of sulfuric acid (3 mL) dropwise with stirring at room temperature. The resulting solution was heated to reflux for 16 h in an oil bath. The resulting mixture was concentrated under vacuum, diluted with 200 mL of EtOAc, washed with 2×100 mL of sat NaHCO₃, dried over anhydrous Na₂SO₄ and concentrated under vacuum. This resulted in 800 mg (36%) of the title product as a colorless oil.

(ii) 3-(Bromomethyl)-1-[(2-chlorophenyl)methyl]-5-(3-methoxyphenyl)-1H-pyrazole: Into a 100-mL round-bottom flask was placed a solution of [1-[(2-chlorophenyl)methyl]-5-(3-methoxyphenyl)-1H-pyrazol-3-yl]methanol (600 mg, 1.82 mmol, 1.00 equiv) in DCM (30 mL). This was followed by the addition of CBr₄ (900 mg, 1.50 equiv) at 0° C. over 1 min. To this was added PPh₃ (720 mg, 2.75 mmol, 1.50 equiv) in several batches at 0° C. over 5 min. The resulting solution was stirred for 16 h at 25° C. in an oil bath. The residue was applied onto a silica gel column with EtOAc/petroleum ether (1:11). The collected fractions were combined and concentrated under vacuum. This resulted in 550 mg (77%) of the title product as a yellow oil.

(iii) Methyl 2-([1-[(2-chlorophenyl)methyl]-5-(3-methoxyphenyl)-1H-pyrazol-3-yl]methoxy)-2-ethylbutanoate: Into a 40-mL vial was placed a solution of methyl 2-ethyl-2-hydroxybutanoate (371 mg, 2.54 mmol, 2.00 equiv) in DMF/THF (7/7 mL). This was followed by the addition of NaH (100 mg, 4.17 mmol, 2.00 equiv) at 0° C. in 30 min. To this was added NaI (140 mg) and 3-(bromomethyl)-1-[(2-chlorophenyl)methyl]-5-(3-methoxyphenyl)-1H-pyrazole (500 mg, 1.28 mmol, 1.00 equiv). The resulting solution was stirred for 16 h at room temperature. The residue was applied onto a Prep-TLC with EtOAc/petroleum ether (1:10). The collected fractions were combined and concentrated under vacuum. This resulted in 210 mg (38%) of the title product as a white liquid.

LiOH treatment as in Step iv of Example 1 resulted in 210 mg of the title compound as a white liquid. ¹H-NMR (400 MHz, MeOD): δ (0.91 (6H, t), 1.87 (4H, q), 3.68 (3H, s), 4.52 (2H, s), 5.43 (2H, s), 6.67 (1H, s), 6.72-6.86 (2H, m), 6.88-7.00 (2H, m), 7.21-7.36 (3H, m), 7.37-7.48 (1H, m).

Example 68: 2-([1-[(2-Chlorophenyl)methyl]-5-(3-methoxyphenyl)-1H-pyrazol-3-yl]methoxy)-2-methylbutanoic acid was prepared analogously as described in Example 64.

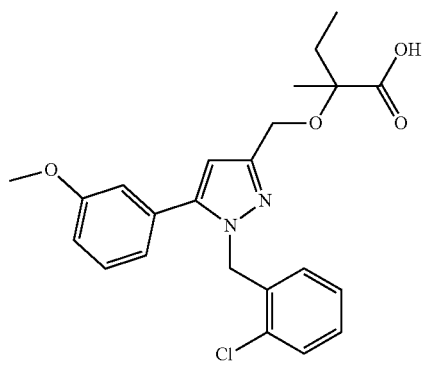 [SMILES: CCC(C)(OCc1cc(-c2cccc(OC)c2)n(Cc2ccccc2Cl)n1)C(=O)O]

¹H-NMR (400 MHz, MeOD) δ 0.97 (3H, t), 1.51 (3H, s), 1.89 (2H, qd), 3.68 (3H, s), 4.59 (2H, s), 5.44 (2H, s), 6.56 (1H, s), 6.71-6.79 (1H, m), 6.83 (1H, dd), 6.89-7.01 (2H, m), 7.22-7.36 (3H, m), 7.37-7.45 (1H, m).

Example 69: 2-([1-[(2-Chlorophenyl)methyl]-5-[3-(2-methylpropanamido)phenyl]-1H-pyrazol-3-yl]methoxy)-2-methylpropanoic acid

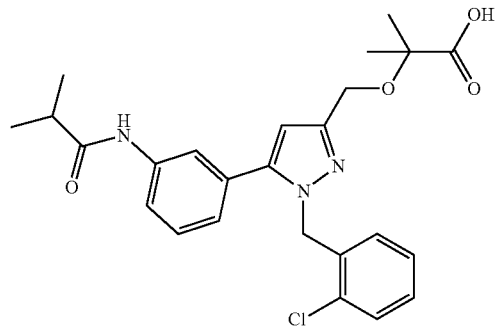 [SMILES: CC(C)C(=O)Nc1cccc(-c2cc(COC(C)(C)C(=O)O)nn2Cc2ccccc2Cl)c1]

(i) Methyl 4-(3-nitrophenyl)-2,4-dioxobutanoate: Into a 1000-mL 3-necked round-bottom flask, MeONa (90 mL, 4.00 equiv), and dimethyl oxalate (18.6 g, 157.51 mmol, 1.30 equiv) were added stepwise to a solution of 1-(3-nitrophenyl)ethan-1-one (20 g, 121.10 mmol, 1.00 equiv) in MeOH (700 mL). The resulting solution was stirred overnight at room temperature. The resulting solution was poured into 500 mL of H₂O/ice. The pH value of the solution was adjusted to 3-5 with HCl (12 mol/L). The solution was extracted with 2×1000 mL of EtOAc and the organic layers were combined, washed with 2×1000 mL of brine, dried over anhydrous Na₂SO₄ and concentrated under vacuum. This resulted in 18 g (59%) of the title product as a yellow solid.

(ii) Methyl 5-(3-nitrophenyl)-1H-pyrazole-3-carboxylate: Into a 500-mL round-bottom flask was placed a solution of methyl 4-(3-nitrophenyl)-2,4-dioxobutanoate (15 g, 59.72 mmol, 1.00 equiv) and H₂NNH₂ hydrate (3.9 mL, 1.20 equiv) in AcOH (200 mL). The resulting solution was stirred for 3 h at 120° C. in an oil bath. The reaction mixture was cooled to room temperature. The solids were collected by filtration. This resulted in 9.5 g (64%) of the title product as a yellow solid.

(iii) Methyl 1-[(2-chlorophenyl)methyl]-5-(3-nitrophenyl)-1H-pyrazole-3-carboxylate: Into a 25-mL 3-necked round-bottom flask purged and maintained with an inert atmosphere of N₂, was placed a solution of methyl 5-(3-nitrophenyl)-1H-pyrazole-3-carboxylate (9.0 g, 36.41 mmol, 1.00 equiv) in toluene (170 mL). This was followed by the addition of NaH (2.92 g, 73.00 mmol, 2.00 equiv, 60%), in portions at room temperature. The reaction was stirred at rt for 30 mins. To this was added a solution of 1-(bromomethyl)-2-chlorobenzene (11.2 g, 54.51 mmol, 1.50 equiv) in toluene (30 mL) dropwise with stirring at 60° C. The resulting solution was stirred for 5 h at 110° C. in an oil bath. The reaction mixture was cooled to room temperature. The reaction was then quenched by the addition of 200 mL of sat NH₄Cl. The resulting solution was diluted with 300 mL of EtOAc. The resulting solution was extracted with 2×300 mL of EtOAc and the organic layers were combined, washed with 3×300 mL of brine, dried over Na₂SO₄ and concentrated under vacuum. The residue was applied onto a silica gel column with PE:EtOAc (3:1). This resulted in 4.0 g (30%) of the title product as a white solid.

(iv) Methyl 2-([1-[(2-chlorophenyl)methyl]-5-(3-nitrophenyl)-1H-pyrazol-3-yl]methoxy)-2-methylpropanoate was prepared analogously as described in Steps ii-iii of Example 1.

(v) Methyl 2-[[5-(3-aminophenyl)-1-[(2-chlorophenyl) methyl]-1H-pyrazol-3-yl]methoxy]-2-methylpropanoate: Into a 25-mL round-bottom flask was placed a solution of methyl 2-([1-[(2-chlorophenyl)methyl]-5-(3-nitrophenyl)-1H-pyrazol-3-yl]methoxy)-2-methylpropanoate (400 mg, 0.90 mmol, 1.00 equiv) in AcOH/H₂O (10/1 mL). This was followed by the addition of Zn (400 mg, 6.15 mmol), in portions at room temperature. The resulting mixture was stirred for 2 h at room temperature. The solids were removed by filtration. The pH value of the solution was adjusted to 7-8 with sat NaHCO₃. The resulting solution was extracted with mL of EtOAc, and the organic layers were combined, washed with 2×200 mL of brine, dried over anhydrous Na₂SO₄ and concentrated under vacuum. The residue was purified by Prep-TLC with DCM/MeOH (30:1). This resulted in 230 mg (62%) of the title product as a yellow oil.

(vi) Methyl 2-([1-[(2-chlorophenyl)methyl]-5-[3-(2-methylpropanamido)phenyl]-1H-pyrazol-3-yl]methoxy)-2-methylpropanoate: Into a 40-mL flask was placed a solution of methyl 2-[[5-(3-aminophenyl)-1-[(2-chlorophenyl) methyl]-1H-pyrazol-3-yl]methoxy]-2-methylpropanoate (200 mg, 0.48 mmol, 1.00 equiv), HATU (276 mg, 0.73 mmol, 1.50 equiv), 2-methylpropanoic acid (130 mg, 1.48 mmol, 3.00 equiv) and DIEA (187 mg, 1.45 mmol, 3.00 equiv) in DMF (20 mL). The resulting solution was stirred overnight at room temperature. The resulting solution was diluted with 200 mL of EtOAc, washed with 2×100 mL of brine, dried over anhydrous Na₂SO₄ and concentrated under vacuum. The residue was purified by Prep-TLC with DCM/MeOH (30:1). This resulted in 155 mg (66%) of the title product as a yellow solid.

(viii) 2-([1-[(2-Chlorophenyl)methyl]-5-[3-(2-methylpropanamido)phenyl]-1H-pyrazol-3-yl]methoxy)-2-methylpropanoic acid was prepared analogously as described in Step iv of Example 1. This resulted in 70 mg (48%) as a white solid. $^1$H-NMR (300 MHz, DMSO): δ1.09 (6H, d), 1.39 (6H, s), 2.57 (1H, p), 5.39 (2H, s), 6.40 (1H, s), 6.69-6.79 (1H, m), 7.00 (1H, dt), 7.21-7.48 (4H, m), 7.53-7.63 (1H, m), 7.78 (1H, t), 9.93 (1H, s).

Example 70: 2-([1-[(2-chlorophenyl)methyl]-5-(3-methanesulfonylphenyl)-1H-pyrazol-3-yl]methoxy)-2-methylpropanoic acid

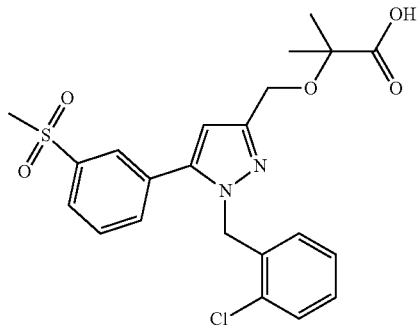 [SMILES: CC(C)(OCc1cc(-c2cccc(S(C)(=O)=O)c2)n(Cc2ccccc2Cl)n1)C(=O)O]

(i) Methyl 2-([1-[(2-chlorophenyl)methyl]-5-[3-(methylsulfanyl)phenyl]-1H-pyrazol-3-yl]methoxy)-2-methylpropanoate: Into a 30-mL flask purged and maintained with an inert atmosphere of N₂, was placed a solution of methyl 2-[[5-(3-aminophenyl)-1-[(2-chlorophenyl)methyl]-1H-pyrazol-3-yl]methoxy]-2-methylpropanoate (700 mg, 1.69 mmol, 1.00 equiv—prepared analogously as described in Example 69) in MeCN (10 mL). This was followed by the addition of dimethyl disulfide (319 mg, 3.39 mmol, 2.00 equiv). The resulting mixture was heated 60° C. for 1 h. To this was added tert-butylnitrite (350 mg, 3.40 mmol, 2.00 equiv) dropwise with stirring at room temperature. The resulting solution was stirred for 3 h at 60° C. in an oil bath, then diluted with 200 mL of EtOAc, washed with 2×100 mL of brine, dried over anhydrous Na₂SO₄ and concentrated under vacuum. The residue was applied onto Prep-TLC with EtOAc/petroleum ether (1:2). This resulted in 300 mg (40%) of the title product as a yellow oil.

(ii) Methyl 2-([1-[(2-chlorophenyl)methyl]-5-(3-methanesulfonylphenyl)-1H-pyrazol-3-yl]methoxy)-2-methylpropanoate: Into a 25-mL round-bottom flask was placed a solution of methyl 2-([1-[(2-chlorophenyl)methyl]-5-[3-(methylsulfanyl)phenyl]-1H-pyrazol-3-yl]methoxy)-2-methylpropanoate (300 mg, 0.67 mmol, 1.00 equiv) in MeOH/H₂O (10/5 mL). This was followed by the addition of dipotassium O-[(sulfonatoperoxy)sulfonyl]oxidanidolate (233 mg, 1.53 mmol, 1.00 equiv), in portions at room temperature. The resulting solution was stirred for 2 h at room temperature, then diluted with 200 mL of EtOAc, washed with 2×100 mL of brine, dried over anhydrous Na₂SO₄ and concentrated under vacuum. The residue was applied onto Prep-TLC with EtOAc/petroleum ether (1:3). This resulted in 180 mg (58%) of the title product as a yellow solid.

(iii) 2-([1-[(2-Chlorophenyl)methyl]-5-(3-methanesulfonylphenyl)-1H-pyrazol-3-yl]methoxy)-2-methylpropanoic acid was prepared analogously as described in Step iv of Example 1. This resulted in 30 mg (17%) as a white solid. $^1$H-NMR (400 MHz, MeOD): δ 1.54 (6H, s), 3.10 (3H, s), 4.61 (2H, s), 5.48 (2H, s), 6.67 (1H, s), 6.82 (1H, dd), 7.21-7.33 (2H, m), 7.35-7.42 (1H, m), 7.64-7.74 (2H, m), 7.90 (1H, q), 7.96-8.03 (1H, m).

Example 71: 2-([1-[(2-chlorophenyl)methyl]-5-(3-methanesulfonamidophenyl)-1H-pyrazol-3-yl]methoxy)-2-methylpropanoic acid

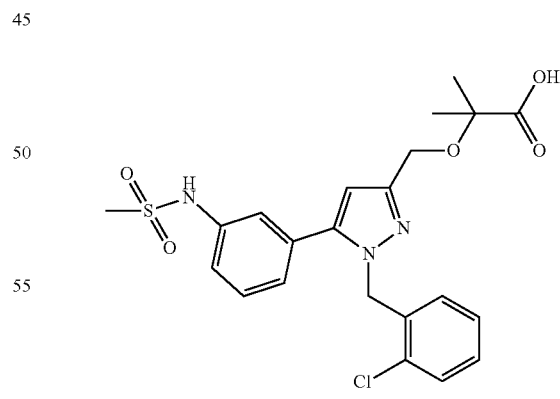

(i) Methyl 2-([1-[(2-chlorophenyl)methyl]-5-(3-methanesulfonamidophenyl)-1H-pyrazol-3-yl]methoxy)-2-methylpropanoate: Into a 25-mL round-bottom flask was placed a solution of methyl 2-[[5-(3-aminophenyl)-1-[(2-chlorophenyl)methyl]-1H-pyrazol-3-yl]methoxy]-2-methylpropanoate (200 mg, 0.48 mmol, 1.00 equiv—prepared analogously as described in Example 69), pyridine (75 mg, 0.95 mmol, 2.00 equiv), and 4-dimethylaminopyridine (6 mg, 0.05 mmol, 0.10 equiv) in DCM (10 mL). This was followed by the addition of methanesulfonyl chloride (83 mg, 0.72 mmol, 1.50 equiv) dropwise with stirring at 0° C. The resulting solution was stirred overnight at room temperature, then diluted with 100 mL of DCM, washed with 2×100 mL of brine, dried over anhydrous Na$_2$SO$_4$ and concentrated under vacuum. The residue was applied onto Prep-TLC with EtOAc/petroleum ether (1:4). This resulted in 100 mg (42%) of the title product as a yellow oil.

(ii) 2-([1-[(2-Chlorophenyl)methyl]-5-(3-methanesulfonamidophenyl)-1H-pyrazol-3-yl]methoxy)-2-methylpropanoic acid was prepared analogously as described in Step iv of Example 1. This resulted in 30.2 mg (31%) as a white solid. $^1$H-NMR (300 MHz, MeOD): δ 1.52 (6H, s), 2.04 (1H, s), 2.87 (3H, s), 4.58 (2H, s), 5.44 (2H, s), 6.56 (1H, s), 6.66-6.76 (1H, m), 7.12 (1H, dt), 7.25 (4H, dtd), 7.32-7.44 (2H, m).

Example 72: 2-([1-[(2-Chlorophenyl)methyl]-5-[3-(methylamino)phenyl]-1H-pyrazol-3-yl]methoxy)-2-methylpropanoic acid

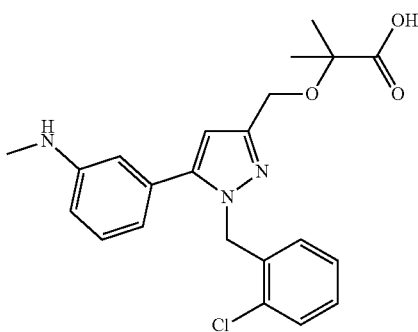 [SMILES: CNc1cccc(-c2cc(COC(C)(C)C(=O)O)nn2Cc2ccccc2Cl)c1]

(i) Methyl 2-([1-[(2-chlorophenyl)methyl]-5-[3-(methylamino)phenyl]-1H-pyrazol-3-yl]methoxy)-2-methylpropanoate: Into a 30-mL flask, paraformaldehyde (107 mg, 2.43 mmol, 5.00 equiv) was added to a solution of methyl 2-[[5-(3-aminophenyl)-1-[(2-chlorophenyl)methyl]-1H-pyrazol-3-yl]methoxy]-2-methylpropanoate (200 mg, 0.48 mmol, 1.00 equiv—prepared analogously as described in Example 69) in methanol (10 mL). This was followed by the addition of MeOna (0.45 mL, 5.00 equiv, 5.4M) dropwise with stirring at room temperature. The resulting solution was stirred for 2 h at 60° C. in an oil bath. To this was added NaBH$_4$ (92 mg, 2.43 mmol, 5.00 equiv) in portions at 0° C. The resulting solution was allowed to react, with stirring, for an additional 1 h while the temperature was maintained at 60° C. in an oil bath. The resulting solution was diluted with 100 mL of EtOAc. The resulting mixture was washed with 2×50 mL of Brine. The mixture was dried over anhydrous Na$_2$SO$_4$ and concentrated under vacuum. The residue was applied onto Prep-TLC with EtOAc/petroleum ether (1:4). This resulted in 100 mg (48%) of the title product as a yellow oil.

(ii) 2-([1-[(2-chlorophenyl)methyl]-5-(3-methanesulfonamidophenyl)-1H-pyrazol-3-yl]methoxy)-2-methylpropanoic acid was prepared analogously as described in Step iv of Example 1. This resulted in 30.2 mg as a white solid. $^1$H-NMR (300 MHz, MeOD): δ 1.52 (6H, s), 2.04 (1H, s), 2.87 (3H, s), 4.58 (2H, s), 5.44 (2H, s), 6.56 (1H, s), 6.66-6.76 (1H, m), 7.12 (1H, dt), 7.25 (4H, dtd), 7.32-7.44 (2H, m).

Example 73: 2-([1-[(2-chlorophenyl)methyl]-5-[3-[(2-methylpropyl)amino]phenyl]-1H-pyrazol-3-yl]methoxy)-2-methylpropanoic acid was prepared analogously as described in Example 72.

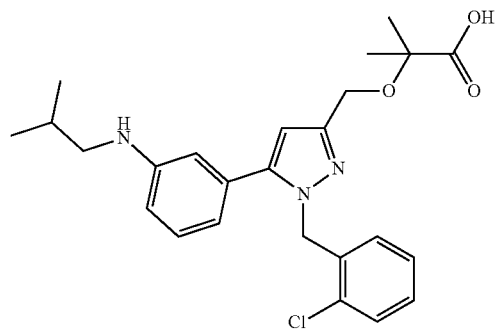 [SMILES: CC(C)CNc1cccc(-c2cc(COC(C)(C)C(=O)O)nn2Cc2ccccc2Cl)c1]

$^1$H-NMR (300 MHz, MeOD): δ 0.88 (6H, d), 1.52 (6H, s), 1.74 (1H, dp), 2.66 (2H, d), 4.57 (2H, s), 5.42 (2H, s), 6.40-6.77 (5H, m), 7.11 (1H, dd), 7.19-7.35 (2H, m), 7.35-7.47 (1H, m).

Example 74: 2-([1-[(o-Chlorophenyl)methyl]-5-[m-(isopropylamino)carbonylphenyl]-1H-pyrazol-3-yl]methoxy)-2-methylpropionic acid

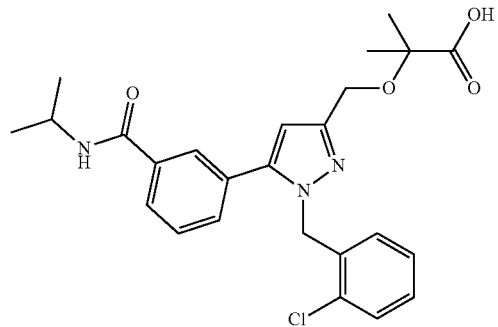 [SMILES: CC(C)NC(=O)c1cccc(-c2cc(COC(C)(C)C(=O)O)nn2Cc2ccccc2Cl)c1]

(i) 3-Acetyl-N-(propan-2-yl)benzamide: A suspension of 3-acetylbenzoic acid (10 g, 60.92 mmol), HATU (20 g, 52.60 mmol,) and propan-2-amine (4 g, 67.67 mmol) in DMF (180 mL). To the solution pre-cooled to −5° C. was added dropwise DIEA. Then the resulting mixture was stirred at room temperature for 2 h under N$_2$. The resulting mixture was poured into 100 mL water. The resulting residue was extracted with EtOAc (3×100 mL). The combined organic layers were washed with 300 mL brine, dried over anhydrous Na$_2$SO$_4$, filtered and concentrated under vacuum. This resulted in 11 g (88%) of the title product as a yellow solid.

(ii) Methyl 2-([1-[(2-chlorophenyl)methyl]-5-[3-[(propan-2-yl)carbamoyl]phenyl]-1H-pyrazol-3-yl]methoxy)-2-methylpropanoate was prepared analogously as described in Steps i-v of Example 69.

(iii) 2-([1-[(2-Chlorophenyl)methyl]-5-[3-[(propan-2-yl)carbamoyl]phenyl]-1H-pyrazol-3-yl]methoxy)-2-methylpropanoic acid was prepared analogously as described in Step iv of Example 1. This resulted in 80 mg as a white solid. $^1$H-NMR: (400 MHz, DMSO-d$_6$) δ 1.16 (6H, d), 1.41 (6H, s), 3.33 (5H, s), 4.02-4.17 (1H, m), 4.44 (2H, s), 5.40 (2H, s), 6.53 (1H, s), 6.75-6.88 (1H, m), 7.23-7.36 (2H, m), 7.41-7.47 (1H, m), 7.49-7.57 (2H, m), 7.81-7.98 (2H, m), 8.29 (1H, d), 12.63 (1H, s).

Example 75: 2-([1-[(2-chlorophenyl)methyl]-5-(phenylamino)-1H-pyrazol-3-yl]methoxy)-2-methylpropanoic acid

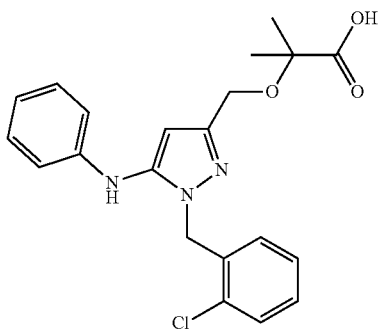 [SMILES: CC(C)(OCc1cc(Nc2ccccc2)n(Cc2ccccc2Cl)n1)C(=O)O]

(i) [(2-Chlorophenyl)methyl]hydrazine: Into a 500-mL round-bottom flask, was placed a solution of hydrazine hydrate (85%) (31 g, 8.50 equiv) in EtOH (100 mL). This was followed by the addition of a solution of 1-chloro-2-(chloromethyl)benzene (10 g, 62.10 mmol, 1.00 equiv) in EtOH (50 mL)(added dropwise over 1 hr at 70° C.). The resulting solution was stirred for 1 h at 70° C. The resulting mixture was concentrated under vacuum, then diluted with water. The resulting solution was extracted with EtOAc three times and the organic layers were combined. To the organic phase in an ice/water bath was added 4N HCl in dioxane. The solids that formed were collected by filtration. This resulted in 6.1 g (63%) of the title product as a white solid.

(ii) Ethyl 3-cyano-2-(potassiooxy)prop-2-enoate: Into a 50-mL round-bottom flask, was placed a solution of diethyl oxalate (5.06 g, 34.62 mmol, 1.00 equiv) in CH$_3$CN (20 mL). This was followed by the addition of t-BuOK (3.90 g, 34.76 mmol, 1.12 equiv), in portions at room temperature. The resulting solution was stirred for 1.5 h at room temperature. The solids that formed were collected by filtration. This resulted in 5.09 g (82%) of the title product as a yellow solid.

(iii) Ethyl 5-amino-1-[(2-chlorophenyl)methyl]-1H-pyrazole-3-carboxylate: Into a 40-mL flask was placed a solution of ethyl (2Z)-3-cyano-2-(potassiooxy)prop-2-enoate (2.0 g, 11.16 mmol, 1.00 equiv) in 1,4-dioxane (20 mL) while stirring at rt. This was followed by the addition of trifluoroacetic acid (2 mL) dropwise with stirring at room temperature. The resulting mixture was stirred at rt for 30 min. To this was added [(2-chlorophenyl)methyl]hydrazine (2.0 g, 12.77 mmol, 1.15 equiv), in portions at room temperature. The resulting solution was stirred overnight at room temperature. The resulting solution was diluted with 200 mL of EtOAc, washed with 2×200 mL of brine, dried over anhydrous Na$_2$SO$_4$ and concentrated under vacuum. The residue was applied onto a silica gel column with EtOAc/petroleum ether (1:3). This resulted in 1.8 g (58%) of the title product as a yellow oil.

(iv) Ethyl 1-[(2-chlorophenyl)methyl]-5-(phenylamino)-1H-pyrazole-3-carboxylate: Into a 30-mL sealed tube purged and maintained with an inert atmosphere of N$_2$, was placed a solution of ethyl 5-amino-1-[(2-chlorophenyl)methyl]-1H-pyrazole-3-carboxylate (1.0 g, 3.57 mmol, 1.00 equiv), iodobenzene (768 mg, 3.76 mmol, 1.05 equiv), 3rd Generation BrettPhos precatalyst (326 mg, 0.36 mmol, 0.10 equiv), and Cs$_2$CO$_3$ (1.4 g, 4.30 mmol, 1.20 equiv) in 1,4-dioxane (20 mL). The resulting solution was stirred for 3 h at 90° C. in an oil bath. The resulting solution was diluted with 200 mL of EtOAc, washed with 2×200 mL of brine, dried over Na$_2$SO$_4$ and concentrated under vacuum. The residue was applied onto a silica gel column with PE:EtOAc:DCM (3:1:0.1). This resulted in 1.3 g (102%) of the title product as a yellow solid.

(v) Methyl 5-[[(tert-butoxy)carbonyl](phenyl)amino]-1-[(2-chlorophenyl)methyl]-1H-pyrazole-3-carboxylate: Into a 50-mL round-bottom flask, was placed a solution of ethyl 1-[(2-chlorophenyl)methyl]-5-(phenylamino)-1H-pyrazole-3-carboxylate (800 mg, 2.25 mmol, 1.00 equiv) and 4-dimethylaminopyridine (548 mg, 4.49 mmol, 2.00 equiv) in toluene (20 mL). This was followed by the addition of di-tert-butyl dicarbonate (980 mg, 4.49 mmol, 2.00 equiv), in portions at room temperature. The resulting solution was heated to reflux for 1 overnight in an oil bath. The resulting solution was diluted with 200 mL of EtOAc, washed with 2×100 mL of brine, dried over anhydrous Na$_2$SO$_4$ and concentrated under vacuum. The residue was applied onto a silica gel column with EtOAc/petroleum ether (1:3). This resulted in 1.0 g (101%) of the title product as a colorless oil.

(vi) 2-[(5-[[(tert-butoxy)carbonyl](phenyl)amino]-1-[(2-chlorophenyl)methyl]-1H-pyrazol-3-yl)methoxy]-2-methylpropanoic acid was prepared analogously as described in Steps ii-iv of Example 1. This resulted in 200 mg as yellow oil.

(vii) 2-([1-[(2-Chlorophenyl)methyl]-5-(phenylamino)-1H-pyrazol-3-yl]methoxy)-2-methylpropanoic acid: Into a 25-mL round-bottom flask, was placed a solution of 2-[(5-[[(tert-butoxy)carbonyl](phenyl)amino]-1-[(2-chlorophenyl)methyl]-1H-pyrazol-3-yl)methoxy]-2-methylpropanoic acid (200 g, 400.01 mmol, 1.00 equiv) in DCM (10 mL). This was followed by the addition of trifluoroacetic acid (5 mL) dropwise with stirring at room temperature. The resulting solution was stirred for 1 h at room temperature. The resulting mixture was concentrated under vacuum. The crude product (150 mg) was purified by Prep-HPLC with the following conditions (2 #-AnalyseHPLC-SHIMADZU (HPLC-10)): Column, SunFire C18 OBD Prep Column, 0.1 nM, 5 uM, 19 mm×150 mm, mobile phase, Waters (0.1% TFA) and ACN (61.0% ACN up to 74.0% in 6 min); Detector, UV 254 nm). This resulted in 19.2 mg of the title product as a white solid. $^1$H-NMR (300 MHz, MeOD) δ 1.50 (6H, s), 4.48 (2H, s), 5.34 (2H, d), 6.18 (1H, s), 6.68-6.95 (4H, m), 7.11-7.30 (4H, m), 7.33-7.43 (1H, m).

Example 76: 2-([1-[(2-Chlorophenyl)methyl]-5-phenoxy-1H-pyrazol-3-yl]methoxy)-2-methylpropanoic acid

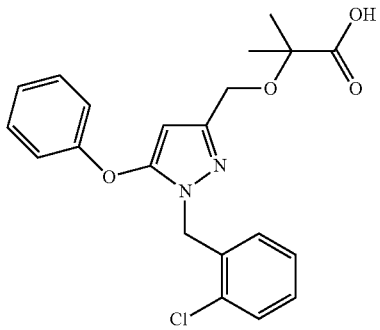 [SMILES: CC(C)(OCc1cc(Oc2ccccc2)n(Cc2ccccc2Cl)n1)C(=O)O]

(i) Ethyl 1-[(2-chlorophenyl)methyl]-5-oxo-4,5-dihydro-1H-pyrazole-3-carboxylate: Into a 250-mL round-bottom flask was placed a solution of [(2-chlorophenyl)methyl]hydrazine dihydrochloride (4 g, 17.54 mmol, 1.00 equiv) in EtOH (120 mL). 1,4-Diethyl 2-oxobutanedioate (0 mg, 1.30 equiv) was added. The resulting solution was heated to reflux overnight, then concentrated under vacuum. The residue was applied onto a silica gel column with EtOAc/petroleum ether (1:20~1:5). This resulted in 2.8 g (57%) of the title product as a yellow syrup.

(ii) Ethyl 1-[(2-chlorophenyl)methyl]-5-(2-nitrophenoxy)-1H-pyrazole-3-carboxylate: Into a 100-mL round-bottom flask, was placed ethyl 1-[(2-chlorophenyl)methyl]-5-oxo-4,5-dihydro-1H-pyrazole-3-carboxylate (2.8 g, 9.97 mmol, 1.00 equiv), 1-fluoro-2-nitrobenzene (2.8 g, 19.84 mmol, 2.00 equiv), $K_2CO_3$ (2.7 g, 19.57 mmol, 2.00 equiv) in DMF (20 mL). The resulting solution was stirred overnight at 90° C. in an oil bath. The resulting solution was diluted with EtOAc, washed with water and brine, dried over anhydrous $Na_2SO_4$, and concentrated under vacuum. The residue was applied onto a silica gel column with EtOAc/petroleum ether (1:50-1:10). This resulted in 0.8 g (20%) of the title product as yellow oil.

(iii) Ethyl 5-(2-aminophenoxy)-1-[(2-chlorophenyl)methyl]-1H-pyrazole-3-carboxylate: Into a 50-mL round-bottom flask was placed a solution of ethyl 1-[(2-chlorophenyl)methyl]-5-(2-nitrophenoxy)-1H-pyrazole-3-carboxylate (800 mg, 1.99 mmol, 1.00 equiv) in AcOH/$H_2O$ (3:1) (8 mL). Zn (600 mg, 9.38 mmol, 5.00 equiv) was added. The resulting mixture was stirred for 3 h at 60° C. in an oil bath. The solids were removed by filtration. The resulting mixture was concentrated under vacuum. The residue was applied onto a silica gel column with EtOAc/petroleum ether (1:30~1:5). This resulted in 540 mg (73%) of the title product as a yellow solid.

(iv) Ethyl 1-[(2-chlorophenyl)methyl]-5-phenoxy-1H-pyrazole-3-carboxylate: Into a 50-mL round-bottom flask was placed a solution of ethyl 5-(2-aminophenoxy)-1-[(2-chlorophenyl)methyl]-1H-pyrazole-3-carboxylate (540 mg, 1.45 mmol, 1.00 equiv) in THF (15 mL). tert-Butyl nitrite (450 mg, 4.36 mmol, 3.00 equiv) was added. The solution was stirred for 30 min at 60° C. The resulting mixture was concentrated under vacuum. The residue was purified with Prep-TLC (EtOAc:PE=1:3) This resulted in 220 mg (42%) of the title product as a solid.

(v) 2-([1-[(2-Chlorophenyl)methyl]-5-phenoxy-1H-pyrazol-3-yl]methoxy)-2-methylpropanoic acid was prepared analogously as described in Steps ii-iv of Example 1. This resulted in 17 mg as a white solid. $^1$H-NMR ($CD_3OD$, ppm): δ (300 MHz, MeOD) 1.46 (6H, s), 4.44 (2H, s), 5.35 (2H, s), 5.78 (1H, s), 6.90-7.00 (1H, m), 7.06-7.46 (8H, m).

Example 77: 2-([5-Benzyl-1-[(2-chlorophenyl)methyl]-1H-pyrazol-3-yl]methoxy)-2-methylpropanoic acid

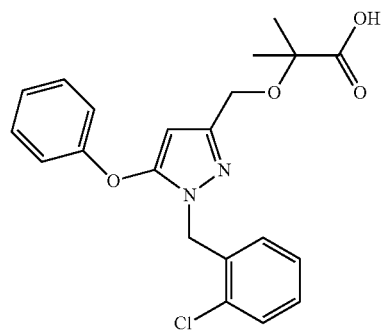 [SMILES: CC(C)(OCc1cc(Oc2ccccc2)n(Cc2ccccc2Cl)n1)C(=O)O]

(i) Ethyl 2,4-dioxo-5-phenylpentanoate: Into a 100-mL round-bottom flask was placed a solution of 1-phenylethan-1-one (1 g, 8.32 mmol, 1.00 equiv) in THF (25 mL). This was followed by the addition of NaH (269 mg, 11.21 mmol, 1.50 equiv), in portions at 0° C. in 30 min. To this was added diethyl oxalate (1.64 g, 11.22 mmol, 1.50 equiv). The resulting solution was stirred for 1 h at room temperature. The reaction mixture was cooled to 0° C. with a water/ice bath. The reaction was then quenched by the addition of 20 mL of water. The resulting solution was extracted with 3×50 mL of EtOAc, and the organic layers were combined and dried over anhydrous $Na_2SO_4$ and concentrated under vacuum. The residue was applied onto a silica gel column with EtOAc/petroleum ether (1:40). This resulted in 700 mg (36%) of the title product as a yellow liquid.

(ii) 2-([5-Benzyl-1-[(2-chlorophenyl)methyl]-1H-pyrazol-3-yl]methoxy)-2-methylpropanoic acid was prepared analogously as described in Steps iii-iv of Example 51. This resulted in 21 mg of the product as a white solid. $^1$H-NMR (300 MHz, MeOD): δ 1.48 (6H, s), 3.92 (2H, s), 4.50 (2H, s), 5.32 (2H, s), 6.23 (1H, s), 6.42-6.52 (1H, m), 7.07-7.30 (7H, m), 7.39 (1H, dd).

Example 78: This Example Intentionally Left Blank

Example 79: 2-[[1-[(2-Chlorophenyl)methyl]-5-(3-hydroxyphenyl)pyrazol-3-yl]methoxy]-2-methylpropanoic acid

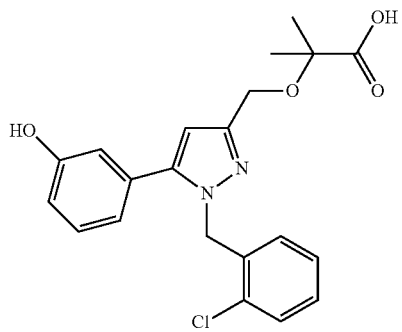 [SMILES: CC(C)(OCc1cc(-c2cccc(O)c2)n(Cc2ccccc2Cl)n1)C(=O)O]

(i) 2-[[1-[(2-Chlorophenyl)methyl]-5-(3-hydroxyphenyl)pyrazol-3-yl]methoxy]-2-methyl-propanoic acid: A solution of methyl 2-[[5-(3-benzyloxyphenyl)-1-[(2-chlorophenyl)methyl]pyrazol-3-yl]methoxy]-2-methyl-propanoate in mixture of acetic acid and conc HCl (8 mL) (3:1, v/v) was heated at 90° C. for 6 h. At the end of this period the reaction mixture was evaporated to dryness and the residue was chromatographed over SiO$_2$ using 0-20% gradient of MeOH in DCM to afford the title product. $^1$HNMR (CDCl$_3$): δ 1.55 (s, 6H), 4.61 (s, 2H), 5.40 (s, 2H), 6.38 (s, 1H), 6.74-6.83 (m, 4H), 7.18-7.35 (m, 4H).

Example 80: 2-[[1-[(2-Chlorophenyl)methyl]-5-[3-(oxetan-3-ylmethoxy)phenyl]pyrazol-3-yl]methoxy]-2-methyl-propanoic acid

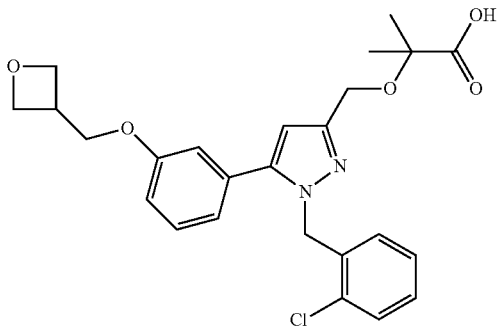 [SMILES: CC(C)(OCc1cc(-c2cccc(OCC3COC3)c2)n(Cc2ccccc2Cl)n1)C(=O)O]

(i) Methyl 2-[[1-[(2-chlorophenyl)methyl]-5-(3-hydroxyphenyl)pyrazol-3-yl]-methoxy]-2-methyl-propanoate: To a solution of 2-[[1-[(2-chlorophenyl)methyl]-5-(3-hydroxyphenyl)pyrazol-3-yl]methoxy]-2-methyl-propanoic acid (Example 79) in MeOH was added 4 drops of conc H$_2$SO$_4$, and the solution was refluxed for 16 h. The product was evaporated to dryness and the residue was chromatographed over SiO$_2$ using 0-25% gradient of MeOH in DCM to afford the title product.

(ii) Methyl 2-[[1-[(2-chlorophenyl)methyl]-5-[3-(oxetan-3-ylmethoxy)phenyl]pyrazol-3-yl]methoxy]-2-methyl-propanoate. To a solution of methyl 2-[[1-[(2-chlorophenyl)methyl]-5-(3-hydroxyphenyl)pyrazol-3-yl]methoxy]-2-methyl-propanoate (0.170 g, 0.410 mmol) in DMF was added oxetan-3-ylmethyl 4-methylbenzenesulfonate (0.149 g, 0.615 mmol) and K$_2$CO$_3$ (0.113 g, 0.820 mmol) at room temperature. The mixture was heated at 60° C. for 16 h. The reaction mixture was cooled to room temperature, water was added, and the mixture was extracted with EtOAc (20 mL×2). The combined organic layers were washed with water (20 mL) and brine (20 mL), dried over Na$_2$SO$_4$, and concentrated under reduced pressure. The residue was chromatographed over SiO$_2$ using 0-100% gradient of EtOAc in hexane to afford the title product. $^1$HNMR (CDCl$_3$): δ 1.54 (s, 6H), 3.33-3.36 (m, 1H), 3.77 (s, 3H), 3.97 (d, 2H), 4.30 (t, 2H), 4.56 (s, 2H), 4.84 (t, 2H), 5.40 (s, 2H), 6.53 (s, 1H), 6.77-6.90 (m, 4H), 7.19-7.37 (m, 4H).

(iii) 2-[[1-[(2-Chlorophenyl)methyl]-5-[3-(oxetan-3-ylmethoxy)phenyl]pyrazol-3-yl]methoxy]-2-methyl-propanoic acid was prepared analogously as described in Step iv of Example 1, yielding the title product (20 mg). $^1$HNMR (CDCl$_3$): δ 1.55 (s, 6H), 3.34-3.74 (m, 1H), 3.98 (d, 2H), 4.49 (t, 2H), 4.63 (s, 2H), 4.83 (t, 2H), 5.43 (s, 2H), 6.44 (s, 1H), 6.76-6.93 (m, 4H), 7.20-7.37 (m, 4H).

Example 81: 2-[[1-[(2-chlorophenyl)methyl]-5-(3-methoxyphenyl)pyrazol-3-yl]methoxy]-2-methyl-N-methylsulfonyl-propanamide

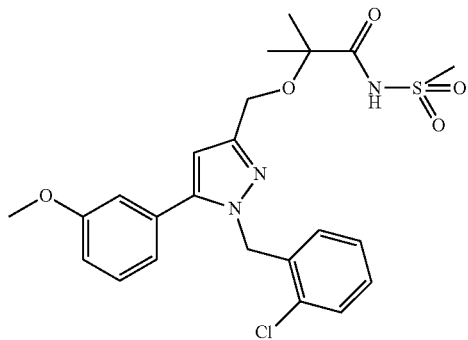 [SMILES: COc1cccc(-c2cc(COC(C)(C)C(=O)NS(C)(=O)=O)nn2Cc2ccccc2Cl)c1]

To a solution of Example 14 (2-[[1-[(2-chlorophenyl)methyl]-5-(3-methoxyphenyl)-pyrazol-3-yl]methoxy]-2-methyl-propanoic acid) (0.08 g, 0.192 mmol) in CH$_3$CN was added CDI (0.047 g, 0.288 mmol) and methanesulfonamide (0.022 g, 0.23 mmol) at rt. The mixture was stirred at rt for 16 h. The solvent was evaporated and the residue was chromatographed over SiO$_2$ using 0-20% gradient of MeOH in DCM to afford the title product. $^1$HNMR (CDCl$_3$): δ 1.55 (s, 6H), 3.21 (s, 3H), 3.67 (s, 3H), 4.58 (s, 2H), 5.48 (s, 2H), 6.36 (s, 1H), 6.75-6.92 (m, 4H), 7.18-7.35 (m, 4H).

Example 82: Methyl 2-[[1-[(2-chlorophenyl)methyl]-5-(3-methoxyphenyl)pyrazol-3-yl]methoxy]-2-methyl-propanoate was prepared analogously as described in Example 1, omitting Step iv. $^1$HNMR(CDCl$_3$): δ 1.54 (s, 6H), 3.65 (s, 3H), 3.77 (s, 3H), 4.56 (s, 2H), 5.37 (s, 2H), 6.53 (s, 1H), 6.71-6.78 (m, 2H), 6.85-6.90 (m 2H), 7.10-7.13 (m, 1H), 7.21-7.27 (m, 2H), 7.51-7.53 (m 1H).

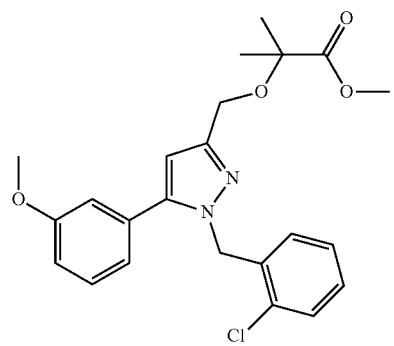 [SMILES: COC(=O)C(C)(C)OCc1cc(-c2cccc(OC)c2)n(Cc2ccccc2Cl)n1]

Biological Activity Assays

The following are assays that may be used to evaluate the biological efficacy of compounds of Formula (I) in a manner similar to that previously reported for MCT1 and MCT4 and are known to those with skill in the art. See, e.g., Murray, C. M. et al., "Monocarboxylate transporter MCT1 is a target for immunosuppression," *Nature chemical biology* 1, 371-376 (2005); and Ovens, M. J., et al., "AR-C155858 is a potent inhibitor of monocarboxylate transporters MCT1 and MCT2 that binds to an intracellular site involving transmembrane helices 7-10," *The Biochemical Journal* 425, 523-530, (2010).

Assay 1: Lactate Transport in MCT4-Expressing MDA-MB-453 Breast Cancer Cells.

MCT4 may be stably expressed in MDA-MB-453 breast cancer cells that do not express native MCT1 or MCT4. MCT4 activity may be assessed by monitoring the intracellular pH change that accompanies lactate/proton symport, using the pH-sensitive fluorescent dye 2',7'-bis-(carboxyethyl)-5(6)-carboxyfluorescein (BCECF), in a manner similar to that previously reported for MCT1 and MCT4. The following is an exemplary procedure for assaying MCT4 activity of the compounds of Formula (I).

Preparing BCECF-Loaded Cells:

Cells (~7×10$^6$) are trypsinized (0.05% Trypsin-EDTA), pelleted (300 g, 5 min), and resuspended in 1 mL Tyrode's Solution, pH 7.4 (119 mM NaCl, 5 mM KCl, 25 mM HEPES, pH 7.4, 2 mM CaCl$_2$), 2 mM MgCl$_2$, 6 g/L glucose). 10 µL of a 30 mM DMSO stock of BCECF-AM ester (Life Technologies) is added and the cells are incubated at 37° C. for 5 min. The cells are pelleted (300 g, 5 min), washed once with 1 mL Tyrode's Solution, pH 7.4, re-pelleted (300 g, 5 min), and resuspended in 1 mL Tyrode's Solution, pH 7.4.

Lactate Transport Assay:

2.5 µL BCECF-loaded cells, along with either 10 µL DMSO or 100×compound in DMSO, are added to 937.5 µL of Tyrode's Solution in a quartz 1.0 mL cuvette (PerkinElmer, B0631116). Fluorescence measurements are performed on a PerkinElmer LS55 fluorescence spectrometer with dual excitation wavelengths achieved using a filter wheel (FL Winlab program: Fast Filter; Excitation 490/440; Emission 535). After establishing baseline BCECF fluorescence (around 10-20 s), 50 µL of 1 M sodium L-lactate (Sigma-Aldrich) is added to the cuvette (final concentration: 50 mM) and rapidly mixed. The time-dependent decrease in BCECF fluorescence (490/440 ratio) may be fit to an exponential decay curve (Prism GraphPad) to determine the rate of lactate transport.

Assay 2: MCT4-Mediated Lactate Transport in NCI-H358 Lung Adenocarcinoma Cells.

NCI-H358 lung adenocarcinoma cells may be used to measure MCT4 activity in cells with high native levels of MCT4 and low levels of MCT1 and are known to those with skill in the art. Preparation of BCECF-loaded cells and lactate transport activity may be determined as described for Assay 1.

Assay 3: MCT4-Mediated Lactate Transport in MDA-MB-231 Breast Cancer Cells.

MDA-MB-231 breast cancer cells may be used to measure MCT4 activity in cells with high native levels of MCT4 and low levels of MCT1 and are known to those with skill in the art. Preparation of BCECF-loaded cells and lactate transport activity may be determined as described for Assay 1.

Assay 4: MCT1-Mediated Lactate Transport in BT20 Breast Cancer Cells.

MCT1 activity may be measured using BT-20 breast cancer cells that express high native levels of MCT1, but do not express MCT4 and are known to those with skill in the art. Preparation of BCECF loaded cells are as described for Assay 1. Lactate transport assay is as described for Assay 1, except 10 mM L-lactate (rather than 50 mM) is added.

Results of the assays above are given below in Tables 2-3. As can be seen, most compounds disclosed herein are selective for MCT4 over MCT1.

TABLE 2

| Example | MCT4 IC$_{50}$ (nM) MDA-MB-453 + MCT4 | MCT4 IC$_{50}$ (nM) NCI-H358 | MCT1 IC$_{50}$ (nM) BT20 |
|---|---|---|---|
| 1 | 340 | 140 | 50,000 |
| 2 | 450 | 240 | 29,000 |
| 3 | 72 | 60 | 25,000 |
| 4 | 68 | 54 | 33,000 |
| 5 | 160 | 63 | 1,800 |
| 6 | 2,400 | 4,600 | 6,600 |
| 7 | 720 | 460 | 70,000 |
| 8 | 69 | 81 | 46,000 |
| 9 | 320 | 340 | 39,000 |
| 10 | 21 | 33 | 8,800 |
| 11 | 45 | 25 | 29,000 |
| 12 | 38 | 49 | 58,000 |
| 13 | 20 | 22 | 17,000 |
| 14 | 26 | 44 | >100,000 |
| 15 | 900 | 440 | >33,000 |
| 16 | 1,000 | 640 | 73,000 |
| 17 | 440 | 860 | 1,200 |
| 18 | 5,300 | 4,200 | 45,000 |
| 19 | 110 | 160 | 57,000 |
| 20 | 17,000 | 22,000 | 7,900 |
| 21 | 35,000 | 48,000 | 300,000 |
| 22 | 14,000 | 39,000 | 150,000 |
| 23 | 1,500 | 2,100 | >300,000 |

TABLE 3

| Example | MCT4 IC$_{50}$ (nM) MDA-MB-231 | MCT1 IC$_{50}$ (nM) BT20 |
|---|---|---|
| 14 | 30 | >100,000 |
| 24 | 30 | >100,000 |
| 25 | 33 | 77,000 |
| 26 | 9.4 | 27,000 |
| 27 | 1.0 | 5,600 |
| 28 | 12 | 15,000 |
| 29 | 3.7 | 16,000 |
| 30 | 8.8 | 27,000 |
| 31 | 53 | 42,000 |
| 32 | 79 | 83,000 |
| 33 | 3.2 | 9,100 |
| 34 | 9.3 | >11,000 |
| 35 | 5.2 | 59,000 |
| 36 | 82 | 50,000 |
| 37 | 7.6 | 8,400 |
| 38 | 48 | 60,000 |
| 39 | 5.4 | 10,000 |
| 40 | 520 | >100,000 |
| 41 | 55 | 1,200 |
| 42 | 2.6 | 9,800 |
| 43 | 13 | >33,000 |
| 44 | 1.1 | 8,400 |
| 45 | 19 | 12,000 |
| 46 | 142 | 47,000 |
| 47 | 410 | >100,000 |
| 48 | 89 | 55,000 |
| 49 | 240 | 130,000 |
| 50 | 70 | 34,000 |
| 51 | 15 | 6,000 |
| 52 | 190 | 84,000 |
| 53 | 160 | >100,000 |
| 54 | 37 | 27,000 |
| 55 | 260 | >100,000 |
| 56 | 8,000 | >133,000 |
| 57 | 110 | >133,000 |
| 58 | 150 | 78,000 |
| 59 | 340 | 81,000 |
| 60 | 13 | 44,000 |
| 61 | 3.1 | 11,000 |
| 62 | 33 | 27,000 |
| 63 | 37 | 17,000 |
| 64 | 8.3 | 45,000 |
| 65 | 8.0 | 13,000 |
| 66 | 7.8 | 45,000 |
| 67 | 11 | 17,000 |

TABLE 3-continued

| Example | MCT4 IC$_{50}$ (nM) MDA-MB-231 | MCT1 IC$_{50}$ (nM) BT20 |
|---|---|---|
| 68 | 9.1 | 26,000 |
| 69 | 5,800 | >100,000 |
| 70 | 9,300 | >100,000 |
| 71 | 34,000 | 64,000 |
| 72 | 220 | 45,000 |
| 73 | 21 | >11,000 |
| 74 | 6,400 | >100,000 |
| 75 | 1,700 | >100,000 |
| 76 | 400 | 38,000 |
| 77 | 340 | 9,000 |
| 79 | 59 | 15,000 |
| 80 | 81 | 61,000 |
| 81 | 6,300 | 6,600 |
| 82 | 460 | 16,000 |

Metabolic Stability Assays

The following are assays that may be used to evaluate the metabolic stability of compounds of Formula (I) in human or mouse microsomes.

1. Master solution: 200 µL of 200 mM Phosphate buffer, 106 µL of ultra-pure water, 40 µL of 50 mM MgCl$_2$, and 10 µL of 20 mg/mL liver microsomes (human or mouse).
2. Two separated experiments were performed as follows. a) With NADPH: 10 µL of 20 mg/mL liver microsomes and 40 µL of 10 mM NADPH were added to the incubations. The final concentrations of microsomes and NADPH were 0.5 mg/mL and 1 mM, respectively. b) Without NADPH: 10 µL of 20 mg/mL liver microsomes and 40 µL of ultra-pure H2O were added to the incubations. The final concentration of microsomes was 0.5 mg/mL.
3. The reaction was started with the addition of 4 µL of 200 µM control compound or test compound solutions. Verapamil was used as positive control in this study. The final concentration of test compound or control compound was 2 µM.
4. Aliquots of 50 µL were taken from the reaction solution at 0, 15, 30, 45 and 60 min. The reaction was stopped by the addition of 4 volumes of cold acetonitrile with IS (100 nM alprazolam, 200 nM labetalol and 2 µM ketoprofen). Samples were centrifuged at 3, 220 g for 40 minutes. Aliquot of 90 µL of the supernatant was mixed with 90 µL of ultra-pure H2O and then used for LC-MS/MS analysis.
5. Data analysis. All calculations were carried out using Microsoft Excel. Peak areas were determined from extracted ion chromatograms. The slope value, k, was determined by linear regression of the natural logarithm of the remaining percentage of the parent drug vs. incubation time curve. The in vitro half-life (in vitro t½) was determined from the slope value: in vitro $t_{1/2} = -(0.693)/k$.

Results of the assays above are given below in Table 4.

TABLE 4

| Example | Human microsome $t_{1/2}$ | Human microsome % 60 min | Mouse microsome $t_{1/2}$ | Mouse microsome % 60 min |
|---|---|---|---|---|
| 14 | 245 | 82 | 1300 | 95 |
| 27 | 50 | 43 | 61 | 50 |
| 35 | 115 | 67 | 35 | 31 |
| 36 | 290 | 85 | 1200 | 99 |
| 38 | 76 | 56 | 79 | 61 |
| 39 | 380 | 89 | 370 | 88 |
| 54 | 78 | 59 | 760 | 95 |
| 57 | 190 | 80 | >2000 | 100 |
| 64 | 200 | 82 | 270 | 84 |
| 65 | 140 | 78 | 560 | 92 |
| 66 | 120 | 73 | 260 | 83 |
| 68 | 790 | 95 | 380 | 91 |

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A compound of structural Formula I

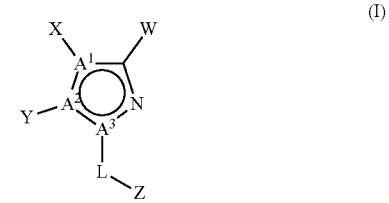

wherein:

A$^1$, A$^2$, and A$^3$ are independently chosen from N and C, wherein at least one of A$^1$, A$^2$, and A$^3$ is N;

L is chosen from a bond and methylene;

W is chosen from

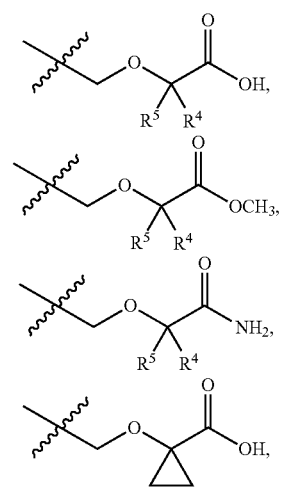

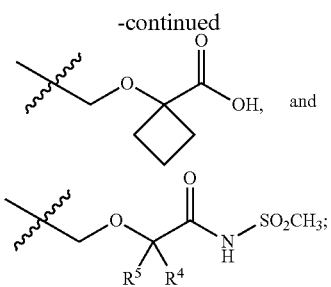

R⁴ and R⁵ are independently chosen from $C_1$-$C_6$alkyl, wherein R⁴ and R⁵ together comprise no more than 6 carbons;

X is H;

Y is chosen from alkenyl, alkenylamino, alkyl, aminoalkenyl, aminoalkyl, aryl, cycloalkyl, and heteroaryl, any of which may be optionally substituted with one to three R² groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl; and Z is chosen from aryl and heteroaryl, either of which may be optionally substituted with one to three R³ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

2. A method for treating a disease condition comprising administering to a subject in need thereof a therapeutically effective amount of a compound of structural Formula I

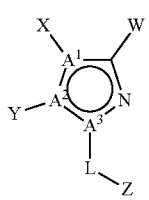

(I)

and/or a salt thereof, wherein the condition is cancer which has developed resistance to chemotherapeutic drugs and/or ionizing radiation, and wherein:

A¹, A², and A³ are independently chosen from N and C, wherein at least one of A¹, A², and A³ is N;

L is chosen from a bond and methylene;

W is chosen from

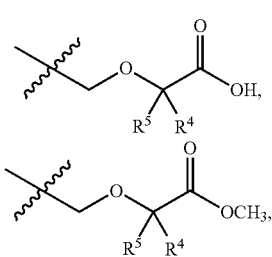

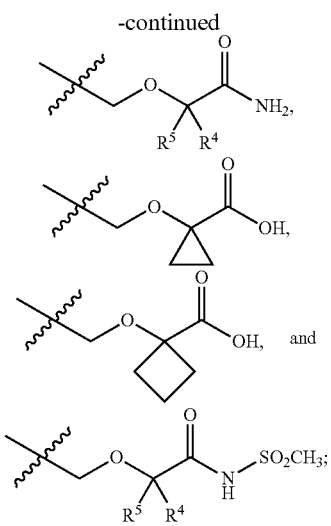

R⁴ and R⁵ are independently chosen from $C_1$-$C_6$alkyl, wherein R⁴ and R⁵ together comprise no more than 6 carbons;

X is hydrogen;

Y is chosen from alkenyl, alkenylamino, alkyl, aminoalkenyl, aminoalkyl, aryl, cycloalkyl, and heteroaryl, any of which may be optionally substituted with one to three R² groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl; and Z is chosen from aryl and heteroaryl, either of which may be optionally substituted with one to three R³ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

3. The compound of claim 1, wherein
A¹ and A² are C; and
A³ is N.

4. The compound of claim 3, wherein L is a bond.

5. The compound of claim 4, wherein Z is chosen from phenyl and pyridinyl, either of which may be optionally substituted with one to three R³ groups each independently chosen from alkyl, alkenyl, alkoxy, haloalkyl, alkylamino, amino, halo, cycloalkyl, aryl, and heteroaryl.

6. The compound of claim 5, wherein Y is chosen from aryl and heteroaryl, either of which may be optionally substituted with one to three R² groups each independently chosen from alkenyl, alkoxy, cycloalkoxy, cycloalkylmethoxy, haloalkoxy, alkyl, aryl, halo, heteroaryl, and haloalkyl.

7. The compound of claim 6, wherein:
Y is phenyl, substituted with an R² group chosen from alkoxy, cycloalkoxy, cycloalkylmethoxy, haloalkoxy, alkyl, halo, and haloalkyl; and
Z is phenyl, substituted with an R³ group chosen from alkyl, alkoxy, haloalkyl, alkylamino, amino, and halo.

8. The compound of claim 7, wherein R² is cycloalkoxy and R³ is amino.

9. The compound of claim 8, wherein R⁴ and R⁵ are methyl.

10. The method of claim 2, wherein
A¹ and A² are C; and
A³ is N.

11. The method of claim 10, wherein L is a bond.

12. The method of claim 11, wherein Z is chosen from phenyl and pyridinyl, either of which may be optionally substituted with one to three R³ groups each independently chosen from alkyl, alkenyl, alkoxy, haloalkyl, alkylamino, amino, halo, cycloalkyl, aryl, and heteroaryl.

13. The method of claim 12, wherein Y is chosen from aryl and heteroaryl, either of which may be optionally substituted with one to three R² groups each independently chosen from alkenyl, alkoxy, cycloalkoxy, cycloalkylmethoxy, haloalkoxy, alkyl, aryl, halo, heteroaryl, and haloalkyl.

14. The method of claim 13, wherein:
Y is phenyl, substituted with an R² group chosen from alkoxy, cycloalkoxy, cycloalkylmethoxy, haloalkoxy, alkyl, halo, and haloalkyl; and
Z is phenyl, substituted with an R³ group chosen from alkyl, alkoxy, haloalkyl, alkylamino, amino, and halo.

15. The method of claim 14, wherein R² is cycloalkoxy and R³ is amino.

16. The method of claim 15, wherein R⁴ and R⁵ are methyl.

17. A method for treating cardiac hypertrophy, comprising administering to a subject in need thereof a therapeutically effective amount of a compound of structural Formula I

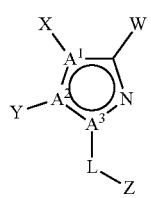

and/or a salt thereof,
wherein:
A¹, A², and A³ are independently chosen from N and C, wherein at least one of A¹, A², and A³ is N;
L is chosen from a bond and methylene;
W is chosen from

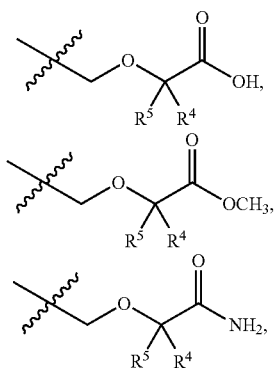

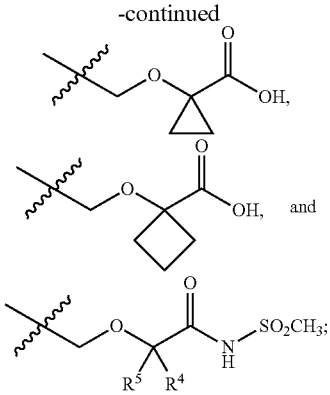

R⁴ and R⁵ are independently chosen from $C_1$-$C_6$alkyl, wherein R⁴ and R⁵ together comprise no more than 6 carbons;
X is hydrogen;
Y is chosen from alkenyl, alkenylamino, alkyl, aminoalkenyl, aminoalkyl, aryl, cycloalkyl, and heteroaryl, any of which may be optionally substituted with one to three R² groups each independently chosen from alkyl, alkenyl, alkoxy, haloalkyl, haloalkoxy, cycloalkoxy, cycloalkylmethoxy, alkylamino, amino, amido, sulfonamido, halo, cyano, hydroxy, cycloalkyl, aryl, and heteroaryl; and
Z is chosen from aryl and heteroaryl, either of which may be optionally substituted with one to three R³ groups each independently chosen from alkyl, alkenyl, alkoxy, haloalkyl, haloalkoxy, alkylamino, amino, amido, sulfonamido, halo, cyano, hydroxy, cycloalkyl, aryl, and heteroaryl.

18. The method of claim 17, wherein
A¹ and A² are C; and
A³ is N.

19. The method of claim 18, wherein L is a bond.

20. The method of claim 19, wherein Z is chosen from phenyl and pyridinyl, either of which may be optionally substituted with one to three R³ groups each independently chosen from alkyl, alkenyl, alkoxy, haloalkyl, alkylamino, amino, halo, cycloalkyl, aryl, and heteroaryl.

21. The method of claim 20, wherein Y is chosen from aryl and heteroaryl, either of which may be optionally substituted with one to three R² groups each independently chosen from alkenyl, alkoxy, cycloalkoxy, cycloalkylmethoxy, haloalkoxy, alkyl, aryl, halo, heteroaryl, and haloalkyl.

22. The method of claim 21, wherein:
Y is phenyl, substituted with an R² group chosen from alkoxy, cycloalkoxy, cycloalkylmethoxy, haloalkoxy, alkyl, halo, and haloalkyl; and
Z is phenyl, substituted with an R³ group chosen from alkyl, alkoxy, haloalkyl, alkylamino, amino, and halo.

23. The method of claim 22, wherein R⁴ and R⁵ are methyl.

* * * * *